(12) United States Patent
Cho

(10) Patent No.: US 7,030,106 B2
(45) Date of Patent: Apr. 18, 2006

(54) STEROL ABSORPTION INHIBITOR COMPOSITIONS

(75) Inventor: Wing-Kee Philip Cho, Princeton, NJ (US)

(73) Assignee: Schering Corporation, Kenilworth, NJ (US)

(*) Notice: Subject to any disclaimer, the term of this patent is extended or adjusted under 35 U.S.C. 154(b) by 0 days.

(21) Appl. No.: 10/136,968

(22) Filed: May 1, 2002

(65) Prior Publication Data

US 2002/0192203 A1 Dec. 19, 2002

Related U.S. Application Data

(62) Division of application No. 10/057,323, filed on Jan. 25, 2002.
(60) Provisional application No. 60/264,396, filed on Jan. 26, 2001, and provisional application No. 60/323,839, filed on Sep. 21, 2001.

(51) Int. Cl.
  *A61K 31/397* (2006.01)
  *A61K 9/20* (2006.01)
  *A61K 6/00* (2006.01)
  *A61K 7/00* (2006.01)

(52) U.S. Cl. .................. 514/210.03; 424/401; 424/464; 424/465

(58) Field of Classification Search ............ 514/210.03; 424/401, 464, 465
See application file for complete search history.

(56) References Cited

U.S. PATENT DOCUMENTS

| | | |
|---|---|---|
| 2,809,194 A | 10/1957 | Novello |
| 3,108,097 A | 10/1963 | Ugi |
| 3,152,173 A | 10/1964 | Ehrhart |
| 3,267,104 A | 8/1966 | Hermans |
| 3,399,192 A | 8/1968 | Regnier |
| 3,692,895 A | 9/1972 | Nelson |
| 3,716,583 A | 2/1973 | Nakamura |
| 3,781,328 A | 12/1973 | Witte |
| 3,948,973 A | 4/1976 | Phillips |
| 4,072,705 A | 2/1978 | Mieville |
| 4,075,000 A | 2/1978 | Abdulla |
| 4,144,232 A | 3/1979 | Koppel |
| 4,148,923 A | 4/1979 | Giudicelli |
| 4,166,907 A | 9/1979 | Krapcho |
| 4,178,695 A | 12/1979 | Erbeia |
| 4,179,515 A | 12/1979 | Mieville |
| 4,235,896 A | 11/1980 | Mieville |
| 4,239,763 A | 12/1980 | Milavec |
| 4,250,191 A | 2/1981 | Edwards |
| 4,260,743 A | 4/1981 | Bose |
| 4,304,718 A | 12/1981 | Kamiya |
| 4,375,475 A | 3/1983 | Willard |
| 4,443,372 A | 4/1984 | Luo |
| 4,444,784 A | 4/1984 | Hoffman |
| 4,472,309 A | 9/1984 | Kamiya |
| 4,479,900 A | 10/1984 | Luo |
| 4,500,456 A | 2/1985 | Spitzer |
| 4,534,786 A | 8/1985 | Luo |
| 4,564,609 A | 1/1986 | Tamura |
| 4,567,195 A | 1/1986 | Schwarz |
| 4,576,748 A | 3/1986 | Greenlee |
| 4,576,749 A | 3/1986 | Zahler |
| 4,576,753 A | 3/1986 | Kamiya |
| 4,581,170 A | 4/1986 | Mueller |
| 4,595,532 A | 6/1986 | Miller |
| 4,602,003 A | 7/1986 | Malinow |
| 4,602,005 A | 7/1986 | Malinow |
| 4,614,614 A | 9/1986 | Ernest |
| 4,616,047 A | 10/1986 | Lafon |
| 4,620,867 A | 11/1986 | Luo |
| 4,626,549 A | 12/1986 | Molloy |
| 4,633,017 A | 12/1986 | Mueller |
| 4,642,903 A | 2/1987 | Davies |
| 4,654,362 A | 3/1987 | Lommen |
| 4,675,399 A | 6/1987 | Miller |
| 4,680,289 A | 7/1987 | Applezweig |
| 4,680,391 A | 7/1987 | Firestone |
| 4,687,777 A | 8/1987 | Meguro et al. |
| 4,739,101 A | 4/1988 | Bourgogne |
| 4,778,883 A | 10/1988 | Yoshioka |
| 4,784,734 A | 11/1988 | Torii |
| 4,794,108 A | 12/1988 | Kishimoto |
| 4,800,079 A | 1/1989 | Boyer |
| 4,803,266 A | 2/1989 | Kawashima |
| 4,814,354 A | 3/1989 | Ghebre-Sellassie |
| 4,834,846 A | 5/1989 | Abramson |
| 4,871,752 A | 10/1989 | Zermatter |

(Continued)

FOREIGN PATENT DOCUMENTS

| | | |
|---|---|---|
| BE | 884722 A | 12/1980 |
| CA | 2253769 | 11/1999 |
| DE | 2046823 A | 3/1972 |

(Continued)

OTHER PUBLICATIONS

Remington's Pharmaceutical Sciences, 18th ed., 1990, p. 1319, 1633–1647.*

T. Kosoglou et al., "CoAdministration of Simvastatin and Ezetimbibe Leads to Significant Reduction in LDL–Cholesterol", Proceedings of 3$^{rd}$ International Congress on Coronary, Artery Disease from Prevention to Intervention, Lyon, France p. 71 (2000), XP008027568.

(Continued)

*Primary Examiner*—San-ming Hui
(74) *Attorney, Agent, or Firm*—Am M. Cammoni

(57) ABSTRACT

The present invention provides compositions, therapeutic combinations and methods including: (a) at least one peroxisome proliferator-activated receptor activator; and (b) at least one substituted azetidinone or substituted β-lactam sterol absorption inhibitor which can be useful for treating vascular conditions, diabetes, obesity and lowering plasma levels of sterols.

2 Claims, No Drawings

U.S. PATENT DOCUMENTS

| | | | |
|---|---|---|---|
| 4,876,365 A | 10/1989 | Kirkup | |
| 4,879,301 A | 11/1989 | Umio | |
| 4,895,726 A | 1/1990 | Curtet | |
| 4,925,672 A | 5/1990 | Gremm | |
| 4,937,267 A | 6/1990 | Holloway | |
| 4,939,248 A | 7/1990 | Yoshioka | |
| 4,952,689 A | 8/1990 | Kawashima | |
| 4,961,890 A | 10/1990 | Boyer | |
| 4,983,597 A | 1/1991 | Yang | |
| 4,990,535 A | 2/1991 | Cho | |
| 5,021,461 A | 6/1991 | Robinson et al. | |
| 5,030,628 A | 7/1991 | Joyeau | |
| 5,073,374 A | 12/1991 | McCarty | |
| 5,091,525 A | 2/1992 | Brennan | |
| 5,093,365 A | 3/1992 | Berge | |
| 5,099,034 A | 3/1992 | Yoshida | |
| 5,100,675 A | 3/1992 | Cho | |
| 5,106,833 A | 4/1992 | Broze | |
| 5,110,730 A | 5/1992 | Edgington | |
| 5,112,616 A | 5/1992 | McCarty | |
| 5,120,713 A | 6/1992 | Mugica | |
| 5,120,729 A | 6/1992 | Chabala | |
| 5,130,333 A | 7/1992 | Pan | |
| 5,145,684 A | 9/1992 | Liversidge | |
| 5,157,025 A | 10/1992 | Aberg | |
| 5,162,117 A | 11/1992 | Stupak | |
| 5,178,878 A | 1/1993 | Wehling | |
| 5,188,825 A | 2/1993 | Iles | |
| 5,190,970 A | 3/1993 | Pan | |
| 5,204,461 A | 4/1993 | Murayama | |
| 5,219,574 A | 6/1993 | Wehling | |
| 5,223,264 A | 6/1993 | Wehling | |
| 5,229,362 A | 7/1993 | Kirst | |
| 5,229,381 A | 7/1993 | Doherty | |
| 5,229,510 A | 7/1993 | Knight | |
| 5,260,305 A | 11/1993 | Dennick | |
| 5,278,176 A | 1/1994 | Lin | |
| H1286 H | 2/1994 | Eisman | |
| 5,286,631 A | 2/1994 | Boeck | |
| 5,298,497 A | 3/1994 | Tschollar | |
| 5,306,817 A | 4/1994 | Thiruvengadam | |
| 5,318,767 A | 6/1994 | Liversidge | |
| 5,348,953 A | 9/1994 | Doherty | |
| 5,350,868 A | 9/1994 | Yoshida | |
| 5,358,852 A | 10/1994 | Wu | |
| 5,384,124 A | 1/1995 | Courteille | |
| 5,385,885 A | 1/1995 | Gasic | |
| 5,399,363 A | 3/1995 | Liversidge | |
| 5,401,513 A | 3/1995 | Wehling | |
| 5,412,092 A | 5/1995 | Rey | |
| 5,429,824 A | 7/1995 | June | |
| 5,446,464 A | 8/1995 | Feldle | |
| 5,461,039 A | 10/1995 | Tschollar | |
| 5,464,632 A | 11/1995 | Cousin | |
| 5,494,683 A | 2/1996 | Liversidge | |
| 5,503,846 A | 4/1996 | Wehling | |
| 5,510,118 A | 4/1996 | Bosch | |
| 5,510,466 A | 4/1996 | Krieger | |
| 5,518,187 A | 5/1996 | Bruno | |
| 5,518,738 A | 5/1996 | Eickhoff | |
| 5,545,628 A | 8/1996 | Deboeck | |
| 5,550,229 A | 8/1996 | Iwasaki | |
| 5,552,160 A | 9/1996 | Liversidge | |
| 5,561,227 A | 10/1996 | Thiruvengadam | |
| 5,563,264 A | 10/1996 | Kume | |
| 5,567,439 A | 10/1996 | Myers | |
| 5,576,014 A | 11/1996 | Mizumoto | |
| 5,587,172 A | 12/1996 | Cherukuri | |
| 5,587,180 A | 12/1996 | Allen | |
| 5,591,456 A | 1/1997 | Franson | |
| 5,593,971 A | 1/1997 | Tschollar | |
| 5,595,761 A | 1/1997 | Allen | |
| 5,607,697 A | 3/1997 | Alkire | |
| 5,612,353 A | 3/1997 | Ewing | |
| 5,612,367 A | 3/1997 | Timko | |
| 5,612,378 A | 3/1997 | Tianbao | |
| 5,618,707 A | 4/1997 | Homann | |
| 5,622,719 A | 4/1997 | Myers | |
| 5,622,985 A | 4/1997 | Olukotun | |
| 5,624,920 A | 4/1997 | McKittrick | |
| 5,627,176 A | 5/1997 | Kirkup | |
| 5,631,023 A | 5/1997 | Kearney | |
| 5,631,365 A | 5/1997 | Rosenblum | |
| 5,633,246 A | 5/1997 | McKittrick | |
| 5,635,210 A | 6/1997 | Allen | |
| 5,639,475 A | 6/1997 | Bettman | |
| 5,639,739 A | 6/1997 | Dominguez | |
| 5,656,624 A | 8/1997 | Vaccaro | |
| 5,661,145 A | 8/1997 | Davis | |
| 5,674,893 A | 10/1997 | Behounek | |
| 5,688,785 A | 11/1997 | Vaccaro | |
| 5,688,787 A | 11/1997 | Burnett | |
| 5,688,990 A | 11/1997 | Shankar | |
| 5,691,375 A | 11/1997 | Behounek | |
| 5,698,527 A | 12/1997 | Kim | |
| 5,698,548 A | 12/1997 | Dugar | |
| 5,703,188 A | 12/1997 | Mandeville | |
| 5,703,234 A | 12/1997 | Iwasaki | |
| 5,709,886 A | 1/1998 | Bettman | |
| 5,718,388 A | 2/1998 | Czekai | |
| 5,728,827 A | 3/1998 | Thiruvengadam | |
| 5,734,077 A | 3/1998 | Regnier | |
| 5,739,321 A | 4/1998 | Wu | |
| 5,744,467 A | 4/1998 | McKittrick | |
| 5,747,001 A | 5/1998 | Wiedmann | |
| 5,753,254 A | 5/1998 | Khan | |
| 5,756,470 A | 5/1998 | Yumibe | |
| 5,759,865 A | 6/1998 | Bruns | |
| 5,767,115 A | 6/1998 | Rosenblum | |
| 5,776,491 A | 7/1998 | Allen | |
| 5,807,576 A | 9/1998 | Allen | |
| 5,807,577 A | 9/1998 | Ouali | |
| 5,807,578 A | 9/1998 | Acosta-Cuello | |
| 5,807,834 A | 9/1998 | Morehouse | |
| 5,808,056 A | 9/1998 | Amato | |
| 5,817,806 A | 10/1998 | Rossi | |
| 5,827,536 A | 10/1998 | Laruelle | |
| 5,827,541 A | 10/1998 | Yarwood | |
| 5,831,091 A | 11/1998 | Ohmizu | |
| 5,843,984 A | 12/1998 | Clay | |
| 5,846,966 A | 12/1998 | Rosenblum | |
| 5,847,008 A | 12/1998 | Doebber | |
| 5,847,115 A | 12/1998 | Iwasaki | |
| 5,851,553 A | 12/1998 | Myers | |
| 5,856,473 A | 1/1999 | Shankar | |
| 5,858,409 A | 1/1999 | Karetny | |
| 5,859,051 A | 1/1999 | Adams | |
| 5,862,999 A | 1/1999 | Czekai | |
| 5,866,163 A | 2/1999 | Myers | |
| 5,869,098 A | 2/1999 | Misra | |
| 5,871,781 A | 2/1999 | Myers | |
| 5,880,148 A | 3/1999 | Edgar | |
| 5,883,109 A | 3/1999 | Gregg | |
| 5,886,171 A | 3/1999 | Wu | |
| 5,919,672 A | 7/1999 | Homann | |
| 5,925,333 A | 7/1999 | Krieger | |
| 5,952,003 A | 9/1999 | Guentensberger | |
| 5,952,321 A | 9/1999 | Doherty | |
| 5,959,123 A | 9/1999 | Singh | |
| 5,972,389 A | 10/1999 | Shell | |
| 5,976,570 A | 11/1999 | Greaves | |

| | | | | | | |
|---|---|---|---|---|---|---|
| 5,985,936 | A | 11/1999 | Novak | | FOREIGN PATENT DOCUMENTS | |
| 5,990,102 | A | 11/1999 | Hickey | | | |
| 5,994,554 | A | 11/1999 | Kliewer | DE | 2521113 A | 3/1976 |
| 5,998,441 | A | 12/1999 | Palkowitz | EP | 0002151 A1 B1 | 5/1979 |
| 6,008,237 | A | 12/1999 | Sahoo | EP | 0010299 B1 | 2/1984 |
| 6,027,747 | A | 2/2000 | Terracol | EP | 0179559 A2 | 4/1986 |
| 6,028,109 | A | 2/2000 | Wilson | EP | 0199630 A1 | 10/1986 |
| 6,030,990 | A | 2/2000 | Maeda et al. | EP | 0264231 A1 | 4/1988 |
| 6,033,656 | A | 3/2000 | Mikami | EP | 0266896 B1 | 5/1988 |
| 6,040,147 | A | 3/2000 | Ridker | EP | 0274873 B1 | 7/1988 |
| 6,043,257 | A | 3/2000 | Dominguez | EP | 0288973 B1 | 11/1988 |
| 6,056,975 | A | 5/2000 | Mitra | EP | 0311366 B1 | 4/1989 |
| 6,057,342 | A | 5/2000 | Fevig | EP | 0333268 A1 | 9/1989 |
| 6,063,764 | A | 5/2000 | Creasey | EP | 0337549 A1 | 10/1989 |
| 6,066,653 | A | 5/2000 | Gregg | EP | 0365364 A2 | 4/1990 |
| 6,071,899 | A | 6/2000 | Hickey | EP | 0369686 A1 | 5/1990 |
| 6,074,670 | A | 6/2000 | Stamm | EP | 0375527 A1 | 6/1990 |
| 6,080,767 | A | 6/2000 | Klein | EP | 0199630 B1 | 9/1990 |
| 6,080,778 | A | 6/2000 | Yankner | EP | 0401705 A3 | 12/1990 |
| 6,084,082 | A | 7/2000 | Ravikumar | EP | 0415487 A2 | 3/1991 |
| 6,090,830 | A | 7/2000 | Myers | EP | 0455042 A1 | 11/1991 |
| 6,090,839 | A | 7/2000 | Adams | EP | 0457514 A1 | 11/1991 |
| 6,093,812 | A | 7/2000 | Thiruvengadam | EP | 0461548 A3 | 12/1991 |
| 6,096,883 | A | 8/2000 | Wu | EP | 0462667 A2 | 12/1991 |
| 6,099,865 | A | 8/2000 | Augello | EP | 0475148 A1 | 3/1992 |
| 6,103,705 | A | 8/2000 | Uzan | EP | 0475755 B1 | 3/1992 |
| 6,110,493 | A | 8/2000 | Guentensberger | EP | 048167 A1 | 4/1992 |
| 6,117,429 | A | 9/2000 | Bucci | EP | 0482498 A3 | 4/1992 |
| 6,121,319 | A | 9/2000 | Somers | EP | 0524595 A1 | 1/1993 |
| 6,127,424 | A | 10/2000 | Martin | EP | 0337549 B1 | 10/1995 |
| 6,133,001 | A | 10/2000 | Homann | EP | 0720599 B1 | 7/1996 |
| 6,139,873 | A | 10/2000 | Hughes | EP | 0457514 B1 | 8/1996 |
| 6,140,354 | A | 10/2000 | Dax | EP | 0 753 298 A1 | 1/1997 |
| 6,143,885 | A | 11/2000 | Choi | EP | 0793958 A2 | 9/1997 |
| 6,147,090 | A | 11/2000 | DeNinno | EP | 0814080 A1 | 12/1997 |
| 6,147,109 | A | 11/2000 | Liao | EP | 0904781 A2 | 3/1999 |
| 6,147,250 | A | 11/2000 | Somers | EP | 1 036 563 A1 | 9/2000 |
| 6,159,997 | A | 12/2000 | Tsujita | EP | 1048295 A2 | 11/2000 |
| 6,162,805 | A | 12/2000 | Hefti | FR | 1103113 | 10/1955 |
| 6,166,049 | A | 12/2000 | Smith | FR | 2779347 | 12/1997 |
| 6,174,665 | B1 | 1/2001 | Dullien | GB | 861367 | 2/1961 |
| 6,180,138 | B1 | 1/2001 | Engh | GB | 902658 | 8/1962 |
| 6,180,625 | B1 | 1/2001 | Persson | GB | 1415295 | 11/1975 |
| 6,180,660 | B1 | 1/2001 | Whitney | GB | 2329334 A | 3/1999 |
| 6,191,117 | B1 | 2/2001 | Kozachuk | JP | 136485 | 5/1981 |
| 6,191,159 | B1 | 2/2001 | Pinto | JP | 028057 | 10/1981 |
| 6,200,998 | B1 | 3/2001 | Sahoo | JP | 180212 | 3/1986 |
| 6,207,697 | B1 | 3/2001 | Han | JP | 121479 | 12/1986 |
| 6,207,699 | B1 | 3/2001 | Rothman | JP | 61280295 A | 12/1986 |
| 6,207,822 | B1 | 3/2001 | Thiruvengadam | JP | 219681 | 4/1987 |
| 6,214,831 | B1 | 4/2001 | Yokoo | JP | 63017859 A | 1/1988 |
| 6,235,706 | B1 | 5/2001 | Gould | JP | 91068020 | 10/1991 |
| 6,242,605 | B1 | 6/2001 | Raveendranath | JP | 4054182 A | 2/1992 |
| 6,245,743 | B1 | 6/2001 | Marlowe | JP | 4266869 A | 9/1992 |
| 6,248,781 | B1 | 6/2001 | Jeppesen | JP | 4356195 A | 12/1992 |
| 6,251,852 | B1 | 6/2001 | Gould | JP | 4356495 | 12/1992 |
| 6,262,042 | B1 | 7/2001 | Cook | JP | 5058993 A | 3/1993 |
| 6,262,047 | B1 | 7/2001 | Zhu | JP | 5194209 A | 8/1993 |
| 6,262,098 | B1 | 7/2001 | Huebner | JP | 5239020 A | 9/1993 |
| 6,277,584 | B1 | 8/2001 | Chu | JP | 94047573 | 6/1994 |
| 6,316,029 | B1 | 11/2001 | Jain | JP | 95051558 B2 | 6/1995 |
| RE37,721 | E | 5/2002 | Rosenblum | WO | WO 82/01649 | 5/1982 |
| 2001/0028895 | A1 | 10/2001 | Bisgaier | WO | WO 87/04429 | 7/1987 |
| 2002/0006919 | A1 | 1/2002 | Thosar | WO | WO 88/04656 | 6/1988 |
| 2002/0039774 | A1 | 4/2002 | Kramer et al. | WO | WO 88/05296 | 7/1988 |
| 2002/0128252 | A1 | 9/2002 | Glombik et al. | WO | WO 91/03249 | 3/1991 |
| 2002/0128253 | A1 | 9/2002 | Glombik et al. | WO | WO 92/13837 | 8/1992 |
| 2002/0132855 | A1 | 9/2002 | Nelson et al. | WO | WO 93/02048 | 2/1993 |
| 2002/0137689 | A1 | 9/2002 | Glombik et al. | WO | WO 93/07167 | 4/1993 |
| 2003/0153541 | A1 | 8/2003 | Dudley et al. | WO | WO 93/11150 | 6/1993 |
| | | | | WO | WO 94/00480 | 1/1994 |
| | | | | WO | WO 94/14433 | 7/1994 |

| | | |
|---|---|---|
| WO | WO 94/17038 | 8/1994 |
| WO | WO 94/20535 | 9/1994 |
| WO | WO 94/26738 | 11/1994 |
| WO | WO 95/04533 | 2/1995 |
| WO | WO 95/06470 | 3/1995 |
| WO | WO 95/08532 | 3/1995 |
| WO | WO 95/18143 | 7/1995 |
| WO | WO 95/26334 | 10/1995 |
| WO | WO 95/28919 | 11/1995 |
| WO | WO 95/35277 | 12/1995 |
| WO | WO 96/00288 | 1/1996 |
| WO | WO 96/09827 | 4/1996 |
| WO | WO 96/16037 | 5/1996 |
| WO | WO96/19450 | 6/1996 |
| WO | WO 96/19987 | 7/1996 |
| WO | WO 96/40255 | 12/1996 |
| WO | WO 97/16455 | 5/1997 |
| WO | WO 97/18304 | 5/1997 |
| WO | WO 97/25042 | 7/1997 |
| WO | WO 97/28149 | 8/1997 |
| WO | WO 97/31907 | 9/1997 |
| WO | WO 97/35576 | 10/1997 |
| WO | WO 97/46238 | 12/1997 |
| WO | WO 98/01100 | 1/1998 |
| WO | WO 98/05331 | 2/1998 |
| WO | WO 98/14179 | 4/1998 |
| WO | WO 98/31360 | 7/1998 |
| WO | WO 98/31361 | 7/1998 |
| WO | WO 98/31366 | 7/1998 |
| WO | WO 98/43081 | 10/1998 |
| WO | WO 98/46215 | 10/1998 |
| WO | WO 98/47518 | 10/1998 |
| WO | WO 98/57652 | 12/1998 |
| WO | WO 99/06035 | 2/1999 |
| WO | WO 99/06046 | 2/1999 |
| WO | WO 99/08501 | 2/1999 |
| WO | WO 99/09967 | 3/1999 |
| WO | WO 99/11260 | 3/1999 |
| WO | WO 99/12534 | 3/1999 |
| WO | WO 99/04815 | 4/1999 |
| WO | WO 99/15159 | 4/1999 |
| WO | WO 99/15520 | 4/1999 |
| WO | WO 99/18072 | 4/1999 |
| WO | WO 99/20275 | 4/1999 |
| WO | WO 99/20614 | 4/1999 |
| WO | WO 99/22728 | 5/1999 |
| WO | WO 99/29300 | 6/1999 |
| WO | WO 99/38498 | 8/1999 |
| WO | WO 99/38845 | 8/1999 |
| WO | WO 99/38850 | 8/1999 |
| WO | WO 99/46232 | 9/1999 |
| WO | WO 99/47123 | 9/1999 |
| WO | WO 99/48488 | 9/1999 |
| WO | WO 99/66929 | 12/1999 |
| WO | WO 99/66930 | 12/1999 |
| WO | WO 00/04011 | 1/2000 |
| WO | WO 00/07617 | 2/2000 |
| WO | WO 00/16749 | 3/2000 |
| WO | WO 00/18395 | 4/2000 |
| WO | WO 00/20623 | 4/2000 |
| WO | WO 00/23415 | 4/2000 |
| WO | WO 00/23416 | 4/2000 |
| WO | WO 00/23425 | 4/2000 |
| WO | WO 00/23445 | 4/2000 |
| WO | WO 00/23451 | 4/2000 |
| WO | WO 00/28981 | 5/2000 |
| WO | WO 00/31548 | 6/2000 |
| WO | WO 00/32189 | 6/2000 |
| WO | WO 00/34240 | 6/2000 |
| WO | WO 00/37057 | 6/2000 |
| WO | WO 00/37078 | 6/2000 |
| WO | WO 00/38721 | 7/2000 |
| WO | WO 00/38722 | 7/2000 |
| WO | WO 00/38723 | 7/2000 |
| WO | WO 00/38724 | 7/2000 |
| WO | WO 01/14351 | 3/2001 |
| WO | WO 01/34148 | 5/2001 |
| WO | WO 01/60807 | 8/2001 |
| WO | WO 01/96347 | 12/2001 |
| WO | WO 02/08188 | 1/2002 |
| WO | WO 02/26729 | 4/2002 |
| WO | WO02/26729 | 4/2002 |
| WO | WO 02/50027 | 6/2002 |
| WO | WO 02/50060 | 6/2002 |
| WO | WO 02/50068 | 6/2002 |
| WO | WO02/64094 | 8/2002 |
| WO | WO 02/064094 | 8/2002 |
| WO | WO02/081454 | 10/2002 |
| WO | WO 03/018024 | 3/2003 |
| WO | WO 03/018059 | 3/2003 |
| WO | WO 03/039542 | 5/2003 |
| WO | WO 03/074101 | 9/2003 |
| WO | WO 03/088962 | 10/2003 |

OTHER PUBLICATIONS

Sorbera et al., Netoglitazone, *Drugs of the Future*, 2002, 27(2): 132–139.

Michel Farnier, Nouvelles approches médicamenteuses dans le traitement des dyslipidémies, *MT Endocrinologie*, 2002, 4:252–259.

Berger et al., Physiological and Therapeutic Roles of Peroxisome Proliferator–Activated Receptors, *Diabetes Technology & Therapeutics*, 2002, 4:163–174.

U.S. Appl. No. 10/166,942, filed Jun. 11, 2002, Anima Ghosal et al.

Stuart B. Rosenblum et al., Discovery of 1–(4–Fluorophenyl)–(3R)–[3–(fluorophenyl)–(3S)–hydroxypropyl]–(4S)–(4–hydroxyphenyl)–2–azetidinone (SCH 58235): A Designed, Potent, Orally Active Inhibitor of Cholesterol Absorption, *J. Med. Chem.* 41:973–980 (1998).

Remington's Pharmaceutical Sciences, 18th ed. 1990 p. 1319, 1633–1647.

Baker S G et al., Treatment of homozygous familial hypercholesterolaemia with probucol, *South African Medical Journal* (1982).

R. Milanese et al., Xantomi E Ipercolesterolemia: Prevalenza, Diagnosi e Terpia, *Chron. Derm.* 455–61 (1990).

Thompson, G.R. et al., "Novel lipid–regulating drugs" *Expert Opinion on Investigational Drugs* 9(11):2619–2628 (2000), XP008011782 abstract; figure 8.

Kosoglou, T. et al., "Coadministration of ezetimibe and fenofibrate leads to favorable effects on Apo CII and LDL subfractions" *Atherosclerosis* 2:89 (2001), XP001132089 abstract.

Exhibit A: SCH 58235 Micronized (ezetimibe), Drug Formulation Development Summary, 4/97.

Exhibit B: SCH 58235 (ezetimibe), Drug Formulation Development Summary, 4/97.

Exhibit C: SCH 58235 (ezetimibe), Drug Formulation Development Summary, 4/97.

Exhibit D: SCH 58235 (ezetimibe), Drug Formulation Development Summary, 10/97.

Exhibit E: SCH 58235 (ezetimibe), Drug Formulation Development Summary, 10/97.

Exhibit F: SCH 58235 (ezetimibe), Drug Formulation Development Summary, 11/98.

Exhibit G: SCH 58235 (ezetimibe), Drug Formulation Development Summary, 11/98.

Exhibit H: SCH 58235 (ezetimibe), Drug Formulation Development Summary, 11/98.

Exhibit 1: Master Sheet for the SCH 58235 and Lovastatin Research Study, *Schering–Plough Research Institute* (Protocol No. C906–411), p. 1576–1585.

Exhibit 2: Medical Research Study #1055/97, SCH 58235: Bioavailability of Single Oral Doses of Two Prototype Tablet Formulations and the Reference Capsule Formulation of SCH 58235 in Normal Male Volunteers: A Four Way Crossover Study #C97–221–01, Informed Consent, *Peninsular Testing Corporation*, p. 106–112.

Exhibit 3: Consent Form to Participate in a Research Study, "A Phase II Double Blind Dose Response Investigation of Efficacy and Safety of Four Doses of SCH 58235 Compared to Placebo in Subjects with Primary Hypercholesterolemia," *Schering–Plough Research Institute* (Protocol No. C98–010), p. 1558–1566.

Exhibit 4: Medical Research Study #1096/99, SCH 58235: Pharmacokinetic Pharmacodynamic Drug Interaction Study with Digoxin in Healthy Volunteers #C98–114, Informed Consent, *Peninsular Testing Corporation*, p. 124–130.

Exhibit 5: Informed Consent, "SCH 58235: Assessemnt of Multiple–Dose Drug Interaction Between 58235 and Gemfibrozil in Healthy Volunteers," *Schering–Plough Research Institute*, p. 1–8.

Gilber R. Thompson et al., Novel lipid–regulating drugs, Ashley Publications Ltd. ISSN 1354–3784, 2000, pp. 2619–2628.

Belamarich P.F. et al., Response to diet and cholestyramine in a patient with sitosterolemia, Pediatrics, ISSN 0031–4005, Dec. 1990.

Salen G. et al., Lethal atherosclerosis associated with abnormal plasma and tissue sterol composition in sitosterolemia with xanthomatosis, Journal of lipid research, ISSN 0022–2275, Sep. 1985.

Luis Gruberg, MD, Infammatory Markers in Acute Coronary Syndromes: C–reactive Protein (CRP) and Chlamydia, American Heart Association Scientific Sessions 2000.

"Study showed ezetimibe significantly reduced levels of LDL cholesterol or "bad" cholesterol in patients" *Schering Press Release* 1–3 (2001).

Kosoglou et al., "Pharmacodynamic interaction between fenofibrate and the cholesterol absorption inhibitor ezetimibe" *Atheroscelerosis* (2):3(2001).

Davis et al., "The Synergistic Hypocholesterolemic Activity of the Potent Cholesterol Absorption Inhibitor, Ezetimibe, in Combination with 3–Hydroxy–3–Methylglutaryl Coenzyme A Reductase Inhibitors in Dogs" *Metabolism* 50(10):1234–1241(2001).

\* cited by examiner

STEROL ABSORPTION INHIBITOR COMPOSITIONS

CROSS-REFERENCE TO RELATED APPLICATION

This application is a division of U.S. patent application Ser. No. 10/057,323, filed Jan. 25, 2002, and claims the benefit of priority from U.S. Provisional Patent Application Ser. No. 60/264,396 filed Jan. 26, 2001 and U.S. Provisional Patent Application Ser. No. 60/323,839 filed Sep. 21, 2001, each incorporated herein by reference.

FIELD OF THE INVENTION

The present invention relates to compositions and therapeutic combinations comprising peroxisome proliferator-activated receptor (PPAR) activator(s) and certain sterol absorption inhibitor(s) for treating vascular and lipidemic conditions such as are associated with atherosclerosis, hypercholesterolemia and other vascular conditions in mammals.

BACKGROUND OF THE INVENTION

Atherosclerotic coronary heart disease (CHD) represents the major cause for death and vascular morbidity in the western world. Risk factors for atherosclerotic coronary heart disease include hypertension, diabetes mellitus, family history, male gender, cigarette smoke and serum cholesterol. A total cholesterol level in excess of 225–250 mg/dl is associated with significant elevation of risk of CHD.

Cholesteryl esters are a major component of atherosclerotic lesions and the major storage form of cholesterol in arterial wall cells. Formation of cholesteryl esters is also a step in the intestinal absorption of dietary cholesterol. Thus, inhibition of cholesteryl ester formation and reduction of serum cholesterol can inhibit the progression of atherosclerotic lesion formation, decrease the accumulation of cholesteryl esters in the arterial wall, and block the intestinal absorption of dietary cholesterol.

The regulation of whole-body cholesterol homeostasis in mammals and animals involves the regulation of dietary cholesterol and modulation of cholesterol biosynthesis, bile acid biosynthesis and the catabolism of the cholesterol-containing plasma lipoproteins. The liver is the major organ responsible for cholesterol biosynthesis and catabolism and, for this reason, it is a prime determinant of plasma cholesterol levels. The liver is the site of synthesis and secretion of very low density lipoproteins (VLDL) which are subsequently metabolized to low density lipoproteins (LDL) in the circulation. LDL are the predominant cholesterol-carrying lipoproteins in the plasma and an increase in their concentration is correlated with increased atherosclerosis. When intestinal cholesterol absorption is reduced, by whatever means, less cholesterol is delivered to the liver. The consequence of this action is decreased hepatic lipoprotein (VLDL) production and an increase in the hepatic clearance of plasma cholesterol, mostly as LDL. Thus, the net effect of inhibiting intestinal cholesterol absorption is a decrease in plasma cholesterol levels.

Fibric acid derivatives ("fibrates"), such as fenofibrate, gemfibrozil and clofibrate, have been used to lower triglycerides, moderately lower LDL levels and increase HDL levels. Fibric acid derivatives are also known to be peroxisome proliferator-activated receptor alpha activators.

U.S. Pat. Nos. 5,767,115, 5,624,920, 5,668,990, 5,656,624 and 5,688,787, respectively, disclose hydroxy-substituted azetidinone compounds and substituted, β-lactam compounds useful for lowering cholesterol and/or in inhibiting the formation of cholesterol-containing lesions in mammalian arterial walls. U.S. Pat. Nos. 5,846,966 and 5,661,145, respectively, disclose hydroxy-substituted azetidinone compounds or substituted β-lactam compounds in combination with HMG CoA reductase inhibitors for preventing or treating atherosclerosis and reducing plasma cholesterol levels.

PCT Patent Application No. WO 00/38725 discloses cardiovascular therapeutic combinations including an ileal bile acid transport inhibitor or cholesteryl ester transport protein inhibitor in combination with a fibric acid derivative, nicotinic acid derivative, microsomal triglyceride transfer protein inhibitor, cholesterol absorption antagonist, phytosterol, stanol, antihypertensive agent or bile acid sequestrant.

U.S. Pat. No. 5,698,527 discloses ergostanone derivatives substituted with disaccharides as cholesterol absorption inhibitors, employed alone or in combination with certain other cholesterol lowering agents, which are useful in the treatment of hypercholesterolemia and related disorders.

Despite recent improvements in the treatment of vascular disease, there remains a need in the art for improved compositions and treatments for hyperlipidaemia, atherosclerosis and other vascular conditions.

SUMMARY OF THE INVENTION

In one embodiment, the present invention provides a composition comprising: (a) at least one peroxisome proliferator-activated receptor activator; and (b) at least one sterol absorption inhibitor represented by Formula (I):

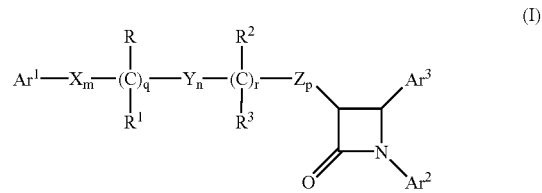

(I)

or isomers thereof, or pharmaceutically acceptable salts or solvates of the compounds of Formula (I) or of the isomers thereof, or prodrugs of the compounds of Formula (I) or of the isomers, salts or solvates thereof, wherein in Formula (I) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —$CH_2$—, —CH(lower alkyl)- and —C(dilower alkyl)-;

R and $R^2$ are independently selected from the group consisting of —$OR^6$, —$O(CO)R^6$, —$O(CO)OR^6$ and —$O(CO)NR^6R^7$;

$R^1$ and $R^3$ are independently selected from the group consisting of hydrogen, lower alkyl and aryl;

q is 0 or 1;

r is 0 or 1;

m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1–5 substituents independently selected from the group consisting of lower alkyl, —OR, —$O(CO)R^6$, —$O(CO)OR^6$, —$O(CH_2)_{1-5}OR^6$, —$O(CO)NR^6R^7$, —NR⁶R⁷, —NR⁶(CO)R⁷, —NR⁶(CO)OR⁹, —NR⁶(CO)NR⁷R⁸, —NR⁶SO₂R⁹, —COOR⁶, —CONR₆R₇, —COR⁶, SO₂NR⁶R⁷, S(O)₀₋₂R⁹, —O(CH₂)₁₋₁₀—COOR⁶, —O(CH₂)₁₋₁₀CONR⁶R⁷, -(lower alkylene)COOR⁶, —CH=CH—COOR⁶, —CF₃, —CN, —NO₂ and halogen;

R⁵ is 1–5 substituents independently selected from the group consisting of —OR⁶, —O(CO)R⁶, —O(CO)OR⁹, —O(CH₂)₁₋₅OR⁶, —O(CO)NR⁶R⁷, —NR⁶(CO)R⁷, —NR⁶(CO)OR⁹, —NR⁶(CO)NR⁷R⁸, —NR⁶SO₂R, —COOR⁶, —CONR⁶R⁷, —COR⁶, —SO₂NR⁶R⁷, S(O)₀₋₂R⁹, —O(CH₂)₁₋₁₀—COOR⁶, —O(CH₂)₁₋₁₀CONR⁶R⁷, -(lower alkylene)COOR⁶ and —CH=CH—COOR⁶;

R⁶, R⁷ and R⁸ are independently selected from the group consisting of hydrogen, lower alkyl, aryl and aryl-substituted lower alkyl; and R⁹ is lower alkyl, aryl or aryl-substituted lower alkyl.

In another embodiment, there is provided a composition comprising: (a) at least one fibric acid derivative; and (b) a compound represented by Formula (II) below:

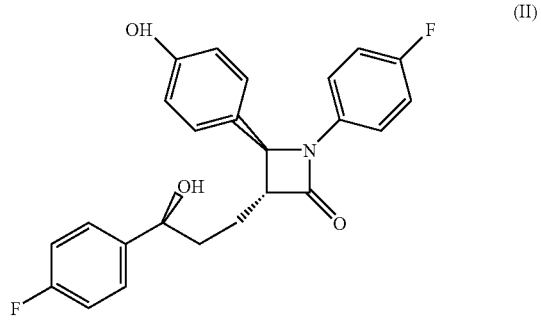

(II)

or pharmaceutically acceptable salt or solvate thereof, or prodrug of the compound of Formula (II) or of the salt or solvate thereof.

In another embodiment, the present invention provides a composition comprising: (a) at least one peroxisome proliferator-activated receptor activator; and (b) at least one sterol absorption inhibitor represented by Formula (III):

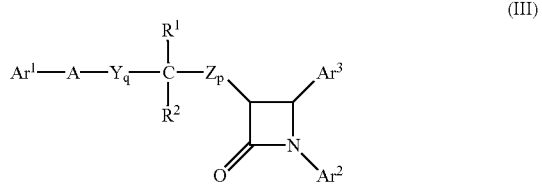

(III)

or isomers thereof, or pharmaceutically acceptable salts or solvates of the compounds of Formula (III) or of the isomers thereof, or prodrugs of the compounds of Formula (III) or of the isomers, salts or solvates thereof, wherein, in Formula (III) above:

Ar¹ is R³-substituted aryl; Ar² is R⁴-substituted aryl; Ar³ is R⁵-substituted aryl;

Y and Z are independently selected from the group consisting of —CH₂—, —CH(lower alkyl)- and —C(dilower alkyl)-;

A is selected from —O—, —S—, —S(O)— or —S(O)₂—;

R¹ is selected from the group consisting of —OR, —O(CO)R, —O(CO)OR and —O(CO)NR⁶R⁷; R² is selected from the group consisting of hydrogen, lower alkyl and aryl; or R¹ and R² together are =O;

q is 1, 2 or 3;

p is 0, 1, 2, 3 or 4;

R⁵ is 1–3 substituents independently selected from the group consisting of —OR⁶, —O(CO)R⁶, —O(CO)OR⁹, —O(CH₂)₁₋₅OR⁹, —O(CO)NR⁶R⁷, —NR⁶R⁷, —NR⁶(CO)R⁷, —NR⁶(CO)OR⁹, —NR⁶(CO)NR⁷R⁸, —NR⁶SO₂-lower alkyl, —NR⁶SO₂-aryl, —CONR⁶R⁷, —COR⁶, —SO₂NR⁶R, S(O)₀₋₂-alkyl, S(O)₀₋₂-aryl, —O(CH₂)₁₋₁₀—COOR⁶, —O(CH₂)₁₋₁₀CONR⁶R⁷, o-halogeno, m-halogeno, o-lower alkyl, m-lower alkyl, -(lower alkylene)-COOR⁶, and —CH=CH—COOR⁶;

R³ and R⁴ are independently 1–3 substituents independently selected from the group consisting of R⁵, hydrogen, p-lower alkyl, aryl, —NO₂, —CF₃ and p-halogeno;

R⁶, R⁷ and R⁸ are independently selected from the group consisting of hydrogen, lower alkyl, aryl and aryl-substituted lower alkyl; and R⁹ is lower alkyl, aryl or aryl-substituted lower alkyl.

In another embodiment, the present invention provides a composition comprising: (a) at least one peroxisome proliferator-activated receptor activator; and (b) at least one sterol absorption inhibitor represented by Formula (IV):

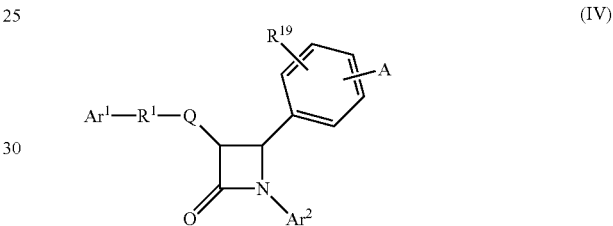

(IV)

or isomers thereof, or pharmaceutically acceptable salts or solvates of the compounds of Formula (IV) or of the isomers thereof, or prodrugs of the compounds of Formula (IV) or of the isomers, salts or solvates thereof, wherein, in Formula (IV) above:

A is selected from the group consisting of R²-substituted heterocycloalkyl, R²-substituted heteroaryl, R²-substituted benzofused heterocycloalkyl, and R²-substituted benzofused heteroaryl;

Ar¹ is aryl or R³-substituted aryl;

Ar² is aryl or R⁴-substituted aryl;

Q is a bond or, with the 3-position ring carbon of the azetidinone, forms the spiro group

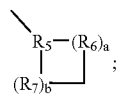

and

R¹ is selected from the group consisting of:

—(CH₂)_q—, wherein q is 2–6, provided that when Q forms a spiro ring, q can also be zero or 1;

—(CH₂)_e—G—(CH₂)_r—, wherein G is —O—, —C(O)—, phenylene, —NR⁸— or —S(O)0-2—, e is 0–5 and r is 0–5, provided that the sum of e and r is 1–6;

—(C₂-C₆ alkenylene)-; and

—(CH₂)_f—V—(CH₂)_g—, wherein V is C₃–C₆ cycloalkylene, f is 1–5 and g is 0–5, provided that the sum of f and g is 1–6;

R⁵ is selected from:

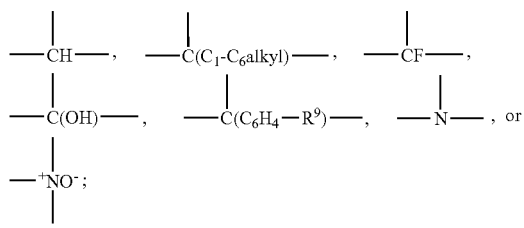

R⁶ and R⁷ are independently selected from the group consisting of —CH₂—, —CH(C₁–C₆ alkyl)-, —C(di-(C₁–C₆)alkyl), —CH=CH— and —C(C₁–C₆ alkyl)=CH—; or R⁵ together with an adjacent R⁶, or R⁵ together with an adjacent R⁷, form a —CH=CH— or a —CH=C(C₁–C₆ alkyl)-group;

a and b are independently 0, 1, 2 or 3, provided both are not zero; provided that when R⁶ is —CH=CH— or —C(C₁–C₆ alkyl)=CH—, a is 1; provided that when R⁷ is —CH=CH— or —C(C₁–C₆ alkyl)=CH—, b is 1; provided that when a is 2 or 3, the R⁶'s can be the same or different; and provided that when b is 2 or 3, the R⁷'s can be the same or different;

and when Q is a bond, R¹ also can be selected from:

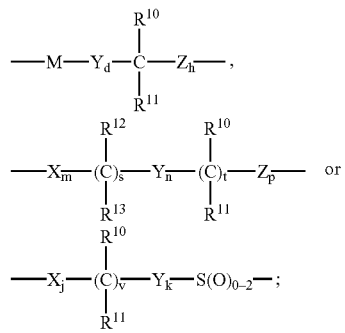

where M is —O—, —S—, —S(O)— or —S(O)₂—;

X, Y and Z are independently selected from the group consisting of —CH₂—, —CH(C₁–C₆alkyl)- and —C(di-(C₁–C₆) alkyl);

R¹⁰ and R¹² are independently selected from the group consisting of —OR¹⁴, —O(CO)R¹⁴, —O(CO)OR¹⁶ and —O(CO)NR¹⁴R¹⁵;

R¹¹ and R¹³ are independently selected from the group consisting of hydrogen, (C₁–C₆)alkyl and aryl; or R¹⁰ and R¹¹ together are =O, or R¹² and R¹³ together are =O;

d is 1, 2 or 3;

h is 0, 1, 2, 3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

R² is 1–3 substituents on the ring carbon atoms selected from the group consisting of hydrogen, (C₁–C₁₀)alkyl, (C₂–C₁₀)alkenyl, (C₂–C₁₀)alkynyl, (C₃–C₆)cycloalkyl, (C₃–C₆)cycloalkenyl, R¹⁷-substituted aryl, R¹⁷-substituted benzyl, R¹⁷-substituted benzyloxy, R¹⁷-substituted aryloxy, halogeno, —NR¹⁴R¹⁵, NR¹⁴R¹⁵(C₁–C₆ alkylene)-, NR¹⁴R¹⁵C(O)(C₁–C₆ alkylene)-, —NHC(O)R¹⁶, OH, C₁–C₆ alkoxy, —OC(O)R, —COR¹⁴, hydroxy(C₁–C₆)alkyl, (C₁–C₆)alkoxy(C₁–C₆)alkyl, NO₂, —S(O)₀₋₂R¹⁶, —SO₂N¹⁴R¹⁵ and —(C₁–C₆ alkylene)COOR¹⁴; when R² is a substituent on a heterocycloalkyl ring, R² is as defined, or is =O or

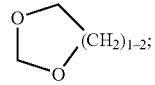

and, where R² is a substituent on a substitutable ring nitrogen, it is hydrogen, (C₁–C₆)alkyl, aryl, (C₁–C₆)alkoxy, aryloxy, (C₁–C₆)alkylcarbonyl, arylcarbonyl, hydroxy, —(CH₂)₁₋₆CONR¹⁸R¹⁸,

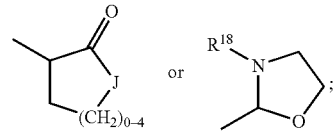

wherein J is —O—, —NH—, —NR¹⁸— or —CH₂—;

R³ and R⁴ are independently selected from the group consisting of 1–3 substituents independently selected from the group consisting of (C₁–C₆)alkyl, —OR¹⁴, —O(CO)R¹⁴, —O(CO)OR¹⁶, —O(CH₂)₁₋₅OR¹⁴, —O(CO)NR¹⁴R¹⁵, —NR¹⁴R¹⁵, —NR¹⁴(CO)R¹⁵, —NR¹⁴(CO)OR¹⁶, —NR¹⁴(CO)NR¹⁵R¹⁹, —NR¹⁴SO₂R¹⁶, —COOR¹⁴, —CONR¹⁴R¹⁵, —COR¹⁴, —SO₂NR¹⁴R¹⁵, S(O)₀₋₂R¹⁶, —O(CH₂)₁₋₁₀—COOR¹⁴, —O(CH₂)₁₋₁₀CONR¹⁴R¹⁵, —(C₁–C₆ alkylene)-COOR¹⁴, —CH=CH—COOR¹⁴, —CF₃, —CN, —NO₂ and halogen;

R⁸ is hydrogen, (C₁–C₆)alkyl, aryl (C₁–C₆)alkyl, —C(O)R¹⁴ or —COOR¹⁴;

R⁹ and R¹⁷ are independently 1–3 groups independently selected from the group consisting of hydrogen, (C₁–C₆)alkyl, (C₁–C₆)alkoxy, —COOH, NO₂, —NR¹⁴R¹⁵, OH and halogeno;

R¹⁴ and R¹⁵ are independently selected from the group consisting of hydrogen, (C₁–C₆)alkyl, aryl and aryl-substituted (C₁–C₆)alkyl;

R¹⁶ is (C₁–C₆)alkyl, aryl or R¹⁷-substituted aryl;

R¹⁸ is hydrogen or (C₁–C₆)alkyl; and

R¹⁹ is hydrogen, hydroxy or (C₁–C₆)alkoxy.

In another embodiment, the present invention provides a composition comprising: (a) at least one peroxisome proliferator-activated receptor activator; and (b) at least one sterol absorption inhibitor represented by Formula (V):

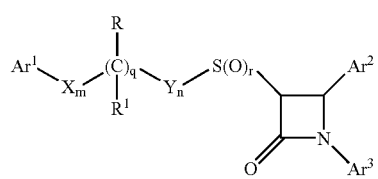

or isomers thereof, or pharmaceutically acceptable salts or solvates of the compounds of Formula (V) or of the isomers thereof, or prodrugs of the compounds of Formula (V) or of the isomers, salts or solvates thereof, wherein, in Formula (V) above:

Ar¹ is aryl, R¹⁰-substituted aryl or heteroaryl;

Ar² is aryl or R⁴-substituted aryl;

Ar³ is aryl or R⁵-substituted aryl;

X and Y are independently selected from the group consisting of —CH₂—, —CH(lower alkyl)- and —C(dilower alkyl)-;

R is —OR⁶, —O(CO)R⁶, —O(CO)OR⁹ or —O(CO)NR⁶R⁷; R¹ is hydrogen, lower alkyl or aryl; or R and R¹ together are =O;

q is 0 or 1;

r is 0, 1 or 2;

m and n are independently 0, 1, 2, 3, 4 or 5; provided that the sum of m, n and q is 1, 2, 3, 4 or 5;

R⁴ is 1–5 substituents independently selected from the group consisting of lower alkyl, —OR⁶, —O(CO)R⁶, —O(CO)OR⁹, —O(CH₂)₁₋₅OR⁶, —O(CO)NR⁶R⁷, —NR⁶R⁷, —NR⁶(CO)R⁷, —NR⁶(CO)OR⁹, —NR⁶(CO)NR⁷R⁸, —NR⁶SO₂R⁹, —COOR⁶, —CONR⁶R⁷, —COR⁶, —SO₂NR⁶R⁷, S(O)₀₋₂R⁹, —O(CH₂)₁₋₁₀—COOR⁶, —O(CH₂)₁₋₁₀CONR⁶R⁷, -(lower alkylene)COOR⁶ and —CH=CH—COOR⁶;

R⁵ is 1–5 substituents independently selected from the group consisting of —OR⁶, —O(CO)R⁶, —O(CO)OR⁹, —O(CH₂)₁₋₅OR⁶, —O(CO)NR⁶R⁷, —NR⁶R⁷, —NR⁶(CO)R⁷, —NR⁶(CO)OR⁹, —NR⁶(CO)NR⁷R⁸, —NR⁶SO₂R⁹, —COOR⁶, —CONR⁶R⁷, —COR₆, —SO₂NR⁶R⁷, S(O)₀₋₂R⁹, —O(CH₂)₁₋₁₀—COOR⁶, —O(CH₂)₁₋₁₀CONR⁶R⁷, —CF₃, —CN, —NO₂, halogen, -(lower alkylene)COOR⁶, and —CH=CH—COOR⁶;

R⁶, R⁷ and R⁸ are independently selected from the group consisting of hydrogen, lower alkyl, aryl and aryl-substituted lower alkyl;

R⁹ is lower alkyl, aryl or aryl-substituted lower alkyl; and

R¹⁰ is 1–5 substituents independently selected from the group consisting of lower alkyl, —OR⁶, —O(CO)R⁶, —O(CO)OR⁹, —O(CH₂)₁₋₅OR⁶, —O(CO)NR⁶R⁷, —NR⁶R⁷, —NR⁶(CO)R⁷, —NR⁶(CO)OR⁹, —NR⁶(CO)NR⁷R⁸, —NR⁶SO₂R⁹, —COOR⁶, —CONR⁶R⁷, —COR⁶, —SO₂NR⁶R⁷, —S(O)₀₋₂R⁹, —O(CH₂)₁₋₁₀—COOR⁶, —O(CH₂)₁₋₁₀CONR⁶R⁷, —CF₃, —CN, —NO₂ and halogen.

In another embodiment, the present invention provides a composition comprising: (a) at least one peroxisome proliferator-activated receptor activator; and (b) at least one sterol absorption inhibitor represented by Formula (VI):

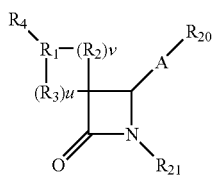

or isomers thereof, or pharmaceutically acceptable salts or solvates of the compounds of Formula (VI) or of the isomers thereof, or prodrugs of the compounds of Formula (VI) or of the isomers, salts or solvates thereof, wherein in Formula (VI) above:

R₁ is

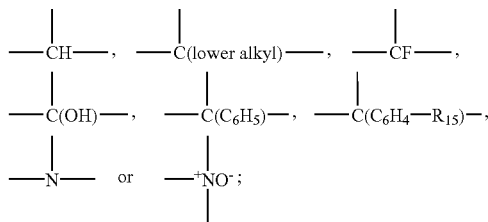

R₂ and R₃ are independently selected from the group consisting of: —CH₂—, —CH(lower alkyl)-, —C(di-lower alkyl)-, —CH=CH— and —C(lower alkyl)=CH—; or R₁ together with an adjacent R₂, or R₁ together with an adjacent R₃, form a —CH=CH— or a —CH=C(lower alkyl)-group;

u and v are independently 0, 1, 2 or 3, provided both are not zero; provided that when R₂ is —CH=CH— or —C(lower alkyl)=CH—, v is 1; provided that when R₃ is —CH=CH— or —C(lower alkyl)=CH—, u is 1; provided that when v is 2 or 3, the R₂'s can be the same or different; and provided that when u is 2 or 3, the R₃'s can be the same or different;

R₄ is selected from B—(CH₂)ₘC(O)—, wherein m is 0, 1, 2, 3, 4 or 5; B—(CH₂)q—, wherein q is 0, 1, 2, 3, 4, 5 or 6; B—(CH₂)ₑ—Z—(CH₂)ᵣ—, wherein Z is —O—, —C(O)—, phenylene, —N(R₈)— or —S(O)₀₋₂—, e is 0, 1, 2, 3, 4 or 5 and r is 0, 1, 2, 3, 4 or 5, provided that the sum of e and r is 0, 1, 2, 3, 4, 5 or 6; B—(C₂–C₆ alkenylene)-; B—(C₄–C₆ alkadienylene)-; B—(CH₂)ₜ—Z—(C₂–C₆ alkenylene)-, wherein Z is as defined above, and wherein t is 0, 1, 2 or 3, provided that the sum of t and the number of carbon atoms in the alkenylene chain is 2, 3, 4, 5 or 6; B—(CH₂)ƒ—V—(CH₂)g—, wherein V is C₃–C₆ cycloalkylene, f is 1, 2, 3, 4 or 5 and g is 0, 1, 2, 3, 4 or 5, provided that the sum of f and g is 1, 2, 3, 4, 5 or 6; B—(CH₂)ₜ—V—(C₂–C₆ alkenylene)- or B—(C₂–C₆ alkenylene)—V—(CH₂)ₜ—, wherein V and t are as defined above, provided that the sum of t and the number of carbon atoms in the alkenylene chain is 2, 3, 4, 5 or 6; B—(CH₂)ₐ—Z—(CH₂)ᵦ—V—(CH₂)d—, wherein Z and V are as defined above and a, b and d are independently 0, 1, 2, 3, 4, 5 or 6, provided that the sum of a, b and d is 0, 1, 2, 3, 4, 5 or 6; or T—(CH₂)ₛ—, wherein T is cycloalkyl of 3–6 carbon atoms and s is 0, 1, 2, 3, 4, 5 or 6; or R₁ and R₄ together form the group

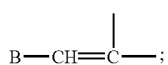

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

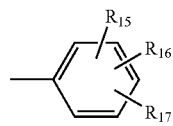

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —CF₃, —OCF₃, benzyl, R₇-benzyl, benzyloxy, R₇-benzyloxy, phenoxy, R₇-phenoxy, dioxolanyl, NO₂, —N(R₈)(R₉), N(R₈)(R₉)-lower alkylene-, N(R₈)(R₉)-lower alkylenyloxy-, OH, halogeno, —CN, —N₃, —NHC(O)OR₁₀, —NHC(O)R₁₀, R₁₁O₂SNH—, (R₁₁O₂S)₂N—, —S(O)₂NH₂, —S(O)₀₋₂R₈, tert-butyldimethyl-silyloxymethyl, —C(O)R₁₂, —COOR₁₉, —CON(R₈)(R₉), —CH=CHC(O)R₁₂, -lower alkylene-C(O)R₁₂, R₁₀C(O)(lower alkylenyloxy)-, N(R₈)(R₉)C(O)(lower alkylenyloxy)- and

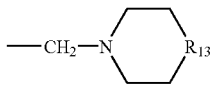

for substitution on ring carbon atoms, and the substituents on the substituted heteroaryl ring nitrogen atoms, when present, are selected from the group consisting of lower alkyl, lower alkoxy, —C(O)OR$_{10}$, —C(O)R$_{10}$, OH, N(R$_8$)(R$_9$)-lower alkylene-, N(R$_8$)(R$_9$)-lower alkylenyloxy, —S(O)$_2$NH$_2$ and 2-(trimethylsilyl)-ethoxymethyl;

R$_7$ is 1–3 groups independently selected from the group consisting of lower alkyl, lower alkoxy, —COOH, NO$_2$, —N(R$_8$)(R$_9$), OH, and halogeno;

R$_8$ and R$_9$ are independently selected from H or lower alkyl;

R$_{10}$ is selected from lower alkyl, phenyl, R$_7$-phenyl, benzyl or R$_7$-benzyl;

R$_{11}$ is selected from OH, lower alkyl, phenyl, benzyl, R$_7$-phenyl or R$_7$-benzyl;

R$_{12}$ is selected from H, OH, alkoxy, phenoxy, benzyloxy,

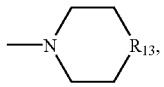

—N(R$_8$)(R$_9$), lower alkyl, phenyl or R$_7$-phenyl;

R$_{13}$ is selected from —O—, —CH$_2$—, —NH—, —N(lower alkyl)- or —NC(O)R$_{19}$;

R$_{15}$, R$_{16}$ and R$_{17}$ are independently selected from the group consisting of H and the groups defined for W; or R$_{15}$ is hydrogen and R$_{16}$ and R$_{17}$, together with adjacent carbon atoms to which they are attached, form a dioxolanyl ring;

R$_{19}$ is H, lower alkyl, phenyl or phenyl lower alkyl; and

R$_{20}$ and R$_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

In another embodiment, the present invention provides a composition comprising: (a) at least one peroxisome proliferator-activated receptor activator; and(b) at least one sterol absorption inhibitor represented by Formula (VII):

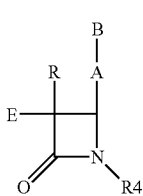

(VII)

or isomers thereof, or pharmaceutically acceptable salts or solvates of the compounds of Formula (VII) or of the isomers thereof, or prodrugs of the compounds of Formula (VII) or of the isomers, salts or solvates thereof, wherein in Formula (VII) above:

A is —CH=CH—, —C≡C— or —(CH$_2$)$_p$— wherein p is 0, 1 or 2;

B is

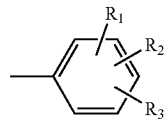

E is C$_{10}$ to C$_{20}$ alkyl or —C(O)—(C$_9$ to C$_{19}$)-alkyl, wherein the alkyl is straight or branched, saturated or containing one or more double bonds;

R is hydrogen, C$_1$–C$_{15}$ alkyl, straight or branched, saturated or containing one or more double bonds, or B—(CH$_2$)$_r$—, wherein r is 0, 1, 2, or 3;

R$_1$, R$_2$, and R$_3$ are independently selected from the group consisting of hydrogen, lower alkyl, lower alkoxy, carboxy, NO$_2$, NH$_2$, OH, halogeno, lower alkylamino, dilower alkylamino, —NHC(O)OR$_5$, R$_6$O$_2$SNH— and —S(O)$_2$NH$_2$;

R$_4$ is

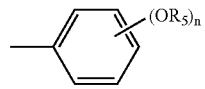

wherein n is 0, 1, 2 or 3;

R$_5$ is lower alkyl; and

R$_6$ is OH, lower alkyl, phenyl, benzyl or substituted phenyl wherein the substituents are 1–3 groups independently selected from the group consisting of lower alkyl, lower alkoxy, carboxy, NO$_2$, NH$_2$, OH, halogeno, lower alkylamino and dilower alkylamino.

In another embodiment, the present invention provides a composition comprising: (a) at least one peroxisome proliferator-activated receptor activator; and (b) at least one sterol absorption inhibitor represented by Formula (VIII):

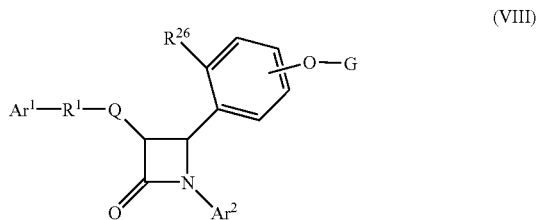

(VIII)

or isomers thereof, or pharmaceutically acceptable salts or solvates of the compounds of Formula (VIII) or of the isomers thereof, or prodrugs of the compounds of Formula (VIII) or of the isomers, salts or solvates thereof, wherein, in Formula (VIII) above, R$^{26}$ is H or OG$^1$;

G and G$^1$ are independently selected from the group consisting of

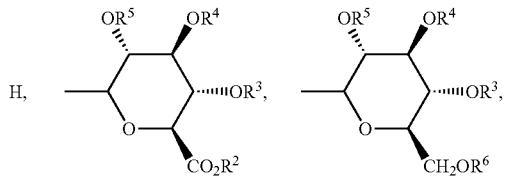

-continued

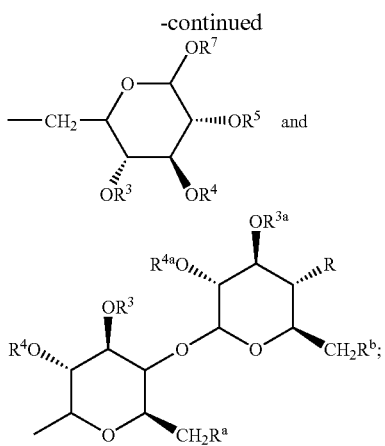

provided that when $R^{26}$ is H or OH, G is not H;

$R$, $R^a$ and $R^b$ are independently selected from the group consisting of H, —OH, halogeno, —$NH_2$, azido, ($C_1$–$C_6$)alkoxy($C_1$–$C_6$)-alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, ($C_1$–C6)alkyl, aryl and aryl($C_1$–$C_6$)alkyl;

$R^3$, $R^4$, $R^5$, $R^7$, $R^{3a}$ and $R^{4a}$ are independently selected from the group consisting of H, ($C_1$–$C_6$)alkyl, aryl($C_1$–$C_6$)alkyl, —C(O)($C_1$–$C_6$)alkyl and —C(O)aryl;

$R^{30}$ is selected from the group consisting of $R^{32}$-substituted T, $R^{32}$-substituted-T—($C_1$–$C_6$)alkyl, $R^{32}$-substituted-($C_2$–$C_4$)alkenyl, $R^{32}$-substituted-($C_1$–$C_6$)alkyl, $R^{32}$-substituted-($C_3$–$C_7$)cycloalkyl and $R^{32}$-substituted-($C_3$–$C_7$)cycloalkyl($C_1$–$C_6$)alkyl;

$R^{31}$ is selected from the group consisting of H and ($C_1$–$C_4$)alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1–3 substituents independently selected from the group consisting of halogeno, ($C_1$–$C_4$)alkyl, —OH, phenoxy, —$CF_3$, —$NO_2$, ($C_1$–$C_4$) alkoxy, methylenedioxy, oxo, ($C_1$–$C_4$)alkylsulfanyl, ($C_1$–$C_4$)alkylsulfinyl, ($C_1$–$C_4$)alkylsulfonyl, —N($CH_3$)$_2$, —C(O)—NH($C_1$–$C_4$)alkyl, —C(O)—N(($C_1$–$C_4$)alkyl)$_2$, —C(O)—($C_1$–$C_4$)alkyl, —C(O)—($C_1$–$C_4$)alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a ($C_1$–$C_4$)alkoxycarbonyl-substituted pyrrolidinyl, piperidinyl, N-methylpiperazinyl, indolinyl or morpholinyl group;

$Ar^1$ is aryl or $R^{10}$-substituted aryl;
$Ar^2$ is aryl or $R^{11}$-substituted aryl;
Q is a bond or, with the 3-position ring carbon of the azetidinone, forms the spiro group

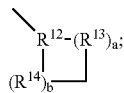

and $R^1$ is selected from the group consisting of
—($CH_2$)$_q$—, wherein q is 2–6, provided that when Q forms a spiro ring, q can also be zero or 1;

—($CH_2$)$_e$—E—($CH_2$)$_r$—, wherein E is —O—, —C(O)—, phenylene, —$NR^{22}$— or —S(O)$_{0-2}$—, e is 0–5 and r is 0–5, provided that the sum of e and r is 1–6;
—($C_2$–$C_6$)alkenylene-; and
—($CH_2$)$_f$—V—($CH_2$)$_g$—, wherein V is $C_3$–$C_6$ cycloalkylene, f is 1–5 and g is 0–5, provided that the sum of f and g is 1–6;

$R^{12}$ is

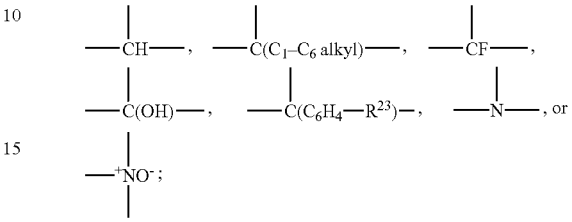

$R^{13}$ and $R^{14}$ are independently selected from the group consisting of —$CH_2$—, —CH($C_1$–$C_6$ alkyl)-, —C(di-($C_1$–$C_6$) alkyl), —CH=CH— and —C($C_1$–$C_6$ alkyl)=CH—; or $R^{12}$ together with an adjacent $R^{13}$, or $R^{12}$ together with an adjacent $R^{14}$, form a —CH=CH— or a —CH=C($C_1$–$C_6$ alkyl)-group;

a and b are independently 0, 1, 2 or 3, provided both are not zero;

provided that when $R^{13}$ is —CH=CH— or —C($C_1$–$C_6$ alkyl)=CH—, a is 1;
provided that when $R^{14}$ is —CH=CH— or —C($C_1$–$C_6$ alkyl)=CH—, b is 1;
provided that when a is 2 or 3, the $R^{13}$'s can be the same or different; and
provided that when b is 2 or 3, the $R^{14}$'s can be the same or different;

and when Q is a bond, $R^1$ also can be:

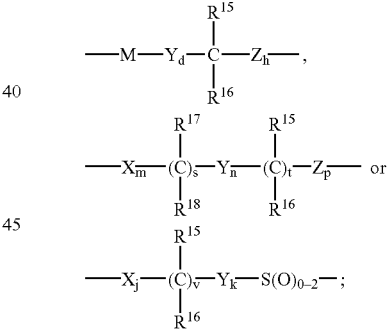

M is —O—, —S—, —S(O)— or —S(O)$_2$—;
X, Y and Z are independently selected from the group consisting of —$CH_2$—, —CH($C_1$–$C_6$)alkyl- and —C(di-($C_1$–$C_6$)alkyl);

$R^{10}$ and $R^{11}$ are independently selected from the group consisting of 1–3 substituents independently selected from the group consisting of ($C_1$–$C_6$)alkyl, —$OR^{19}$, —O(CO)$R^{19}$, —O(CO)O$R^{21}$, —O($CH_2$)$_{1-5}$$OR^{19}$, —O(CO)$NR^{19}R^{20}$, —$NR^{19}R^{20}$, —$NR^{19}$(CO)$R^{20}$, —$NR^{19}$(CO)O$R^{21}$, —$NR^{19}$(CO)$NR^2OR^{25}$, —$NR^{19}SO_2R^{21}$, —$COOR^{19}$, —$CONR^{19}R^{20}$, —$COR^{19}$, —$SO_2NR^{19}R^{20}$, S(O)$_{0-2}R^{21}$, —O($CH_2$)$_{1-10}$-$COOR^{19}$, —O($CH_2$)$_{1-10}$$CONR^{19}R^{20}$, —($C_1$–$C_6$ alkylene)—$COOR^{19}$, —CH=CH—$COOR^{19}$, —$CF_3$, —CN, —$NO_2$ and halogen;

$R^{15}$ and $R^{17}$ are independently selected from the group consisting of —$OR^{19}$, —O(CO)$R^{19}$, —O(CO)O$R^{21}$ and —O(CO)$NR^{19}R^{20}$;

$R^{16}$ and $R^{18}$ are independently selected from the group consisting of H, $(C_1-C_6)$alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1; t is 0 or 1; m, n and p are independently 0–4;

provided that at least one of s and t is 1, and the sum of m, n, p, s and t is 1–6;

provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

and when Q is a bond and $R^1$ is

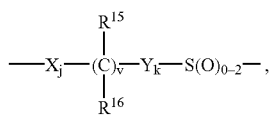

$Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, —C(O)$R^{19}$ or —COO$R^{19}$;

$R^{23}$ and $R^{24}$ are independently 1–3 groups independently selected from the group consisting of H, $(C_1-C_6)$alkyl, $(C_1-C_6)$alkoxy, —COOH, $NO_2$, —N$R^{19}R^{20}$, —OH and halogeno; and $R^{25}$ is H, —OH or $(C_1-C_6)$alkoxy.

In another embodiment, the present invention provides a composition comprising: (a) at least one peroxisome proliferator-activated receptor activator; and (b) at least one sterol absorption inhibitor represented by Formula (IX):

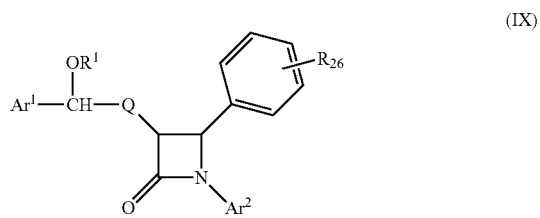

or isomers thereof, or pharmaceutically acceptable salts or solvates of the compounds of Formula (IX) or of the isomers thereof, or prodrugs of the compounds of Formula (IX) or of the isomers, salts or solvates thereof, wherein, in Formula (IX) above, $R^{26}$ is selected from the group consisting of:

a) OH;

b) $OCH_3$;

c) fluorine and d) chlorine.

$R^1$ is selected from the group consisting of

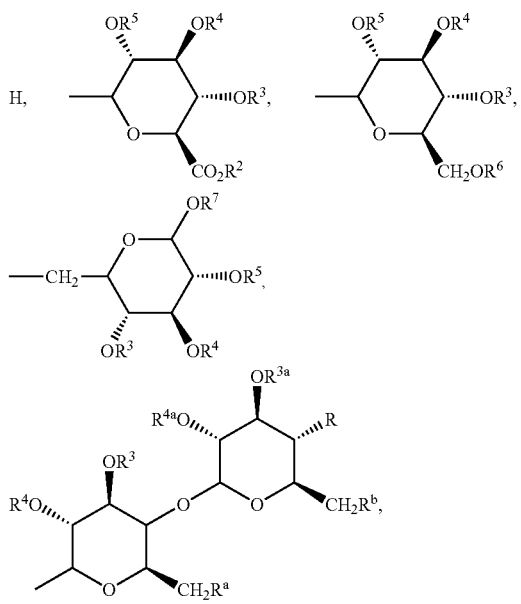

—$SO_3H$; natural and unnatural amino acids.

R, $R^a$ and $R^b$ are independently selected from the group consisting of H, —OH, halogeno, —$NH_2$, azido, $(C_1-C_6)$alkoxy$(C_1-C_6)$-alkoxy and —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, $(C_1-C_6)$alkyl, aryl and aryl$(C_1-C_6)$alkyl;

$R^3$, $R^4$, $R^5$, $R^7$, $R^{3a}$ and $R^{4a}$ are independently selected from the group consisting of H, $(C_1-C_6)$alkyl, aryl$(C_1-C_6)$alkyl, —C(O)$(C_1-C_6)$alkyl and —C(O)aryl;

$R^{30}$ is independently selected form the group consisting of $R^{32}$-substituted T, $R^{32}$-substituted-T—$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl$(C_1-C_6)$alkyl;

$R^{31}$ is independently selected from the group consisting of H and $(C_1-C_4)$alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1–3 substituents independently selected from the group consisting of H, halogeno, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —N$(CH_3)_2$, —C(O)—NH$(C_1-C_4)$alkyl, —C(O)—N$((C_1-C_4)$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is —(CH$_2$)$_q$—, wherein q is 2–6, or, with the 3-position ring carbon of the azetidinone,
forms the spiro group

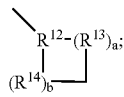

R$^{12}$ is

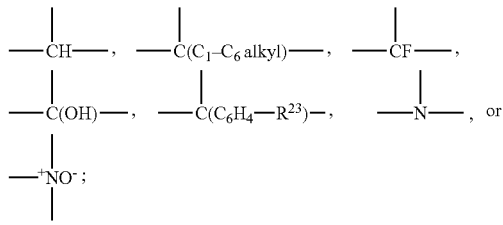

R$^{13}$ and R$^{14}$ are independently selected from the group consisting of —CH$_2$—, —CH(C$_1$–C$_6$ alkyl)-, —C(di-(C$_1$–C$_6$) alkyl), —CH=CH— and —C(C$_1$–C$_6$ alkyl)=CH—; or R$^{12}$ together with an adjacent R$^{13}$, or R$^{12}$ together with an adjacent R$^{14}$, form a —CH=CH— or a —CH=C(C$_1$–C$_6$ alkyl)-group;
a and b are independently 0, 1, 2 or 3, provided both are not zero; provided that when R$^{13}$ is —CH=CH— or —C(C$_1$–C$_6$ alkyl)=CH—, a is 1; provided that when R$^{14}$ is —CH=CH— or —C(C$_1$–C$_6$ alkyl)=CH—, b is 1; provided that when a is 2 or 3, the R$^{13}$'s can be the same or different; and provided that when b is 2 or 3, the R$^{14}$'s can be the same or different;
R$^{10}$ and R$^{11}$ are independently selected from the group consisting of 1–3 substituents independently selected from the group consisting of (C$_1$–C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$–C$_6$ alkylene)-COOR$^{19}$, —CH=CH—COOR$^{19}$, —CF$_3$, —CN, —NO$_2$ and halogen;
Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;
R$^{19}$ and R$^{20}$ are independently selected from the group consisting of H, (C$_1$–C$_6$)alkyl, aryl and aryl-substituted (C$_1$–C$_6$)alkyl;
R$^{21}$ is (C$_1$–C$_6$)alkyl, aryl or R$^{24}$-substituted aryl;
R$^{22}$ is H, (C$_1$–C$_6$)alkyl, aryl (C$_1$–C$_6$)alkyl, —C(O)R$^{19}$ or —COOR$^{19}$;
R$^{23}$ and R$^{24}$ are independently 1–3 groups independently selected from the group consisting of H, (C$_1$–C$_6$)alkyl, (C$_1$–C$_6$)alkoxy, —COOH, NO$_2$, —NR$^{19}$R$^{20}$, —OH and halogeno; and
R$^{25}$ is H, —OH or (C$_1$–C$_6$)alkoxy.
Therapeutic combinations also are provided comprising: (a) a first amount of at least one peroxisome proliferator-activated receptor activator; and (b) a second amount of at least one sterol absorption inhibitor represented by Formulae (I–XI) above or isomers thereof, or pharmaceutically acceptable salts or solvates of the compounds of Formula (I–XI) or of the isomers thereof, or prodrugs of the compounds of Formula (I–XI) or of the isomers, salts or solvates thereof, wherein the first amount and the second amount together comprise a therapeutically effective amount for the treatment or prevention of a vascular condition, diabetes, obesity or lowering a concentration of a sterol in plasma of a mammal.

Pharmaceutical compositions for the treatment or prevention of a vascular condition, diabetes, obesity or lowering a concentration of a sterol in plasma of a mammal, comprising a therapeutically effective amount of the above compositions or therapeutic combinations and a pharmaceutically acceptable carrier also are provided.

Methods of treating or preventing a vascular condition, diabetes, obesity or lowering a concentration of a sterol in plasma of a mammal, comprising the step of administering to a mammal in need of such treatment an effective amount of the above compositions or therapeutic combinations also are provided.

Other than in the operating examples, or where otherwise indicated, all numbers expressing quantities of ingredients, reaction conditions, and so forth used in the specification and claims are to be understood as being modified in all instances by the term "about."

DETAILED DESCRIPTION

The compositions and therapeutic combinations of the present invention comprise at least one (one or more) activators for peroxisome proliferator-activated receptors (PPAR). These activators act as agonists for the peroxisome proliferator-activated receptors. Three subtypes of PPAR have been identified, and these are designated as peroxisome proliferator-activated receptor alpha (PPARα), peroxisome proliferator-activated receptor gamma (PPARγ) and peroxisome proliferator-activated receptor delta (PPARδ). It should be noted that PPARδ is also referred to in the literature as PPARβ and as NUC1, and each of these names refers to the same receptor.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans. See, e.g., WO 97/28149.

PPARα activator compounds are useful for, among other things, lowering triglycerides, moderately lowering LDL levels and increasing HDL levels. Examples of PPARα activators useful in the compositions of the present invention include fibrates.

Non-limiting examples of suitable fibric acid derivatives ("fibrates") include clofibrate (such as ethyl 2-(p-chlorophenoxy)-2-methyl-propionate, for example ATROMID-S® Capsules which are commercially available from Wyeth-Ayerst); gemfibrozil (such as 5-(2,5-dimethylphenoxy)-2,2-dimethylpentanoic acid, for example LOPID® tablets which are commercially available from Parke Davis); ciprofibrate (C.A.S. Registry No. 52214-84-3, see U.S. Pat. No. 3,948,973 which is incorporated herein by reference); bezafibrate (C.A.S. Registry No. 41859-67-0, see U.S. Pat. No. 3,781,328 which is incorporated herein by reference); clinofibrate (C.A.S. Registry No. 30299-08-2, see U.S. Pat. No. 3,716,583 which is incorporated herein by reference); binifibrate (C.A.S. Registry No. 69047-39-8, see BE 884722 which is incorporated herein by reference); lifibrol (C.A.S. Registry No. 96609-16-4); fenofibrate (such as TRICOR® micronized fenofibrate (2-[4-(4-chlorobenzoyl) phenoxy]-2-methyl-propanoic acid, 1-methylethyl ester) which is commercially available from Abbott Laboratories or LIPANTHYL® micronized fenofibrate which is commercially available from Labortoire Founier, France) and mixtures thereof. These compounds can be used in a variety of forms, including but not limited to acid form, salt form, racemates, enantiomers, zwitterions and tautomers.

Other examples of PPARα activators useful with the practice of the present invention include suitable fluorophenyl compounds as disclosed in U.S. Pat. No. 6,028,109 which is incorporated herein by reference; certain substituted phenylpropionic compounds as disclosed in WO 00/75103 which is incorporated herein by reference; and PPARα activator compounds as disclosed in WO 98/43081 which is incorporated herein by reference.

Non-limiting examples of suitable PPARγ activators useful in the compositions of the present invention include suitable derivatives of glitazones or thiazolidinediones, such as, troglitazone (such as REZULIN® troglitazone (-5-[[4-[3,4-dihydro-6-hydroxy-2,5,7,8-tetramethyl-2H-1-benzopyran-2-yl)methoxy]phenyl]methyl]-2,4-thiazolidinedione) commercially available from Parke-Davis); rosiglitazone (such as AVANDIA® rosiglitazone maleate (-5-[[4-[2-(methyl-2-pyridinylamino)ethoxy] phenyl]methyl]-2,4-thiazolidinedione, (Z)-2-butenedioate) (1:1) commercially available from SmithKline Beecham) and pioglitazone (such as ACTOS™ pioglitazone hydrochloride (5-[[4-[2-(5-ethyl-2-pyridinyl)ethoxy]phenyl]methyl]-2,4-] thiazolidinedione monohydrochloride) commercially available from Takeda Pharmaceuticals). Other useful thiazolidinediones include ciglitazone, englitazone, darglitazone and BRL 49653 as disclosed in WO 98/05331; PPARγ activator compounds disclosed in WO 00/76488; and PPARγ activator compounds disclosed in U.S. Pat. No. 5,994,554 which is incorporated herein by reference.

Other useful PPARγ activator compounds include certain acetylphenols as disclosed in U.S. Pat. No. 5,859,051 which is incorporated herein by reference; certain quinoline phenyl compounds as disclosed in WO 99/20275; aryl compounds as disclosed by WO 99/38845; certain 1,4-disubstituted phenyl compounds as disclosed in WO 00/63161; certain aryl compounds as disclosed in WO 01/00579; benzoic acid compounds as disclosed in WO 01/12612 and WO 01/12187; and substituted 4-hydroxy-phenylalconic acid compounds as disclosed in WO 97/31907.

PPARδ compounds are useful for, among other things, lowering triglyceride levels or raising HDL levels. Non-limiting examples of suitable PPARδ activators useful in the compositions of the present invention include suitable thiazole and oxazole derivates, such as C.A.S. Registry No. 317318-32-4, as disclosed in WO 01/00603; certain fluoro, chloro or thio phenoxy phenylacetic acids as disclosed in WO 97/28149; suitable non-β-oxidizable fatty acid analogues as disclosed in U.S. Pat. No. 5,093,365 which is incorporated herein by reference; and PPARδ activator compounds disclosed in WO 99/04815.

Moreover, compounds that have multiple functionality for activating various combinations of PPARα, PPARγ and PPARδ also are useful in compositions of the present invention. Non-limiting examples include certain substituted aryl compounds as disclosed in U.S. Pat. No. 6,248,781 incorporated herein by reference; WO 00/23416; WO 00/23415; WO 00/23425; WO 00/23445; WO 00/23451; and WO 00/63153, which are described as being useful PPARα and/or PPARγ activator compounds. Other non-limiting examples of useful PPARα and/or PPARγ activator compounds include activator compounds as disclosed in WO 97/25042; activator compounds as disclosed in WO 00/63190; activator compounds as disclosed in WO 01/21181; biaryl-oxa(thia)zole compounds as disclosed in WO 01/16120; activator compounds as disclosed in WO 00/63196 and WO 00/63209; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G; GW2331 or (2-(4-[difluorophenyl]-1heptylureido)ethyl]phenoxy)-2-methylbutyric compounds as disclosed in WO 98/05331; aryl compounds as disclosed in U.S. Pat. No. 6,166,049 which is incorporated herein by reference; oxazole compounds as disclosed in WO 01/17994; and dithiolane compounds as disclosed in WO 01/25225 and WO 01/25226.

Other useful PPAR activator compounds include substituted benzylthiazolidine-2,4-dione compounds as disclosed in WO 01/14349, WO 01/14350 and WO/01/04351; mercaptocarboxylic compounds as disclosed in WO 00/50392; ascofuranone compounds as disclosed in WO 00/53563; carboxylic compounds as disclosed in WO 99/46232; compoundsas disclosed in WO 99/12534; benzene compounds as disclosed in WO 99/15520; o-anisamide compounds as disclosed in WO 01/21578; and PPAR activator compounds as disclosed in WO 01/40192.

The peroxisome proliferator-activated receptor(s) activator(s) are administered in a therapeutically effective amount to treat the specified condition, for example in a daily dose can range from about 0.1 to about 1000 mg per day, preferably about 0.25 to about 50 mg/day, and more preferably about 10 mg per day, given in a single dose or 24 divided doses. The exact dose, however, is determined by the attending clinician and is dependent on such factors as the potency of the compound administered, the age, weight, condition and response of the patient.

The term "therapeutically effective amount" means that amount of a therapeutic agent of the composition, such as the peroxisome proliferator-activated receptor activator(s), sterol absorption inhibitor(s) and other pharmacological or therapeutic agents described below, that will elicit a biological or medical response of a tissue, system, animal or mammal that is being sought by the administrator (such as a researcher, doctor or veterinarian) which includes alleviation of the symptoms of the condition or disease being treated and the prevention, slowing or halting of progression of one or more conditions, for example vascular conditions, such as hyperlipidaemia (for example atherosclerosis, hypercholesterolemia or sitosterolemia), vascular inflammation, stroke, diabetes, obesity and/or to reduce the level of sterol(s) (such as cholesterol) in the plasma.

As used herein, "combination therapy" or "therapeutic combination" means the administration of two or more therapeutic agents, such as peroxisome proliferator-activated receptor activator(s) and sterol absorption inhibitor (s), to prevent or treat a condition, for example a vascular condition, such as hyperlipidaemia (for example atherosclerosis, hypercholesterolemia or sitosterolemia), vascular inflammation, stroke, diabetes, obesity and/or reduce the level of sterol(s) (such as cholesterol) in the plasma. As used herein, "vascular" comprises cardiovascular, cerebrovascular and combinations thereof. The compositions, combinations and treatments of the present invention can be administered by any suitable means which produce contact of these compounds with the site of action in the body, for example in the plasma, liver or small intestine of a mammal or human. Such administration includes coadministration of these therapeutic agents in a substantially simultaneous manner, such as in a single tablet or capsule having a fixed ratio of active ingredients or in multiple, separate capsules for each therapeutic agent. Also, such administration includes use of each type of therapeutic agent in a sequential manner. In either case, the treatment using the combination therapy will provide beneficial effects in treating the condition. A potential advantage of the combination therapy disclosed herein may be a reduction in the required amount of an individual therapeutic compound or the overall total amount of therapeutic compounds that are effective in treating the condition. By using a combination of therapeutic agents, the side effects of the individual compounds can be reduced as compared to a monotherapy, which can improve patient compliance. Also, therapeutic agents can be selected to provide a broader range of complimentary effects or complimentary modes of action.

As discussed above, the compositions, pharmaceutical compositions and therapeutic combinations of the present invention comprise one or more substituted azetidinone or substituted β-lactam sterol absorption inhibitors discussed in detail below. As used herein, "sterol absorption inhibitor" means a compound capable of inhibiting the absorption of one or more sterols, including but not limited to cholesterol, phytosterols (such as sitosterol, campesterol, stigmasterol and avenosterol), 5α-stanols (such as cholestanol, 5x-campestanol, 5α-sitostanol), and mixtures thereof, when administered in a therapeutically effective (sterol absorption inhibiting) amount to a mammal or human.

In a preferred embodiment, sterol absorption inhibitors useful in the compositions, therapeutic combinations and methods of the present invention are represented by Formula (I) below:

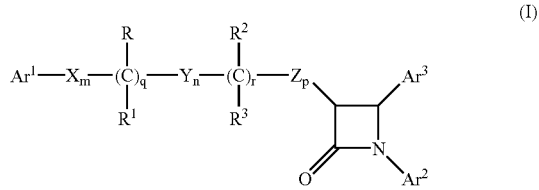

(I)

or isomers of the compounds of Formula (I), or pharmaceutically acceptable salts or solvates of the compounds of Formula (I) or of the isomers of the compounds of Formula (I), or prodrugs of the compounds of Formula (I) or of the isomers, salts or solvates of the compounds of Formula (I), wherein, in Formula (I) above:

$Ar^1$ and $Ar^2$ are independently selected from the group consisting of aryl and $R^4$-substituted aryl;

$Ar^3$ is aryl or $R^5$-substituted aryl;

X, Y and Z are independently selected from the group consisting of —CH$_2$—, —CH(lower alkyl)- and —C(dilower alkyl)-;

R and $R^2$ are independently selected from the group consisting of —OR$^6$, —O(CO)R$^6$, —O(CO)OR and —O(CO)NR$^6$R$^7$;

$R^1$ and $R^3$ are independently selected from the group consisting of hydrogen, lower alkyl and aryl;

q is 0 or 1; r is 0 or 1; m, n and p are independently selected from 0, 1, 2, 3 or 4; provided that at least one of q and r is 1, and the sum of m, n, p, q and r is 1, 2, 3, 4, 5 or 6; and provided that when p is 0 and r is 1, the sum of m, q and n is 1, 2, 3, 4 or 5;

$R^4$ is 1–5 substituents independently selected from the group consisting of lower alkyl, —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO)R$^7$, —NR$^6$(CO)OR$^9$, —NR$^6$(CO) NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$R$^9$, —O(CH$_2$)$_{1-10}$—COOR$^6$, —O(CH$_2$)$_{1-10}$CONR$^6$R$^7$, -(lower alkylene)COOR$^6$, —CH═CH—COOR$^6$, —CF$_3$, —CN, —NO$_2$ and halogen;

$R^5$ is 1–5 substituents independently selected from the group consisting of —OR$^6$, —O(CO)R$^6$, —O(CO)OR$^9$, —O(CH$_2$)$_{1-5}$OR$^6$, —O(CO)NR$^6$R$^7$, —NR$^6$R$^7$, —NR$^6$(CO) R$^7$, —NR$^6$(CO)OR$^9$, —NR$^6$(CO)NR$^7$R$^8$, —NR$^6$SO$_2$R$^9$, —COOR$^6$, —CONR$^6$R$^7$, —COR$^6$, —SO$_2$NR$^6$R$^7$, S(O)$_{0-2}$ R$^9$, —O(CH$_2$)$_{1-10}$—COOR$^6$, —O(CH$_2$)$_{1-10}$CONR$^6$R$^7$, -(lower alkylene)COOR$^6$ and —CH═CH—COOR$^6$;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferably, $R^4$ is 1–3 independently selected substituents, and $R^5$ is preferably 1–3 independently selected substituents.

As used herein, the term "alkyl" or "lower alkyl" means straight or branched alkyl chains having from 1 to 6 carbon atoms and "alkoxy" means alkoxy groups having 1 to 6 carbon atoms. Non-limiting examples of lower alkyl groups include, for example methyl, ethyl, propyl, and butyl groups.

"Alkenyl" means straight or branched carbon chains having one or more double bonds in the chain, conjugated or unconjugated. Similarly, "alkynyl" means straight or branched carbon chains having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional isomers.

"Halogeno" refers to fluorine, chlorine, bromine or iodine radicals.

"Aryl" means phenyl, naphthyl, indenyl, tetrahydronaphthyl or indanyl.

"Phenylene" means a bivalent phenyl group, including ortho, meta and para-substitution.

The statements wherein, for example, R, $R^1$, $R^2$ and $R^3$, are said to be independently selected from a group of substituents, mean that R, $R^1$, $R^2$ and $R^3$ are independently selected, but also that where an R, $R^1$, $R^2$ and $R^3$ variable occurs more than once in a molecule, each occurrence is independently selected (e.g., if R is —OR$^6$, wherein $R^6$ is hydrogen, $R^2$ can be —OR$^6$ wherein $R^6$ is lower alkyl). Those skilled in the art will recognize that the size and nature of the substituent(s) will affect the number of substituents that can be present.

Compounds of the invention have at least one asymmetrical carbon atom and therefore all isomers, including enantiomers, stereoisomers, rotamers, tautomers and racemates of the compounds of Formula (I–XI) (where they exist) are contemplated as being part of this invention. The invention includes d and l isomers in both pure form and in admixture, including racemic mixtures. Isomers can be prepared using conventional techniques, either by reacting optically pure or optically enriched starting materials or by separating isomers of a compound of the Formulae I–XI. Isomers may also include geometric isomers, e.g., when a double bond is present.

Those skilled in the art will appreciate that for some of the compounds of the Formulae I–XI, one isomer will show greater pharmacological activity than other isomers.

Compounds of the invention with an amino group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, gold and silver salts. Also included are salts formed with pharmaceutically acceptable amines such as ammonia, alkyl amines, hydroxyalkylamines, N-methylglucamine and the like.

As used herein, "solvate" means a molecular or ionic complex of molecules or ions of solvent with those of solute (for example, one or more compounds of Formulae I–XI, isomers of the compounds of Formulae I–XI, or prodrugs of the compounds of Formulae I–XI). Non-limiting examples of useful solvents include polar, protic solvents such as water and/or alcohols (for example methanol).

As used herein, "prodrug" means compounds that are drug precursors which, following administration to a patient, release the drug in vivo via some chemical or physiological process (e.g., a prodrug on being brought to the physiological pH or through enzyme action is converted to the desired drug form).

Preferred compounds of Formula (I) are those in which $Ar^1$ is phenyl or $R^4$-substituted phenyl, more preferably (4-$R^4$)-substituted phenyl. $Ar^2$ is preferably phenyl or $R^4$-substituted phenyl, more preferably (4-$R^4$)-substituted phenyl. $Ar^3$ is preferably $R^5$-substituted phenyl, more preferably (4-$R^5$)-substituted phenyl. When $Ar^1$ is (4-$R^4$)-substituted phenyl, $R^4$ is preferably a halogen. When $Ar^2$ and $Ar^3$ are $R^4$- and $R^5$-substituted phenyl, respectively, $R^4$ is preferably halogen or —$OR^6$ and $R^5$ is preferably —$OR^6$, wherein $R^6$ is lower alkyl or hydrogen. Especially preferred are compounds wherein each of $Ar^1$ and $Ar^2$ is 4-fluorophenyl and $Ar^3$ is 4-hydroxyphenyl or 4-methoxyphenyl.

X, Y and Z are each preferably —$CH_2$—. $R^1$ and $R^3$ are each preferably hydrogen. R and $R^2$ are preferably —$OR^6$ wherein $R^6$ is hydrogen, or a group readily metabolizable to a hydroxyl (such as —O(CO)$R^6$, —O(CO)O$R^9$ and —O(CO)N$R^6R^7$, defined above).

The sum of m, n, p, q and r is preferably 2, 3 or 4, more preferably 3. Preferred are compounds wherein m, n and r are each zero, q is 1 and p is 2.

Also preferred are compounds of Formula (I) in which p, q and n are each zero, r is 1 and m is 2 or 3. More preferred are compounds wherein m, n and r are each zero, q is 1, p is 2, Z is —$CH_2$— and R is —$OR^6$, especially when $R^6$ is hydrogen.

Also more preferred are compounds of Formula (I) wherein p, q and n are each zero, r is 1, m is 2, X is —$CH_2$— and $R^2$ is —$OR^6$, especially when $R^6$ is hydrogen.

Another group of preferred compounds of Formula (I) is that in which $Ar^1$ is phenyl or $R^4$-substituted phenyl, $Ar^2$ is phenyl or $R^4$-substituted phenyl and $Ar^3$ is $R^5$-substituted phenyl. Also preferred are compounds in which $Ar^1$ is phenyl or $R^4$-substituted phenyl, $Ar^2$ is phenyl or $R^4$-substituted phenyl, $Ar^3$ is $R^5$-substituted phenyl, and the sum of m, n, p, q and r is 2, 3 or 4, more preferably 3. More preferred are compounds wherein $Ar^1$ is phenyl or $R^4$-substituted phenyl, $Ar^2$ is phenyl or $R^4$-substituted phenyl, $Ar^3$ is $R^5$-substituted phenyl, and wherein m, n and r are each zero, q is 1 and p is 2, or wherein p, q and n are each zero, r is 1 and m is 2 or 3.

In a preferred embodiment, a sterol inhibitor of Formula (I) useful in the compositions, therapeutic combinations and methods of the present invention is represented by Formula (II) (ezetimibe) below:

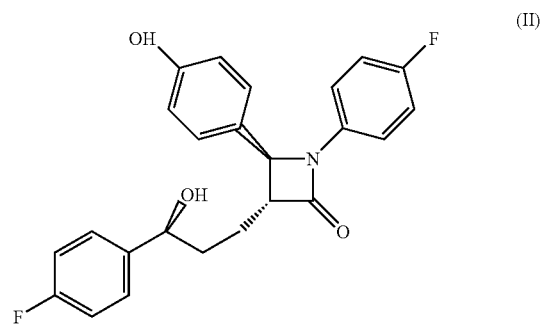

(II)

or pharmaceutically acceptable salts or solvates of the compound of Formula (II), or prodrugs of the compound of Formula (II) or of the salts or solvates of the compound of Formula (II).

Compounds of Formula I can be prepared by a variety of methods well know to those skilled in the art, for example such as are disclosed in U.S. Pat. Nos. 5,631,365, 5,767,115, 5,846,966, 6,207,822, U.S. Provisional Patent Application No. 60/279,288 filed Mar. 28, 2001, and PCT Patent Application WO 93/02048, each of which is incorporated herein by reference, and in the Example below. For example, suitable compounds of Formula I can be prepared by a method comprising the steps of:

(a) treating with a strong base a lactone of the Formula A or B:

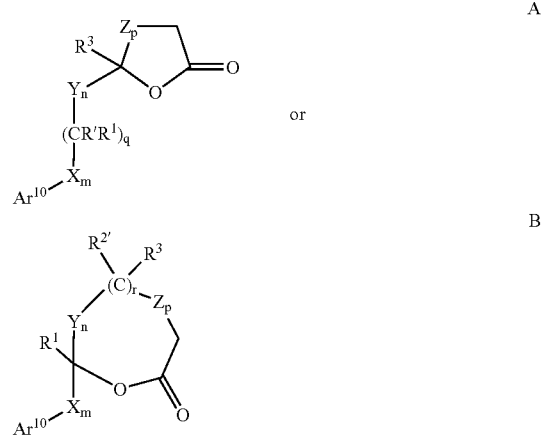

wherein R' and $R^{2'}$ are R and $R^2$, respectively, or are suitably protected hydroxy groups; $Ar^{10}$ is $Ar^1$, a suitably protected hydroxy-substituted aryl or a suitably protected amino-substituted aryl; and the remaining variables are as defined above for Formula I, provided that in lactone of formula B, when n and r are each zero, p is 1–4;

(b) reacting the product of step (a) with an imine of the formula

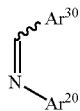

wherein $Ar^{20}$ is $Ar^2$, a suitably protected hydroxy-substituted aryl or a suitably protected amino-substituted aryl; and $Ar^{30}$ is $Ar^3$, suitably protected hydroxy-substituted aryl or a suitably protected amino-substituted aryl;

c) quenching the reaction with an acid;

d) optionally removing the protecting groups from R', $R^{2'}$, $Ar^{10}$, $Ar^{20}$ and $Ar^{30}$, when present; and e) optionally functionalizing hydroxy or amino substituents at R, $R^2$, $Ar^1$, $Ar^2$ and $Ar^3$.

Using the lactones shown above, compounds of Formula IA and IB are obtained as follows:

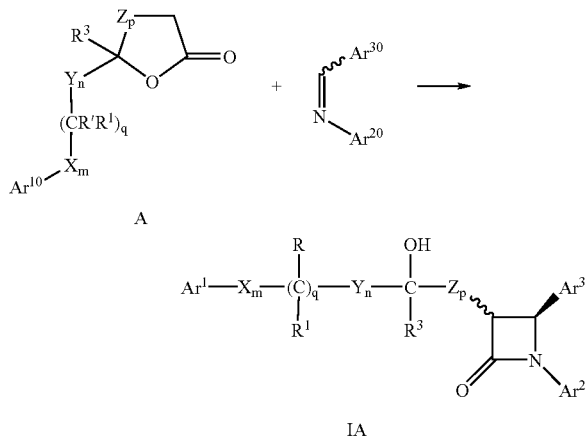

wherein the variables are as defined above; and

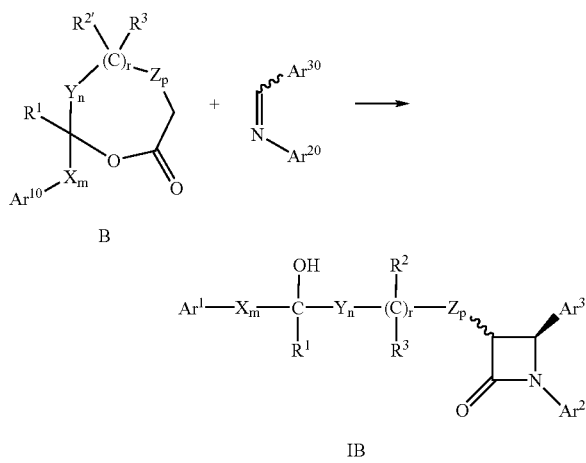

wherein the variables are as defined above.

Alternative sterol absorption inhibitors useful in the compositions, therapeutic combinations and methods of the present invention are represented by Formula (III) below:

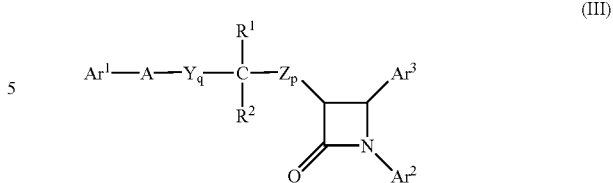

(III)

or isomers of the compounds of Formula (III), or pharmaceutically acceptable salts or solvates of the compounds of Formula (III) or of the isomers of the compounds of Formula (III), or prodrugs of the compounds of Formula (III) or of the isomers, salts or solvates of the compounds of Formula (III), wherein, in Formula (III) above:

$Ar^1$ is $R_3$-substituted aryl;
$Ar^2$ is $R^4$-substituted aryl;
$Ar^3$ is $R^5$-substituted aryl;

Y and Z are independently selected from the group consisting of —$CH_2$—, —CH(lower alkyl)- and —C(dilower alkyl)-;

A is selected from —O—, —S—, —S(O)— or —$S(O)_2$—;

$R^1$ is selected from the group consisting of —$OR^6$, —$O(CO)R^6$, —$O(CO)OR^9$ and —$O(CO)NR^6R^7$; $R^2$ is selected from the group consisting of hydrogen, lower alkyl and aryl; or R and R together are =O;

q is 1, 2 or 3;
p is 0, 1, 2, 3 or 4;

$R^5$ is 1–3 substituents independently selected from the group consisting of —$OR^6$, —$O(CO)R^6$, —$O(CO)OR^9$, —$O(CH_2)_{1-5}OR^9$, —$O(CO)NR^6R^7$, —$NR^6R^7$, —$NR^6(CO)R^7$, —$NR^6(CO)OR^9$, —$NR^6(CO)NR^7R^8$, —$NR^6SO_2$-lower alkyl, —$NR^6SO_2$-aryl, —$CONR^6R^7$, —$COR^6$, —$SO_2NR^6R^7$, $S(O)_{0-2}$-alkyl, $S(O)_{0-2}$-aryl, —$O(CH_2)_{1-10}$—$COOR^6$, —$O(CH_2)_{1-10}CONR^6R^7$, o-halogeno, m-halogeno, o-lower alkyl, m-lower alkyl, -(lower alkylene)-$COOR^6$, and —CH=CH—COOR;

$R^3$ and $R^4$ are independently 1–3 substituents independently selected from the group consisting of $R^5$, hydrogen, p-lower alkyl, aryl, —$NO_2$, —$CF_3$ and p-halogeno;

$R^6$, $R^7$ and $R^8$ are independently selected from the group consisting of hydrogen, lower alkyl, aryl and aryl-substituted lower alkyl; and $R^9$ is lower alkyl, aryl or aryl-substituted lower alkyl.

Preferred compounds of Formula I include those in which $Ar^1$ is $R^3$-substituted phenyl, especially (4-$R^3$)-substituted phenyl. $Ar^2$ is preferably $R^4$-substituted phenyl, especially (4-$R^4$)-substituted phenyl. $Ar^3$ is preferably $R^5$-substituted phenyl, especially (4-$R^5$)-substituted phenyl. Monosubstitution of each of $Ar^1$, $Ar^2$ and $Ar^3$ is preferred.

Y and Z are each preferably —$CH_2$—. $R^2$ is preferably hydrogen. $R^1$ is preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above). Also preferred are compounds wherein $R^1$ and $R^2$ together are =O.

The sum of q and p is preferably 1 or 2, more preferably 1. Preferred are compounds wherein p is zero and q is 1. More preferred are compounds wherein p is zero, q is 1, Y is —$CH_2$— and $R^1$ is —$OR^6$, especially when $R^6$ is hydrogen.

Another group of preferred compounds is that in which $Ar^1$ is $R^3$-substituted phenyl, $Ar^2$ is $R^4$-substituted phenyl and $Ar^3$ is $R^5$-substituted phenyl.

Also preferred are compounds wherein $Ar^1$ is $R^3$-substituted phenyl, $Ar^2$ is $R^4$-substituted phenyl, $Ar^3$ is $R^5$-substituted phenyl, and the sum of p and q is 1 or 2, especially 1. More preferred are compounds wherein $Ar^1$ is $R^3$-substituted phenyl, $Ar^2$ is $R^4$-substituted phenyl, $Ar^3$ is $R^5$-substituted phenyl, p is zero and q is 1.

A is preferably —O—.

$R^3$ is preferably —COOR$^6$, —CONR$^6$R$^7$, —COR$^6$, —SO$_2$NR$^6$R$^7$, S(O)$_{0-2}$-alkyl, S(O)$_{0-2}$-aryl, NO$_2$ or halogeno. A more preferred definition for $R^3$ is halogeno, especially fluoro or chloro.

$R^4$ is preferably hydrogen, lower alkyl, —OR$^6$, —O(CO)R$^6$, —O(CO)OR$^9$, —O(CO)NR$^6$R$^7$, —NR$^6$R$^7$, COR$^6$ or halogeno, wherein $R^6$ and $R^7$ are preferably independently hydrogen or lower alkyl, and $R^9$ is preferably lower alkyl. A more preferred definition for $R^4$ is hydrogen or halogeno, especially fluoro or chloro.

$R^5$ is preferably —OR$^6$, —O(CO)R$_6$, —O(CO)OR$^9$, —O(CO)NR$_6$R$^7$, —NR$^6$R$^7$, -(lower alkylene)-COOR$^6$ or —CH=CH—COOR$^6$, wherein $R^6$ and $R^7$ are preferably independently hydrogen or lower alkyl, and $R^9$ is preferably lower alkyl. A more preferred definition for $R^5$ is —OR$^6$, -(lower alkylene)—COOR$^6$ or —CH=CH—COOR$^6$, wherein $R^6$ is preferably hydrogen or lower alkyl.

Methods for making compounds of Formula III are well known to those skilled in the art. Non-limiting examples of suitable methods are disclosed in U.S. Pat. No. 5,688,990, which is incorporated herein by reference.

In another embodiment, sterol absorption inhibitors useful in the compositions, therapeutic combinations and methods of the present invention are represented by Formula (IV):

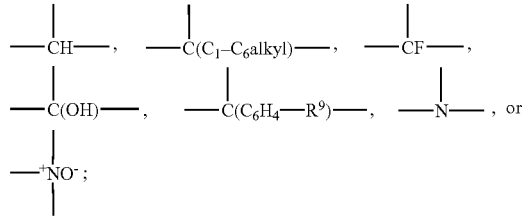

or isomers of the compounds of Formula (IV), or pharmaceutically acceptable salts or solvates of the compounds of Formula (IV) or of the isomers of the compounds of Formula (IV), or prodrugs of the compounds of Formula (IV) or of the isomers, salts or solvates of the compounds of Formula (IV), wherein, in Formula (IV) above:

A is selected from the group consisting of $R^2$-substituted heterocycloalkyl, $R^2$-substituted heteroaryl, $R^2$-substituted benzofused heterocycloalkyl, and $R^2$-substituted benzofused heteroaryl;

$Ar^1$ is aryl or $R^3$-substituted aryl;

$Ar^2$ is aryl or $R^4$-substituted aryl;

Q is a bond or, with the 3-position ring carbon of the azetidinone, forms the spiro group

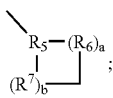

and $R^1$ is selected from the group consisting of:

—(CH$_2$)$_q$—, wherein q is 2–6, provided that when Q forms a spiro ring, q can also be zero or 1;

—(CH$_2$)$_e$—G—(CH$_2$)$_r$—, wherein G is —O—, —C(O)—, phenylene, —NR$^8$— or —S(O)$_{0-2}$—, e is 0–5 and r is 0–5, provided that the sum of e and r is 1–6;

—(C$_2$–C$_6$ alkenylene)-; and

—(CH$_2$)$_f$—V—(CH$_2$)$_g$—, wherein V is C$_3$–C$_6$ cycloalkylene, f is 1–5 and g is 0–5, provided that the sum of f and g is 1–6;

$R^5$ is selected from:

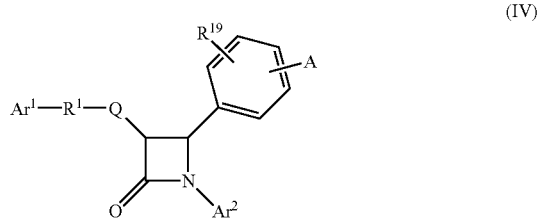

$R^6$ and $R^7$ are independently selected from the group consisting of —CH$_2$—, —CH(C$_1$–C$_6$ alkyly, —C(di-(C$_1$–C$_6$) alkyl), —CH=CH— and —C(C$_1$–C$_6$ alkyl)=CH—; or $R^5$ together with an adjacent $R^6$, or $R^5$ together with an adjacent $R^7$, form a —CH=CH— or a —CH=C(C$_1$–C$_6$ alkyl)-group;

a and b are independently 0, 1, 2 or 3, provided both are not zero; provided that when $R^6$ is —CH=CH— or —C(C$_1$–C$_6$ alkyl)=CH—, a is 1; provided that when $R^7$ is —CH=CH— or —C(C$_1$–C$_6$ alkyl)=CH—, b is 1; provided that when a is 2 or 3, the $R^6$'s can be the same or different; and provided that when b is 2 or 3, the $R^7$'s can be the same or different;

and when Q is a bond, $R^1$ also can be selected from:

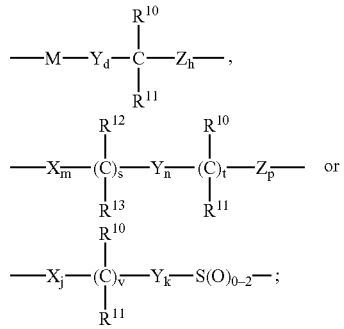

where M is —O—, —S—, —S(O)— or —S(O)$_2$—;

X, Y and Z are independently selected from the group consisting of —CH$_2$—, —CH(C$_1$–C$_6$ alkyl)- and —C(di-(C$_1$–C$_6$) alkyl);

$R^{10}$ and $R^{12}$ are independently selected from the group consisting of —OR$^{14}$, —O(CO)R$^{14}$, —O(CO)OR$^{16}$ and —O(CO)NR$^{14}$R$^{15}$;

$R^{11}$ and $R^{13}$ are independently selected from the group consisting of hydrogen, (C$_1$–C$_6$)alkyl and aryl; or $R^{10}$ and $R^{11}$ together are =O, or $R^{12}$ and $R^{13}$ together are =O;

d is 1, 2 or 3;

h is 0, 1, 2, 3 or 4;

s is 0 or 1; t is 0 or 1; m, n and p are independently 0–4; provided that at least one of s and t is 1, and the sum of m, n, p, s and t is 1–6; provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

$R^2$ is 1–3 substituents on the ring carbon atoms selected from the group consisting of hydrogen, (C$_1$–C$_{10}$)alkyl, (C$_2$–C$_{10}$)alkenyl, (C$_2$–C$_{10}$)alkynyl, (C$_3$–C$_6$)cycloalkyl, $(C_3-C_6)$cycloalkenyl, $R^{17}$-substituted aryl, $R^{17}$-substituted benzyl, $R^{17}$-substituted benzyloxy, $R^{17}$-substituted aryloxy, halogeno, —$N^{14}R^{15}$, $NR^{14}R^{15}(C_1-C_6$ alkylene)-, $NR^{14}R^{15}C(O)(C_1-C_6$ alkylene)-, —$NHC(O)R^{16}$, OH, $C_1-C_6$ alkoxy, —$OC(O)R^{16}$, —$COR^{14}$, hydroxy$(C_1-C_6)$ alkyl, $(C_1-C_6)$alkoxy$(C_1-C_6)$alkyl, $NO_2$, —$S(O)_{0-2}R^{16}$, —$SO_2NR^{14}R^{15}$ and —$(C_1-C_6$ alkylene)$COOR^{14}$; when $R^2$ is a substituent on a heterocycloalkyl ring, $R^2$ is as defined, or is =O or

[structure: dioxolane with $(CH_2)_{1-2}$]

and, where $R^2$ is a substituent on a substitutable ring nitrogen, it is hydrogen, $(C_1-C_6)$alkyl, aryl, $(C_1-C_6)$alkoxy, aryloxy, $(C_1-C_6)$alkylcarbonyl, arylcarbonyl, hydroxy, —$(CH_2)_{1-6}CONR^{18}R^{18}$,

[two structures with $R^{18}$, J, $(CH_2)_{0-4}$] or [oxazolidine];

wherein J is —O—, —NH—, —$NR^{18}$— or —$CH_2$—;
$R^3$ and $R^4$ are independently selected from the group consisting of 1–3 substituents independently selected from the group consisting of $(C_1-C_6)$alkyl, —$OR^{14}$, —$O(CO)R^{14}$, —$O(CO)OR^{16}$, —$O(CH_2)_{1-5}OR^{14}$, —$O(CO)NR^{14}R^{15}$, —$NR^{14}R^{15}$, —$NR^{14}(CO)R^{15}$, —$NR^{14}(CO)OR^{16}$, —$NR^{14}(CO)NR^{15}R^{19}$, —$NR^{14}SO_2R^{16}$, —$COOR^{14}$, —$CONR^{14}R^{15}$, —$COR^{14}$, —$SO_2NR^{14}R^{15}$, $S(O)_{0-2}R^{16}$, —$O(CH_2)_{1-10}$—$COOR^{14}$, —$O(CH_2)_{1-10}CONR^{14}R^{15}$, —$(C_1-C_6$ alkylene)—$COOR^{14}$, —$CH=CH$—$COOR^{14}$, —$CF_3$, —$CN_3$, —$NO_2$ and halogen;
$R^8$ is hydrogen, $(C_1-C_6)$alkyl, aryl $(C_1-C_6)$alkyl, —$C(O)R^{14}$ or —$COOR^{14}$;
$R^9$ and $R^{17}$ are independently 1–3 groups independently selected from the group consisting of hydrogen, $(C_1-C_6)$ alkyl, $(C_1-C_6)$alkoxy, —COOH, $NO_2$, —$NR^{14}R^{15}$, OH and halogeno;
$R^{14}$ and $R^{15}$ are independently selected from the group consisting of hydrogen, $(C_1-C_6)$alkyl, aryl and aryl-substituted $(C_1-C_6)$alkyl;
$R^{16}$ is $(C_1-C_6)$alkyl, aryl or $R^{17}$-substituted aryl;
$R^{18}$ is hydrogen or $(C_1-C_6)$alkyl; and
$R^{19}$ is hydrogen, hydroxy or $(C_1-C_6)$alkoxy.

As used in Formula (IV) above, "A" is preferably an $R^2$-substituted, 6-membered heterocycloalkyl ring containing 1 or 2 nitrogen atoms. Preferred heterocycloalkyl rings are piperidinyl, piperazinyl and morpholinyl groups. The ring "A" is preferably joined to the phenyl ring through a ring nitrogen. Preferred $R^2$ substituents are hydrogen and lower alkyl. $R^{19}$ is preferably hydrogen.

$Ar^2$ is preferably phenyl or $R^4$-phenyl, especially (4-$R^4$)-substituted phenyl. Preferred definitions of $R^4$ are lower alkoxy, especially methoxy, and halogeno, especially fluoro.
$Ar^1$ is preferably phenyl or $R^3$-substituted phenyl, especially (4-$R^3$)-substituted phenyl.

There are several preferred definitions for the —$R^1$—Q— combination of variables:
Q is a bond and $R^1$ is lower alkylene, preferably propylene;
Q is a spiro group as defined above, wherein preferably $R^6$ and $R^7$ are each ethylene and $R^5$ is —CH—  or  —C(OH)—;

Q is a bond and $R^1$ is

—M—$Y_d$—C($R^{10}$)($R^{11}$)—$Z_h$— wherein the variables are chosen such that $R^1$ is —O—$CH_2$—CH(OH)—;
Q is a bond and $R^1$ is —$X_m$—(C)$_s$($R^{12}$)($R^{13}$)—$Y_n$—(C)$_t$($R^{10}$)($R^{11}$)—$Z_p$— wherein the variables are chosen such that $R^1$ is —CH(OH)—$(CH_2)_2$—; and
Q is a bond and $R^1$ is —$X_j$—(C)$_v$($R^{10}$)($R^{11}$)—$Y_k$—$S(O)_{0-2}$— wherein the variables are chosen such that $R^1$ is —CH(OH)—$CH_2$—$S(O)_{0-2}$.

Methods for making compounds of Formula IV are well known to those skilled in the art. Non-limiting examples of suitable methods are disclosed in U.S. Pat. No. 5,656,624, which is incorporated herein by reference.

In another embodiment, sterol absorption inhibitors useful in the compositions, therapeutic combinations and methods of the present invention are represented by Formula (V):

(V)
[structure showing $Ar^1$, $X_m$, (C)$_q$($R$)($R^1$), $Y_n$, $S(O)_r$, $Ar^2$, azetidinone with $Ar^3$]

or isomers of the compounds of Formula (V), or pharmaceutically acceptable salts or solvates of the compounds of Formula (V) or of the isomers of the compounds of Formula (V), or prodrugs of the compounds of Formula (V) or of the isomers, salts or solvates of the compounds of Formula (V), wherein, in Formula (V) above:
$Ar^1$ is aryl, $R^{10}$-substituted aryl or heteroaryl;
$Ar^2$ is aryl or $R^4$-substituted aryl;
$Ar^3$ is aryl or $R^5$-substituted aryl;
X and Y are independently selected from the group consisting of —$CH_2$—, —CH(lower alkyl)- and —C(dilower alkyl)-;
R is —$OR^6$, —$O(CO)R^6$, —$O(CO)OR^9$ or —$O(CO)NR^6R^7$; $R^1$ is hydrogen, lower alkyl or aryl; or R and $R^1$ together are =O;
q is 0 or 1;
r is 0, 1 or 2;

m and n are independently 0, 1, 2, 3, 4 or 5; provided that the sum of m, n and q is 1, 2, 3, 4 or 5;

$R^4$ is 1–5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$-$COOR^6$, —$O(CH_2)_{1-10}CONR^6R^7$, -(lower alkylene)$COOR^6$ and —CH=CH—$COOR^6$;

$R^5$ is 1–5 substituents independently selected from the group consisting of —$OR^6$, —$O(CO)R^6$, —$O(CO)OR^9$, —$O(CH_2)_{1-5}OR^6$, —$O(CO)NR^6R^7$, —$NR^6R^8$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, —$SO_2NR^6R^7$, $S(O)_{0-2}R^9$, —$O(CH_2)_{1-10}$—$COOR^6$, —$O(CH_2)_{1-10}CONR^6R^7$, —$CF_3$, —CN, —$NO_2$, halogen, -(lower alkylene)COOR and —CH=CH—$COOR^6$;

$R^6$, $R^7$ and $R^8$ are independently selected from the group consisting of hydrogen, lower alkyl, aryl and aryl-substituted lower alkyl;

$R^9$ is lower alkyl, aryl or aryl-substituted lower alkyl; and $R^{10}$ is 1–5 substituents independently selected from the group consisting of lower alkyl, —$OR^6$, —$O(CO)R^6$, —$O(CO)OR^9$, —$O(CH_2)_{1-5}OR^6$, —$O(CO)NR^6R^7$, —$NR^6R^7$, —$NR^6(CO)R^7$, —$NR^6(CO)OR^9$, —$NR^6(CO)NR^7R^8$, —$NR^6SO_2R^9$, —$COOR^6$, —$CONR^6R^7$, —$COR^6$, $SO_2NR^6R^7$, —$S(O)_{0-2}R^9$, —$O(CH_2)_{1-10}$—$COOR^6$, —$O(CH_2)_{1-10}CONR^6R^7$, —$CF_3$, —CN, —$NO_2$ and halogen.

Within the scope of Formula V, there are included two preferred structures. In Formula VA, q is zero and the remaining variables are as defined above, and in Formula VB, q is 1 and the remaining variables are as defined above:

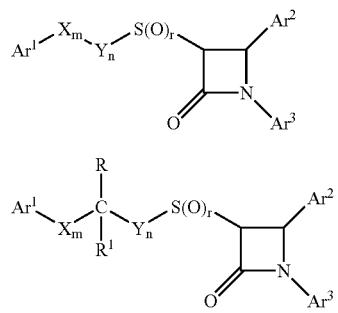

$R^4$, $R^5$ and $R^{10}$ are each preferably 1–3 independently selected substituents as set forth above. Preferred are compounds of Formula (V) wherein $Ar^1$ is phenyl, $R^{10}$-substituted phenyl or thienyl, especially (4-$R^{10}$)-substituted phenyl or thienyl. $Ar^2$ is preferably $R^4$-substituted phenyl, especially (4-$R^4$)-substituted phenyl. $Ar^3$ is preferably phenyl or $R_5$-substituted phenyl, especially (4-$R_5$)-substituted phenyl. When $Ar^1$ is $R^{10}$-substituted phenyl, $R^{10}$ is preferably halogeno, especially fluoro. When $Ar^2$ is $R^4$-substituted phenyl, $R^4$ is preferably —$OR^6$, especially wherein $R^6$ is hydrogen or lower alkyl. When $Ar^3$ is $R^5$-substituted phenyl, $R^5$ is preferably halogeno, especially fluoro. Especially preferred are compounds of Formula (V) wherein $Ar^1$ is phenyl, 4-fluorophenyl or thienyl, $Ar^2$ is 4-(alkoxy or hydroxy)phenyl, and $Ar^3$ is phenyl or 4-fluorophenyl.

X and Y are each preferably —$CH_2$—. The sum of m, n and q is preferably 2, 3 or 4, more preferably 2. When q is 1, n is preferably 1 to 5.

Preferences for X, Y, $Ar^1$, $Ar^2$ and $Ar^3$ are the same in each of Formulae (VA) and (VB).

In compounds of Formula (VA), the sum of m and n is preferably 2, 3 or 4, more preferably 2. Also preferred are compounds wherein the sum of m and n is 2, and r is 0 or 1.

In compounds of Formula (VB), the sum of m and n is preferably 1, 2 or 3, more preferably 1. Especially preferred are compounds wherein m is zero and n is 1. $R^1$ is preferably hydrogen and R is preferably —$OR^6$ wherein $R^6$ is hydrogen, or a group readily metabolizable to a hydroxyl (such as —$O(CO)R^6$, —$O(CO)OR^9$ and —$O(CO)NR^6R^7$, defined above), or R and $R^1$ together form a =O group.

Methods for making compounds of Formula V are well known to those skilled in the art. Non-limiting examples of suitable methods are disclosed in U.S. Pat. No. 5,624,920, which is incorporated herein by reference.

In another embodiment, sterol absorption inhibitors useful in the compositions, therapeutic combinations and methods of the present invention are represented by Formula (VI):

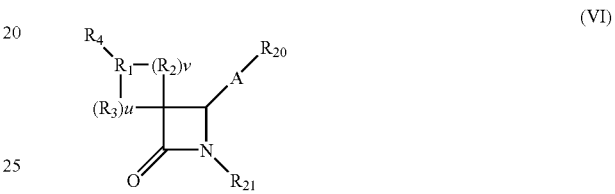

or isomers of the compounds of Formula (VI), or pharmaceutically acceptable salts or solvates of the compounds of Formula (VI) or of the isomers of the compounds of Formula (VI), or prodrugs of the compounds of Formula (VI) or of the isomers, salts or solvates of the compounds of Formula (VI), wherein:

$R_1$ is

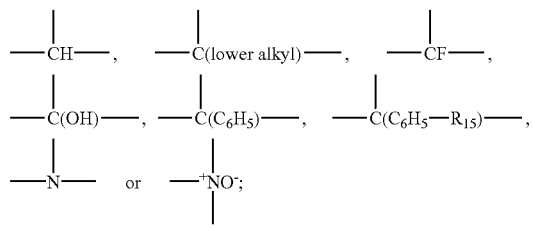

$R_2$ and $R_3$ are independently selected from the group consisting of: —$CH_2$—, —CH(lower alkyl)-, —C(di-lower alkyl)-, —CH=CH— and —C(lower alkyl)=CH—; or $R_1$ together with an adjacent $R_2$, or $R_1$ together with an adjacent $R_3$, form a —CH=CH— or a —CH=C(lower alkyl)- group;

u and v are independently 0, 1, 2 or 3, provided both are not zero; provided that when $R_2$ is —CH=CH— or —C(lower alkyl)=CH—, v is 1; provided that when $R_3$ is —CH=CH— or —C(lower alkyl)=CH—, u is 1; provided that when v is 2 or 3, the $R_2$'s can be the same or different; and provided that when u is 2 or 3, the $R_3$'s can be the same or different;

$R_4$ is selected from B—$(CH_2)_mC(O)$—, wherein m is 0, 1, 2, 3, 4 or 5; B—$(CH_2)_q$—, wherein q is 0, 1, 2, 3, 4, 5 or 6; B—$(CH_2)_e$—Z—$(CH_2)_r$—, wherein Z is —O—, —C(O)—, phenylene, —N($R_8$)— or —$S(O)_{0-2}$—, e is 0, 1, 2, 3, 4 or 5 and r is 0, 1, 2, 3, 4 or 5, provided that the sum of e and r is 0, 1, 2, 3, 4, 5 or 6; B—($C_2$–$C_6$ alkenylene)-; B—($C_4$–$C_6$ alkadienylene)-; B—$(CH_2)_t$—Z—($C_2$–$C_6$ alkenylene), wherein Z is as defined above, and wherein t is 0, 1, 2 or 3, provided that the sum of t and the number of carbon atoms in the alkenylene chain is 2, 3, 4, 5 or 6; B—$(CH_2)_f$—V—$(CH_2)_g$—, wherein V is $C_3$–$C_6$ cycloalkylene, f is 1, 2, 3, 4 or 5 and g is 0, 1, 2, 3, 4 or 5, provided that the sum of f and g is 1, 2, 3, 4, 5 or 6; B—$(CH_2)_t$—V—$(C_2$–$C_6$ alkenylene) or B—$(C_2$–$C_6$ alkenylene)—V—$(CH_2)_t$—, wherein V and t are as defined above, provided that the sum of t and the number of carbon atoms in the alkenylene chain is 2, 3, 4, 5 or 6; B—$(CH_2)_a$—Z—$(CH_2)_b$—V—$(CH_2)_d$—, wherein Z and V are as defined above and a, b and d are independently 0, 1, 2, 3, 4, 5 or 6, provided that the sum of a, b and d is 0, 1, 2, 3, 4, 5 or 6; or T—$(CH_2)_s$—, wherein T is cycloalkyl of 3–6 carbon atoms and s is 0, 1, 2, 3, 4, 5 or 6; or $R_1$ and $R_4$ together form the group

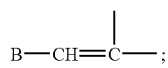

B is selected from indanyl, indenyl, naphthyl, tetrahydronaphthyl, heteroaryl or W-substituted heteroaryl, wherein heteroaryl is selected from the group consisting of pyrrolyl, pyridinyl, pyrimidinyl, pyrazinyl, triazinyl, imidazolyl, thiazolyl, pyrazolyl, thienyl, oxazolyl and furanyl, and for nitrogen-containing heteroaryls, the N-oxides thereof, or

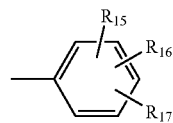

W is 1 to 3 substituents independently selected from the group consisting of lower alkyl, hydroxy lower alkyl, lower alkoxy, alkoxyalkyl, alkoxyalkoxy, alkoxycarbonylalkoxy, (lower alkoxyimino)-lower alkyl, lower alkanedioyl, lower alkyl lower alkanedioyl, allyloxy, —$CF_3$, —$OCF_3$, benzyl, $R_7$-benzyl, benzyloxy, $R_7$-benzyloxy, phenoxy, $R_7$-phenoxy, dioxolanyl, $NO_2$, —$N(R_8)(R_9)$, $N(R_8)(R_9)$-lower alkylene-, $N(R_8)(R_9)$-lower alkylenyloxy-, OH, halogeno, —CN, —$N_3$, —$NHC(O)OR_{10}$, —$NHC(O)R_{10}$, $R_{11}O_2SNH$—, $(R_{11}O_2S)_2N$—, —$S(O)_2NH_2$, —$S(O)_{0-2}R_8$, tert-butyldimethyl-silyloxymethyl, —$C(O)R_{12}$, —$COOR_{19}$, —$CON(R_8)(R_9)$, —CH=$CHC(O)R_{12}$, -lower alkylene-C$(O)R_{12}$, $R_{10}C(O)$(lower alkylenyloxy)-, $N(R_8)(R_9)C(O)$(lower alkylenyloxy)- and

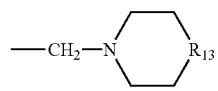

for substitution on ring carbon atoms, and the substituents on the substituted heteroaryl ring nitrogen atoms, when present, are selected from the group consisting of lower alkyl, lower alkoxy, —$C(O)OR_{10}$, —$C(O)R_{10}$, OH, $N(R_8)(R_9)$-lower alkylene-, $N(R_8)(R_9)$-lower alkylenyloxy-, —$S(O)_2NH_2$ and 2-(trimethylsilyl)-ethoxymethyl;

$R_7$ is 1–3 groups independently selected from the group consisting of lower alkyl, lower alkoxy, —COOH, $NO_2$, —$N(R_8)(R_9)$, OH, and halogeno;

$R_8$ and $R_9$ are independently selected from H or lower alkyl;

$R_{10}$ is selected from lower alkyl, phenyl, $R_7$-phenyl, benzyl or $R_7$-benzyl;

$R_{11}$ is selected from OH, lower alkyl, phenyl, benzyl, $R_7$-phenyl or $R_7$-benzyl;

$R_{12}$ is selected from H, OH, alkoxy, phenoxy, benzyloxy,

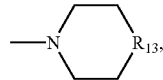

—$N(R_8)(R_9)$, lower alkyl, phenyl or $R_7$-phenyl;

$R_{13}$ is selected from —O—, —$CH_2$—, —NH—, —N(lower alkyl)- or —$NC(O)R_{19}$;

$R_{15}$, $R_{16}$ and $R_{17}$ are independently selected from the group consisting of H and the groups defined for W; or $R_{15}$ is hydrogen and $R_{16}$ and $R_{17}$, together with adjacent carbon atoms to which they are attached, form a dioxolanyl ring;

$R_{19}$ is H, lower alkyl, phenyl or phenyl lower alkyl; and $R_{20}$ and $R_{21}$ are independently selected from the group consisting of phenyl, W-substituted phenyl, naphthyl, W-substituted naphthyl, indanyl, indenyl, tetrahydronaphthyl, benzodioxolyl, heteroaryl, W-substituted heteroaryl, benzofused heteroaryl, W-substituted benzofused heteroaryl and cyclopropyl, wherein heteroaryl is as defined above.

One group of preferred compounds of Formula VI is that in which R21 is selected from phenyl, W-substituted phenyl, indanyl, benzofuranyl, benzodioxolyl, tetrahydronaphthyl, pyridyl, pyrazinyl, pyrimidinyl, quinolyl or cyclopropyl, wherein W is lower alkyl, lower alkoxy, OH, halogeno, —$N(R_8)(R_9)$, —$NHC(O)OR_{10}$, —$NHC(O)R_{10}$, $NO_2$, —CN, —$N_3$, —SH, —$S(O)_{0-2}$-(lower alkyl), —$COOR_{19}$, —$CON(R_8)(R_9)$, —$COR_{12}$, phenoxy, benzyloxy, —$OCF_3$, —CH=$C(O)R_{12}$ or tert-butyldimethylsilyloxy, wherein $R_8$, $R_9$, $R_{10}$, $R_{12}$ and $R_{19}$ are as defined for Formula IV. When W is 2 or 3 substituents, the substituents can be the same or different.

Another group of preferred compounds of Formula VI is that in which $R_{20}$ is phenyl or W-substituted phenyl, wherein preferred meanings of W are as defined above for preferred definitions of $R_{21}$.

More preferred are compounds of Formula VI wherein $R_{20}$ is phenyl or W-substituted phenyl and $R_{21}$ is phenyl, W-substituted phenyl, indanyl, benzofuranyl, benzodioxolyl, tetrahydronaphthyl, pyridyl, pyrazinyl, pyrimidinyl, quinolyl or cyclopropyl; W is lower alkyl, lower alkoxy, OH, halogeno, —$N(R_8)(R_9)$, —NHC(O)$OR_{10}$, —$NHC(O)R_{10}$, $NO_2$, —CN, —$N_3$, —SH, —$S(O)_{0-2}$-(lower alkyl), —$COOR_{19}$, —$CON(R_8)(R_9)$, —$COR_{12}$, phenoxy, benzyloxy, —CH=$CHC(O)R_{12}$, —$OCF_3$ or tert-butyl-dimethyl-silyloxy, wherein when W is 2 or 3 substituents, the substituents can be the same or different, and wherein $R_8$, $R_9$, $R_{10}$, $R_{12}$ and $R_{19}$ are as defined in Formula VI.

Also preferred are compounds of Formula VI wherein $R_1$ is

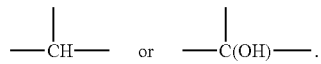

Another group of preferred compounds of Formula VI is in which $R_2$ and $R_3$ are each —$CH_2$— and the sum of u and v is 2, 3 or 4, with u=v=2 being more preferred.

$R_4$ is preferably B—$(CH_2)_q$— or B—$(CH_2)_e$—Z—$(CH_2)_r$—, wherein B, Z, q, e and r are as defined above. B is preferably

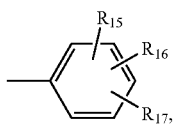

wherein $R_{16}$ and $R_{17}$ are each hydrogen and wherein $R_{15}$ is preferably H, OH, lower alkoxy, especially methoxy, or halogeno, especially chloro.

Preferably Z is —O—, e is 0, and r is 0.

Preferably q is 0–2.

$R_{20}$ is preferably phenyl or W-substituted phenyl.

Preferred W substituents for $R_{20}$ are lower alkoxy, especially methoxy and ethoxy, OH, and —C(O)$R_{12}$, wherein $R_{12}$ is preferably lower alkoxy.

Preferably $R_{21}$ is selected from phenyl, lower alkoxy-substituted phenyl and F-phenyl.

Especially preferred are compounds of Formula VI wherein $R_1$ is

or

$R_2$ and $R_3$ are each —CH$_2$—, u=v=2, $R_4$ is B—(CH$_2$)$_q$—, wherein B is phenyl or phenyl substituted by lower alkoxy or chloro, q is 0–2, $R_{20}$ is phenyl, OH-phenyl, lower alkoxy-substituted phenyl or lower alkoxycarbonyl-substituted phenyl, and $R_{21}$ is phenyl, lower alkoxy-substituted phenyl or F-phenyl.

Methods for making compounds of Formula VI are well known to those skilled in the art. Non-limiting examples of suitable methods are disclosed in U.S. Pat. No. 5,698,548, which is incorporated herein by reference.

In another embodiment, sterol inhibitors useful in the compositions, therapeutic combinations and methods of the present invention are represented by Formula (VII):

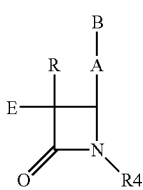

(VII)

or isomers of the compounds of Formula (VII), or pharmaceutically acceptable salts or solvates of the compounds of Formula (VII) or of the isomers of the compounds of Formula (VII), or prodrugs of the compounds of Formula (VII) or of the isomers, salts or solvates of the compounds of Formula (VII), wherein in Formula (VII) above:

A is —CH=CH—, —C≡C— or —(CH$_2$)$_p$— wherein p is 0, 1 or 2;

B is

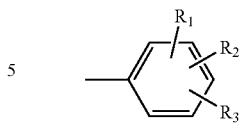

E is $C_{10}$ to $C_{20}$ alkyl or —C(O)—($C_9$ to $C_{19}$)-alkyl, wherein the alkyl is straight or branched, saturated or containing one or more double bonds;

R is hydrogen, $C_1$–$C_{15}$ alkyl, straight or branched, saturated or containing one or more double bonds, or B—(CH$_2$)$_r$—, wherein r is 0, 1, 2, or 3;

$R_1$, $R_2$, and $R_3$ are independently selected from the group consisting of hydrogen, lower alkyl, lower alkoxy, carboxy, NO$_2$, NH$_2$, OH, halogeno, lower alkylamino, dilower alkylamino, —NHC(O)OR$_5$, $R_6$O$_2$SNH— and —S(O)$_2$NH$_2$;

$R_4$ is

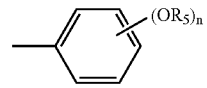

wherein n is 0, 1, 2 or 3;

$R_5$ is lower alkyl; and $R_6$ is OH, lower alkyl, phenyl, benzyl or substituted phenyl wherein the substituents are 1–3 groups independently selected from the group consisting of lower alkyl, lower alkoxy, carboxy, NO$_2$, NH$_2$, OH, halogeno, lower alkylamino and dilower alkylamino.

Preferred compounds of Formula (VII) are those wherein R is hydrogen, methyl, ethyl, phenyl or phenylpropyl. Another group of preferred compounds of Formula (VII) is that wherein $R_4$ is p-methoxyphenyl or 2,4,6-trimethoxyphenyl. Still another group of preferred compounds of Formula (VII) is that wherein A is ethylene or a bond. Yet another group of preferred compounds of Formula (VII) is that wherein E is decyl, oleoyl or 7-Z-hexadecenyl. Preferably $R_1$, $R_2$ and $R_3$ are each hydrogen.

More preferred compounds of Formula (VII) are those wherein R is hydrogen, methyl, ethyl, phenyl or phenylpropyl; $R_4$ is p-methoxyphenyl or 2,4,6-trimethoxyphenyl; A is ethylene or a bond; E is decyl, oleoyl or 7-Z-hexadecenyl; and $R_1$, $R_2$ and $R_3$ are each hydrogen.

A preferred compound of Formula (VII) is that wherein E is decyl, R is hydrogen, B–A is phenyl and $R_4$ is p-methoxyphenyl.

In another embodiment, sterol inhibitors useful in the compositions and methods of the present invention are represented by Formula (VIII):

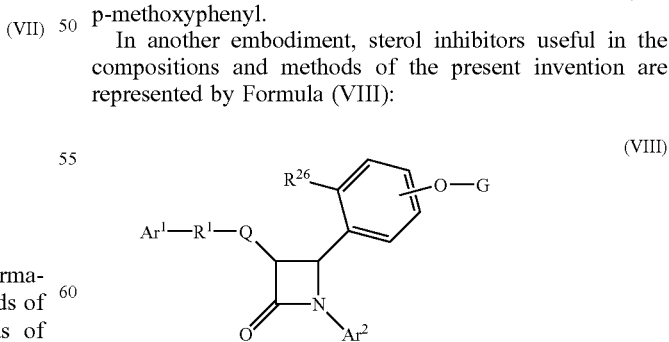

(VIII)

or isomers of the compounds of Formula (VIII), or pharmaceutically acceptable salts or solvates of the compounds of Formula (VIII) or of the isomers of the compounds of Formula (VIII), or prodrugs of the compounds of Formula (VIII) or of the isomers, salts or solvates of the compounds of Formula (VIII), wherein, in Formula (VIII) above, $R^{26}$ is H or $OG^1$;

G and $G^1$ are independently selected from the group consisting of

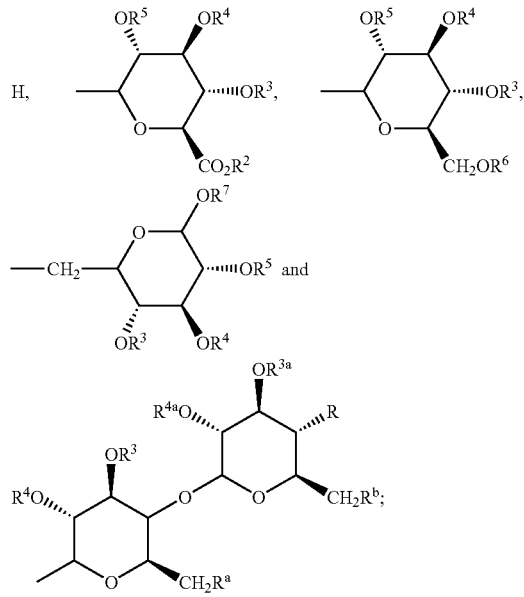

provided that when $R^{26}$ is H or OH, G is not H;

R, $R^a$ and $R^b$ are independently selected from the group consisting of H, —OH, halogeno, —$NH_2$, azido, $(C_1-C_6)$alkoxy$(C_1-C_6)$-alkoxy or —W—$R^{30}$;

W is independently selected from the group consisting of —NH—C(O)—, —O—C(O)—, —O—C(O)—N($R^{31}$)—, —NH—C(O)—N($R^{31}$)— and —O—C(S)—N($R^{31}$)—;

$R^2$ and $R^6$ are independently selected from the group consisting of H, $(C_1-C_6)$alkyl, aryl and aryl$(C_1-C_6)$alkyl;

$R^3$, $R^4$, $R^5$, $R^7$, $R^{3a}$ and $R^{4a}$ are independently selected from the group consisting of H, $(C_1-C_6)$alkyl, aryl$(C_1-C_6)$alkyl, —C(O)$(C_1-C_6)$alkyl and —C(O)aryl;

$R^{30}$ is selected from the group consisting of $R^{32}$-substituted T, $R^{32}$-substituted-T—$(C_1-C_6)$alkyl, $R^{32}$-substituted-$(C_2-C_4)$alkenyl, $R^{32}$-substituted-$(C_1-C_6)$alkyl, $R^{32}$-substituted-$(C_3-C_7)$cycloalkyl and $R^{32}$-substituted-$(C_3-C_7)$cycloalkyl$(C_1-C_6)$alkyl;

$R^{31}$ is selected from the group consisting of H and $(C_1-C_4)$alkyl;

T is selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

$R^{32}$ is independently selected from 1–3 substituents independently selected from the group consisting of halogeno, $(C_1-C_4)$alkyl, —OH, phenoxy, —$CF_3$, —$NO_2$, $(C_1-C_4)$alkoxy, methylenedioxy, oxo, $(C_1-C_4)$alkylsulfanyl, $(C_1-C_4)$alkylsulfinyl, $(C_1-C_4)$alkylsulfonyl, —N$(CH_3)_2$, —C(O)—NH$(C_1-C_4)$alkyl, —C(O)—N$((C_1-C_4)$alkyl$)_2$, —C(O)—$(C_1-C_4)$alkyl, —C(O)—$(C_1-C_4)$alkoxy and pyrrolidinylcarbonyl; or $R^{32}$ is a covalent bond and $R^{31}$, the nitrogen to which it is attached and $R^{32}$ form a pyrrolidinyl, piperidinyl, N-methyl-piperazinyl, indolinyl or morpholinyl group, or a $(C_1-C_4)$alkoxycarbonyl-substituted pyrrolidinyl, piperidinyl, N-methylpiperazinyl, indolinyl or morpholinyl group;

$Ar^1$ is aryl or $R^{10}$-substituted aryl;

$Ar^2$ is aryl or $R^{11}$-substituted aryl;

Q is a bond or, with the 3-position ring carbon of the azetidinone, forms the spiro group

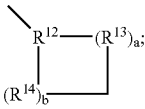

and $R^1$ is selected from the group consisting of

—$(CH_2)_q$—, wherein q is 2–6, provided that when Q forms a spiro ring, q can also be zero or 1;

—$(CH_2)_e$—E—$(CH_2)_r$—, wherein E is —O—, —C(O)—, phenylene, —$NR^{22}$— or —$S(O)_{0-2}$—, e is 0–5 and r is 0–5, provided that the sum of e and r is 1–6;

—$(C_2-C_6)$alkenylene-; and

—$(CH_2)_f$—V—$(CH_2)_g$—, wherein V is $C_3-C_6$ cycloalkylene, f is 1–5 and g is 0–5, provided that the sum of f and g is 1–6;

$R^{12}$ is

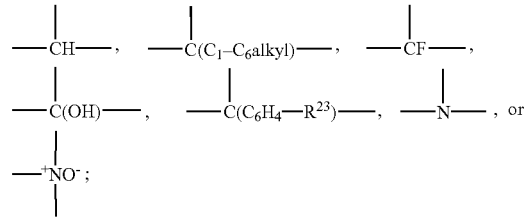

$R^{13}$ and $R^{14}$ are independently selected from the group consisting of

—$CH_2$—, —CH$(C_1-C_6$ alkyl)-, —C(di-$(C_1-C_6)$ alkyl), —CH=CH— and —C$(C_1-C_6$ alkyl)=CH—; or $R^{12}$ together with an adjacent $R^{13}$, or $R^{12}$ together with an adjacent $R^{14}$, form a —CH=CH— or a —CH=C$(C_1-C_6$ alkyl)-group;

a and b are independently 0, 1, 2 or 3, provided both are not zero;

provided that when $R^{13}$ is —CH=CH— or —C$(C_1-C_6$ alkyl)=CH—, a is 1;

provided that when $R^{14}$ is —CH=CH— or —C$(C_1-C_6$ alkyl)=CH—, b is 1;

provided that when a is 2 or 3, the $R^{13}$'s can be the same or different; and provided that when b is 2 or 3, the $R^{14}$'s can be the same or different;

and when Q is a bond, $R^1$ also can be:

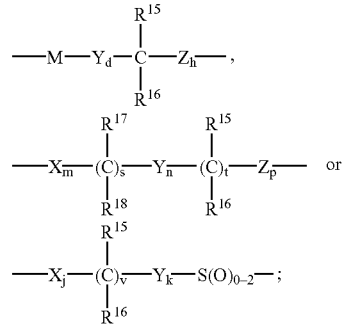

M is —O—, —S—, —S(O)— or —$S(O)_2$—;

X, Y and Z are independently selected from the group consisting of —$CH_2$—, —CH$(C_1-C_6)$alkyl- and —C(di-$(C_1-C_6)$alkyl);

$R^{10}$ and $R^{11}$ are independently selected from the group consisting of 1–3 substituents independently selected from the group consisting of $(C_1-C_6)$alkyl, $-OR^{19}$, $-O(CO)R^{19}$, $-O(CO)OR^{21}$, $-O(CH_2)_{1-5}OR^{19}$, $-O(CO)NR^{19}R^{20}$, $-NR^{19}R^{20}$, $-NR^{19}(CO)R^{20}$, $-NR^{19}(CO)OR^{21}$, $-NR^{19}(CO)NR^{2}OR^{25}$, $-NR^{19}SO_2R^{21}$, $-COOR^{19}$, $-CONR^{19}R^{20}$, $-COR^{19}$, $-SO_2NR^{19}R^{20}$, $S(O)_{0-2}R^{21}$, $-O(CH_2)_{1-10}-COOR^{19}$, $-O(CH_2)_{1-10}CONR^{19}R^{20}$, $-(C_1-C_6\ \text{alkylene})-COOR^{19}$, $-CH=CH-COOR^{19}$, $-CF_3$, $-CN$, $-NO_2$ and halogen;

$R^{15}$ and $R^{17}$ are independently selected from the group consisting of $-OR^{19}$, $-O(CO)R^{19}$, $-O(CO)OR^{21}$ and $-O(CO)NR^{19}R^{20}$;

$R^{16}$ and $R^{18}$ are independently selected from the group consisting of H, $(C_1-C_6)$alkyl and aryl; or $R^{15}$ and $R^{16}$ together are =O, or $R^{17}$ and $R^{18}$ together are =O;

d is 1, 2 or 3;

h is 0, 1, 2, 3 or 4;

s is 0 or 1; t is 0 or 1; m, n and p are independently 0–4;

provided that at least one of s and t is 1, and the sum of m, n, p, s and t is 1–6;

provided that when p is 0 and t is 1, the sum of m, s and n is 1–5; and provided that when p is 0 and s is 1, the sum of m, t and n is 1–5;

v is 0 or 1;

j and k are independently 1–5, provided that the sum of j, k and v is 1–5;

and when Q is a bond and $R^1$ is $$-X_j-(C)_v-Y_k-S(O)_{0-2}-,$$
with $R^{15}$ above and $R^{16}$ below the central C, $Ar^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, $-C(O)R^{19}$ or $-COOR^{19}$;

$R^{23}$ and $R^{24}$ are independently 1–3 groups independently selected from the group consisting of H, $(C_1-C_6)$alkyl, $(C_1-C_6)$alkoxy, $-COOH$, $NO_2$, $-NR^{19}R^{20}$, $-OH$ and halogeno; and $R^{25}$ is H, $-OH$ or $(C_1-C_6)$alkoxy.

$Ar^2$ is preferably phenyl or $R^{11}$-phenyl, especially $(4-R^{11})$-substituted phenyl. Preferred definitions of $R^{11}$ are lower alkoxy, especially methoxy, and halogeno, especially fluoro.

$Ar^1$ is preferably phenyl or $R^{10}$-substituted phenyl, especially $(4-R^{10})$-substituted phenyl. Preferably $R^{10}$ is halogeno, and more preferably fluoro.

There are several preferred definitions for the $-R^1-Q-$ combination of variables:

Q is a bond and $R^1$ is lower alkylene, preferably propylene;

Q is a spiro group as defined above, wherein preferably $R^{13}$ and $R^{14}$ are each ethylene and $R^{12}$ is $$-\underset{|}{CH}-\quad \text{or} \quad -\underset{|}{C(OH)}-,$$

and $R^1$ is $-(CH_2)_q$ wherein q is 0–6;

Q is a bond and $R^1$ is $$-M-Y_d-\underset{R^{16}}{\overset{R^{15}}{\underset{|}{\overset{|}{C}}}}-Z_h-$$

wherein the variables are chosen such that $R^1$ is $-O-CH_2-CH(OH)-$;

Q is a bond and $R^1$ $$-X_m-(C)_s-Y_n-(C)_t-Z_p-$$
with $R^{17}$ and $R^{18}$ on the first C and $R^{15}$ and $R^{16}$ on the second C, wherein the variables are chosen such that $R^1$ is $-CH(OH)-(CH_2)_2-$; and Q is a bond and $R^1$ is $$-X_j-(C)_v-Y_k-S(O)_{0-2}-$$
with $R^{15}$ above and $R^{16}$ below the C, wherein the variables are chosen such that $R^1$ is $-CH(OH)-CH_2-S(O)_{0-2}-$.

A preferred compound of Formula (VIII) therefore, is one wherein G and $G^1$ are as defined above and in which the remaining variables have the following definitions:

$Ar^1$ is phenyl or $R^{10}$-substituted phenyl, wherein $R^{10}$ is halogeno;

$Ar^2$ is phenyl or $R^{11}$-phenyl, wherein $R^{11}$ is 1 to 3 substituents independently selected from the group consisting of $C_1-C_6$ alkoxy and halogeno;

Q is a bond and $R^1$ is lower alkylene; Q, with the 3-position ring carbon of the azetidinone, forms the group $$\underset{(R^{14})_b}{\overset{R^{12}-(R^{13})_a}{\diagdown|\diagup}}$$

wherein preferably $R^{13}$ and $R^{14}$ are each ethylene and a and b are each 1, and wherein $R^{12}$ is $$-\underset{|}{CH}-,\quad \text{or} \quad -\underset{|}{C(OH)}-;$$

Q is a bond and $R^1$ is $-O-CH_2-CH(OH)-$; Q is a bond and $R^1$ is $-CH(OH)-(CH_2)_2-$; or Q is a bond and $R^1$ is $-CH(OH)-CH_2-S(O)_{0-2}-$.

Preferred variables for G and $G^1$ groups of the formulae (pyranose structures with $OR^5$, $OR^4$, $OR^3$, $CO_2R^2$ and $OR^5$, $OR^4$, $OR^3$, $CH_2OR^6$) and

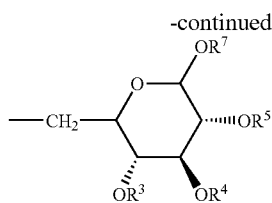

are as follows:

$R^2$, $R^3$, $R^4$, $R^5$, $R^6$ and $R^7$ are independently selected from the group consisting of H, $(C_1-C_6)$alkyl, benzyl and acetyl.

Preferred variables for group G or $G^1$ of the formula:

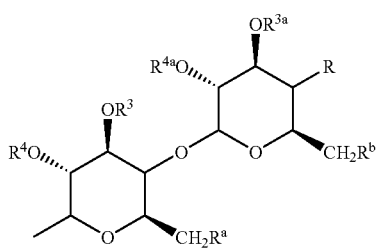

are as follows:

$R^3$, $R^{3a}$, $R^4$ and $R^{4a}$ are selected from the group consisting of H, $(C_1-C_6)$alkyl, benzyl and acetyl;

R, $R^a$ and $R^b$ are independently selected from the group consisting of H, —OH, halogeno, —NH$_2$, azido, $(C_1-C_6)$alkoxy$(C_1-C_6)$alkoxy and —W—$R^{30}$, wherein W is —O—C(O)— or —O—C(O)—NR$^{31}$—, $R^{31}$ is H and $R^{30}$ is $(C_1-C_6)$alkyl, —C(O)—$(C_1-C_4)$alkoxy-$(C_1-C_6)$alkyl, T, T—$(C_1-C_6)$alkyl, or T or T—$(C_1-C_6)$alkyl wherein T is substituted by one or two halogeno or $(C_1-C_6)$ alkyl groups.

Preferred $R^{30}$ substituents are selected from the group consisting of: 2-fluorophenyl, 2,4-difluoro-phenyl, 2,6-dichlorophenyl, 2-methylphenyl, 2-thienylmethyl, 2-methoxy-carbonylethyl, thiazol-2-yl-methyl, 2-furyl, 2-methoxycarbonylbutyl and phenyl.

Preferred combinations of R, $R^a$ and $R^b$ are as follows:

1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are each —OH and $R^b$ is —O—C(O)—NH—$R^{30}$ wherein $R^{30}$ is 2-fluorophenyl, 2,4-difluoro-phenyl, 2,6-dichlorophenyl;

2) $R^a$ is —OH, halogeno, azido or $(C_1-C_6)$-alkoxy$(C_1-C_6)$alkoxy, $R^b$ is H, halogeno, azido or $(C_1-C_6)$alkoxy$(C_1-C_6)$-alkoxy, and R is —O—C(O)—NH—$R^{30}$, especially compounds wherein $R^a$ is —OH, $R^b$ is H and $R^{30}$ is 2-fluorophenyl;

3) R, $R^a$ and $R^b$ are independently —OH or —O—C(O)—$R^{30}$ and $R^{30}$ is $(C_1-C_6)$alkyl, T, or T substituted by one or two halogeno or $(C_1-C_6)$alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred compounds are those wherein the $C^{1'}$ anomeric oxy is beta, wherein the $C^{2'}$ anomeric oxy is beta, and wherein the R group is alpha. G and $G^1$ are preferably selected from:

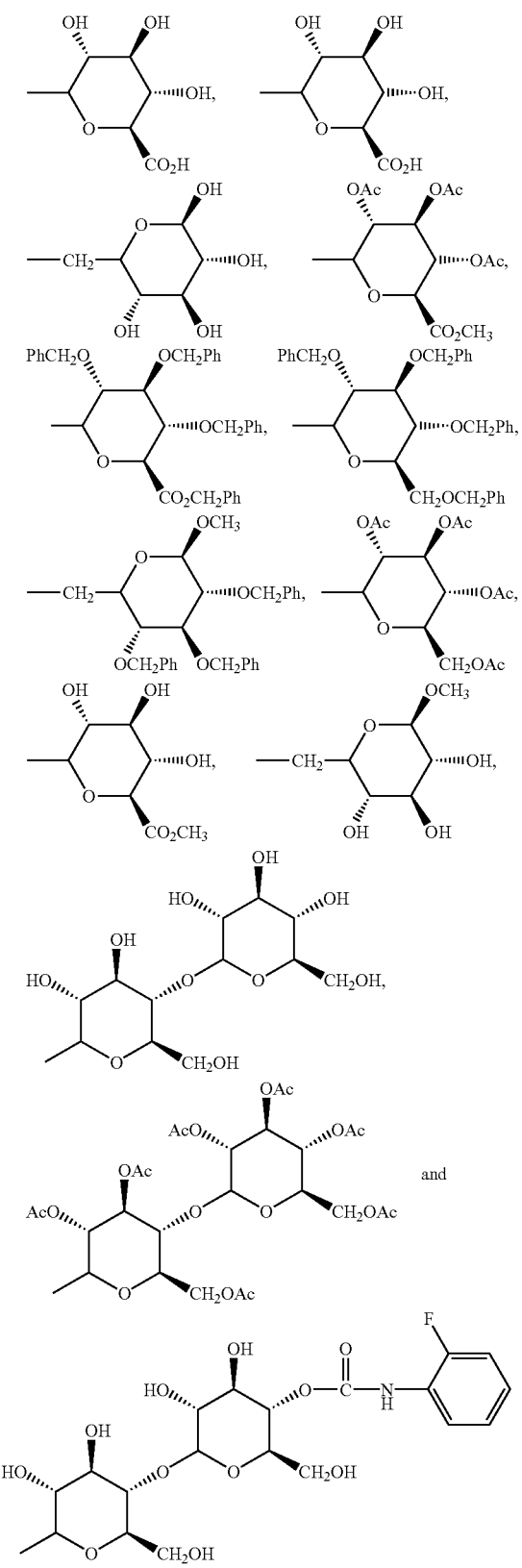

wherein Ac is acetyl and Ph is phenyl.

Preferably, $R^{26}$ is H or OH, more preferably H. The —O—G substituent is preferably in the 4-position of the phenyl ring to which it is attached.

In another embodiment, sterol inhibitors useful in the compositions and methods of the present invention are represented by Formula (IX) below:

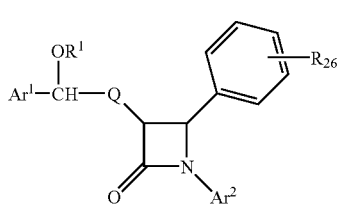

(IX)

or isomers of the compounds of Formula (IX), or pharmaceutically acceptable salts or solvates of the compounds of Formula (IX) or of the isomers of the compounds of Formula (IX), or prodrugs of the compounds of Formula (IX) or of the isomers, salts or solvates of the compounds of Formula (IX), wherein in Formula (IX) above:

$R^{26}$ is selected from the group consisting of:
a) OH;
b) OCH$_3$;
c) fluorine and
d) chlorine.

$R^1$ is selected from the group consisting of

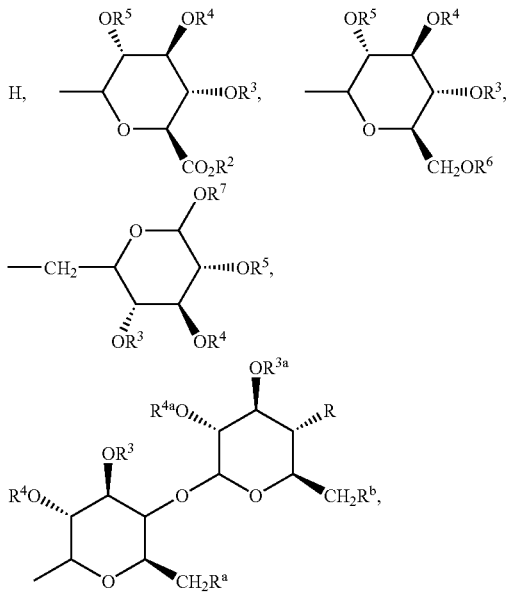

—SO$_3$H; natural and unnatural amino acids.

R, R$^a$ and R$^b$ are independently selected from the group consisting of H, —OH, halogeno, —NH$_2$, azido, (C$_1$–C$_6$) alkoxy(C$_1$–C$_6$)-alkoxy and —W—R$^{30}$;

W is independently selected from the group consisting of —NH—C(O)—, —O—C(O)—, —O—C(O)—N(R$^{31}$)—, —NH—C(O)—N(R$^{31}$)— and —O—C(S)—N(R$^{31}$)—;

R$^2$ and R$^6$ are independently selected from the group consisting of H, (C$_1$–C$_6$)alkyl, aryl and aryl(C$_1$–C$_6$)alkyl;

R$^3$, R$^4$, R$^5$, R$^7$, R$^{3a}$ and R$^{4a}$ are independently selected from the group consisting of H, (C$_1$–C$_6$)alkyl, aryl(C$_1$–C$_6$) alkyl, —C(O)(C$_1$–C$_6$)alkyl and —C(O)aryl;

R$^{30}$ is independently selected form the group consisting of R$^{32}$-substituted T, R$^{32}$-substituted-T—(C$_1$–C$_6$)alkyl, R$^{32}$-substituted-(C$_2$–C$_4$)alkenyl, R$^{32}$-substituted-(C$_1$–C$_6$)alkyl, R$^{32}$-substituted-(C$_3$–C$_7$)cycloalkyl and R$^{32}$-substituted-(C$_3$–C7)cycloalkyl(C$_1$–C$_6$)alkyl;

R$^{31}$ is independently selected from the group consisting of H and (C$_1$–C$_4$)alkyl;

T is independently selected from the group consisting of phenyl, furyl, thienyl, pyrrolyl, oxazolyl, isoxazolyl, thiazolyl, iosthiazolyl, benzothiazolyl, thiadiazolyl, pyrazolyl, imidazolyl and pyridyl;

R$^{32}$ is independently selected from 1–3 substituents independently selected from the group consisting of H, halogeno, (C$_1$–C$_4$)alkyl, —OH, phenoxy, —CF$_3$, —NO$_2$, (C$_1$–C$_4$)alkoxy, methylenedioxy, oxo, (C$_1$–C$_4$)alkylsulfanyl, (C$_1$–C$_4$)alkylsulfinyl, (C$_1$–C$_4$)alkylsulfonyl, —N(CH$_3$)$_2$, —C(O)—NH(C$_1$–C$_4$)alkyl, —C(O)—N((C$_1$–C$_4$)alkyl)$_2$, —C(O)—(C$_1$–C$_4$)alkyl, —C(O)—(C$_1$–C$_4$)alkoxy and pyrrolidinylcarbonyl; or R$^{32}$ is a covalent bond and R$^{31}$, the nitrogen to which it is attached and R$^{32}$ form a pyrrolidinyl, piperidinyl, N-methyl-piperazinyl, indolinyl or morpholinyl group, or a (C$_1$–C$_4$)alkoxycarbonyl-substituted pyrrolidinyl, piperidinyl, N-methylpiperazinyl, indolinyl or morpholinyl group;

Ar$^1$ is aryl or R$^{10}$-substituted aryl;
Ar$^2$ is aryl or R$^{11}$-substituted aryl;
Q is —(CH$_2$)$_q$—, wherein q is 2–6, or, with the 3-position ring carbon of the azetidinone, forms the spiro group

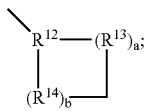

R$^{12}$ is

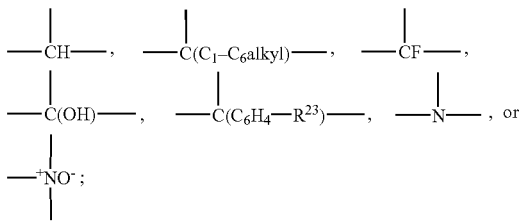

R$^{13}$ and R$^{14}$ are independently selected from the group consisting of —CH$_2$—, —CH(C$_1$–C$_6$ alkyl)-, —C(di-(C$_1$–C$_6$) alkyl), —CH═CH— and —C(C$_1$–C$_6$ alkyl)═CH—; or R$^{12}$ together with an adjacent R$^{13}$, or R$^{12}$ together with an adjacent R$^{14}$, form a —CH═CH— or a —CH═C(C$_1$–C$_6$)-alkyly group;

a and b are independently 0, 1, 2 or 3, provided both are not zero; provided that when R$^{13}$ is —CH═CH— or —C(C$_1$–C$_6$ alkyl)═CH—, a is 1; provided that when R$^{14}$ is —CH═CH— or —C(C$_1$–C$_6$ alkyl)═CH—, b is 1; provided that when a is 2 or 3, the R$^{13}$'s can be the same or different; and provided that when b is 2 or 3, the R$^{14}$'s can be the same or different;

R$^{10}$ and R$^{11}$ are independently selected from the group consisting of 1–3 substituents independently selected from the group consisting of (C$_1$–C$_6$)alkyl, —OR$^{19}$, —O(CO)R$^{19}$, —O(CO)OR$^{21}$, —O(CH$_2$)$_{1-5}$OR$^{19}$, —O(CO)NR$^{19}$R$^{20}$, —NR$^{19}$R$^{20}$, —NR$^{19}$(CO)R$^{20}$, —NR$^{19}$(CO)OR$^{21}$, —NR$^{19}$(CO)NR$^{20}$R$^{25}$, —NR$^{19}$SO$_2$R$^{21}$, —COOR$^{19}$, —CONR$^{19}$R$^{20}$, —COR$^{19}$, —SO$_2$NR$^{19}$R$^{20}$, S(O)$_{0-2}$R$^{21}$, —O(CH$_2$)$_{1-10}$—COOR$^{19}$, —O(CH$_2$)$_{1-10}$CONR$^{19}$R$^{20}$, —(C$_1$–C$_6$ alkylene)—COOR$^{19}$, —CH═CH—COOR$^{19}$, —CF$_3$, —CN, —NO$_2$ and halogen;

Ar$^1$ can also be pyridyl, isoxazolyl, furanyl, pyrrolyl, thienyl, imidazolyl, pyrazolyl, thiazolyl, pyrazinyl, pyrimidinyl or pyridazinyl;

$R^{19}$ and $R^{20}$ are independently selected from the group consisting of H, $(C_1-C_6)$alkyl, aryl and aryl-substituted $(C_1-C_6)$alkyl;

$R^{21}$ is $(C_1-C_6)$alkyl, aryl or $R^{24}$-substituted aryl;

$R^{22}$ is H, $(C_1-C_6)$alkyl, aryl $(C_1-C_6)$alkyl, —C(O)$R^{19}$ or —COO$R^{19}$;

$R^{23}$ and $R^{24}$ are independently 1–3 groups independently selected from the group consisting of H, $(C_1-C_6)$alkyl, $(C_1-C_6)$alkoxy, —COOH, NO$_2$, —NR$^{19}$R$^{20}$, —OH and halogeno; and $R^{25}$ is H, —OH or $(C_1-C_6)$alkoxy.

Ar$^2$ is preferably phenyl or $R^{11}$-phenyl, especially (4-$R^{11}$)-substituted phenyl. Preferred definitions of $R^{11}$ are lower alkoxy, especially methoxy, and halogeno, especially fluoro.

Ar$^1$ is preferably phenyl or $R^{10}$-substituted phenyl, especially (4-$R^{10}$)-substituted phenyl. A preferred definition of $R^{10}$ is halogeno, especially fluoro.

Preferably Q is a lower alkyl or a Spiro group as defined above, wherein preferably $R^{13}$ and $R^{14}$ are each ethylene and $R^{12}$ is

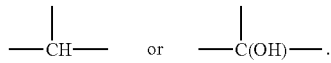

A preferred compound of formula IX, therefore, is one wherein $R^1$ is as defined above and in which the remaining variables have the following definitions:

Ar$^1$ is phenyl or $R^{10}$-substituted phenyl, wherein $R^{10}$ is halogeno;

Ar$^2$ is phenyl or $R^{11}$-phenyl, wherein $R^{11}$ is 1 to 3 substituents independently selected from the group consisting of $C_1-C_6$ alkoxy and halogeno;

Q is a lower alkyl (i.e. C-1 to C-2) with Q=C-2 being preferred, or Q, with the 3-position ring carbon of the azetidinone, forms the group

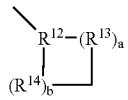

wherein preferably $R^{13}$ and $R^{14}$ are each ethylene and a and b are each 1, and wherein $R^{12}$ is

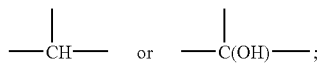

Preferred variables for $R^1$ groups of the formula

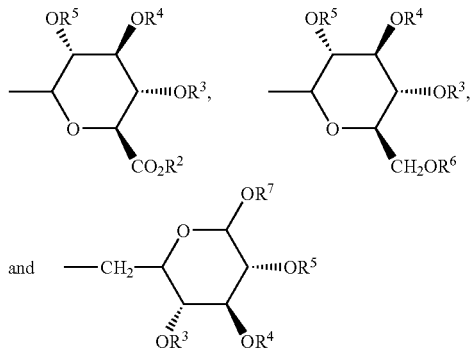

are as follows:

$R^2$, $R^3$, $R^4$, $R^5$, $R^6$ and $R^7$ are independently selected from the group consisting of H, $(C_1-C_6)$alkyl, benzyl and acetyl.

Preferred variables for group $R^1$ of the formula

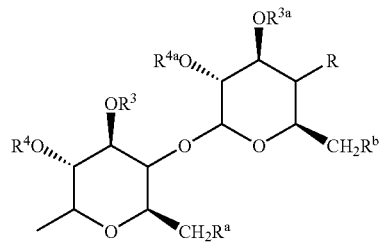

are as follows:

$R^3$, $R^{3a}$, $R^4$ and $R^{4a}$ are selected from the group consisting of H, $(C_1-C_6)$alkyl, benzyl and acetyl;

R, $R^a$ and $R^b$ are independently selected from the group consisting of H, —OH, halogeno, —NH$_2$, azido, $(C_1-C_6)$ alkoxy$(C_1-C_6)$alkoxy and —W—R$^{30}$, wherein W is —O—C(O)— or —O—C(O)—NR$^{31}$—, $R^{31}$ is H and $R^{30}$ is $(C_1-C_6)$alkyl, —C(O)—$(C_1-C_4)$alkoxy-$(C_1-C_6)$alkyl, T, T—$(C_1-C_6)$alkyl, or T or T—$(C_1-C_6)$alkyl wherein T is substituted by one or two halogeno or $(C_1-C_6)$alkyl groups.

Preferred $R^{30}$ substituents are 2-fluorophenyl, 2,4-difluoro-phenyl, 2,6-dichlorophenyl, 2-methylphenyl, 2-thienylmethyl, 2-methoxy-carbonylethyl, thiazol-2-yl-methyl, 2-furyl, 2-methoxycarbonylbutyl and phenyl. Preferred combinations of R, $R^a$ and $R^b$ are as follows: 1) R, $R^a$ and $R^b$ are independently —OH or —O—C(O)—NH—$R^{30}$, especially wherein $R^a$ is —OH and R and $R^b$ are —O—C(O)—NH—$R^{30}$ and $R^{30}$ is selected from the preferred substituents identified above, or wherein R and $R^a$ are —OH and $R^b$ is —O—C(O)—NH—$R^{30}$ wherein $R^{30}$ is 2-fluorophenyl, 2,4-difluoro-phenyl, 2,6-dichlorophenyl; 2) $R^a$ is —OH, halogeno, azido or $(C_1-C_6)$-alkoxy$(C_1-C_6)$ alkoxy, $R^b$ is H, halogeno, azido or $(C_1-C_6)$alkoxy$(C_1-C_6)$-alkoxy, and R is —O—C(O)—NH—$R^{30}$, especially compounds wherein $R^a$ is —OH, $R^b$ is H and $R^{30}$ is 2-fluorophenyl; 3) R, $R^a$ and $R^b$ are independently —OH or —O—C(O)$R^{30}$ and $R^{30}$ is $(C_1-C_6)$alkyl, T, or T substituted by one or two halogeno or $(C_1-C_6)$alkyl groups, especially compounds wherein R is —OH and $R^a$ and $R^b$ are —O—C(O)—$R^{30}$ wherein $R^{30}$ is 2-furyl; and 4) R, $R^a$ and $R^b$ are independently —OH or halogeno. Three additional classes of preferred are compounds are those wherein the $C^{1'}$ anomeric oxy is beta, wherein the $C^{2'}$ anomeric oxy is beta, and wherein the R group is alpha.

$R^1$ is preferably selected from:

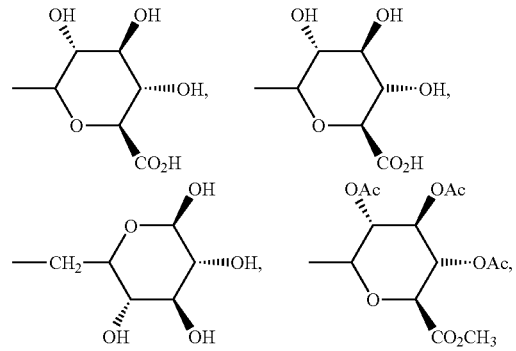

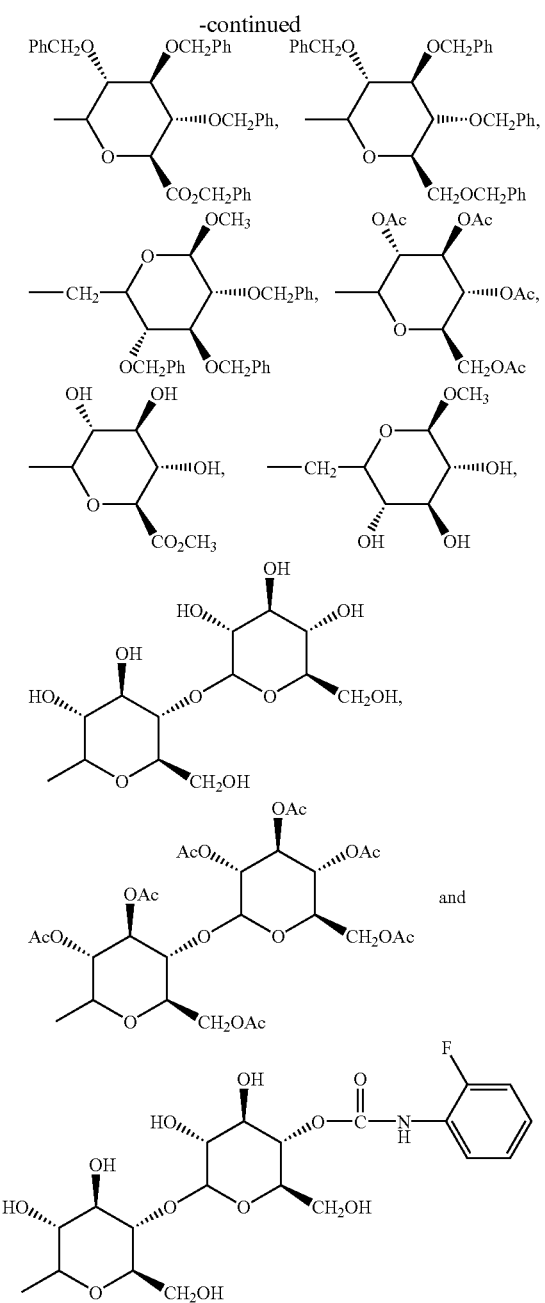

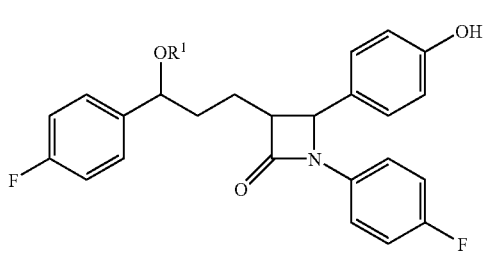

wherein Ac is acetyl and Ph is phenyl.

An example of a useful compound of this invention is one represented by the formula X:

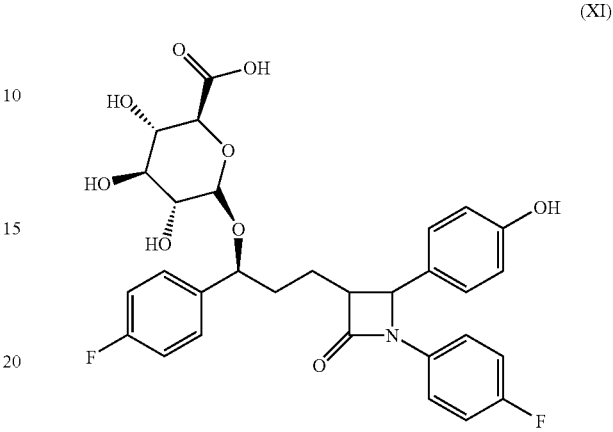

wherein $R^1$ is defined as above, or pharmaceutically acceptable salts or solvates of the compound of Formula (X), or prodrugs of the compound of Formula (X) or of the pharmaceutically acceptable salts or solvates of the compound of Formula (X).

A more preferred compound is one represented by formula XI:

(XI)

or pharmaceutically acceptable salts or solvates of the compound of Formula (XI), or prodrugs of the compound of Formula (XI) or of the pharmaceutically acceptable salts or solvates of the compound of Formula (XI).

In another embodiment, compositions, pharmaceutical compositions, therapeutic combinations, kits and methods of treatment as described above are provided which comprise: (a) at least one peroxisome proliferator-activated receptor activator; and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound, wherein the first amount and the second amount together in their totality (whether administered concurrently or consecutively) comprise a therapeutically effective amount for the treatment or prevention of a vascular condition, diabetes, obesity or lowering a concentration of a sterol in plasma of a mammal.

Suitable substituted azetidinone compounds or substituted β-lactam compounds can be selected from any of the compounds discussed above in Formulae I–XI. Other useful substituted azetidinone compounds include N-sulfonyl-2-azetidinones such as are disclosed in U.S. Pat. No. 4,983,597 and ethyl 4-(2-oxoazetidin-4-yl)phenoxy-alkanoates such as are disclosed in Ram et al., Indian J. Chem. Sect. B. 29B, 12 (1990), p. 1134–7, which are incorporated by reference herein.

The compounds of Formulae I–XI can be prepared by known methods, including the methods discussed above and, for example, WO 93/02048 describes the preparation of compounds wherein —$R^1$—Q— is alkylene, alkenylene or alkylene interrupted by a hetero atom, phenylene or cycloalkylene; WO 94/17038 describes the preparation of compounds wherein Q is a spirocyclic group; WO 95/08532 describes the preparation of compounds wherein —$R^1$—

Q— is a hydroxy-substituted alkylene group; PCT/US95/03196 describes compounds wherein —$R^1$—Q— is a hydroxy-substituted alkylene attached to the $Ar^1$ moiety through an —O— or $S(O)_{0-2}$-group; and U.S. Ser. No. 08/463,619, filed Jun. 5, 1995, describes the preparation of compounds wherein —$R^1$—Q— is a hydroxy-substituted alkylene group attached the azetidinone ring by a —$S(O)_{0-2}$-group.

The daily dose of the sterol absorption inhibitor(s) can range from about 0.1 to about 1000 mg per day, preferably about 0.25 to about 50 mg/day, and more preferably about 10 mg per day, given in a single dose or 2–4 divided doses. The exact dose, however, is determined by the attending clinician and is dependent on the potency of the compound administered, the age, weight, condition and response of the patient.

For administration of pharmaceutically acceptable salts of the above compounds, the weights indicated above refer to the weight of the acid equivalent or the base equivalent of the therapeutic compound derived from the salt.

In one embodiment of the present invention, the compositions or therapeutic combinations can further comprise one or more pharmacological or therapeutic agents or drugs such as cholesterol biosynthesis inhibitors and/or lipid-lowering agents discussed below.

In another embodiment, the composition or treatment can further comprise one or more cholesterol biosynthesis inhibitors coadministered with or in combination with the peroxisome proliferator-activated receptor activator(s) and sterol absorption inhibitor(s) discussed above.

Non-limiting examples of cholesterol biosynthesis inhibitors for use in the compositions, therapeutic combinations and methods of the present invention include competitive inhibitors of HMG CoA reductase, the rate-limiting step in cholesterol biosynthesis, squalene synthase inhibitors, squalene epoxidase inhibitors and mixtures thereof. Non-limiting examples of suitable HMG CoA reductase inhibitors include statins such as lovastatin (for example MEVACOR® which is available from Merck & Co.), pravastatin (for example PRAVACHOL® which is available from Bristol Meyers Squibb), fluvastatin, simvastatin (for example ZOCOR® which is available from Merck & Co.), atorvastatin, cerivastatin, CI-981, rivastatin (sodium 7-(4-fluorophenyl)-2,6-diisopropyl-5-methoxymethylpyridin-3-yl)-3,5-dihydroxy-6-heptanoate), rosuvastatin, pitavastatin (such as NK-104 of Negma Kowa of Japan); HMG CoA synthetase inhibitors, for example L-659,699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)—N-ethyl-N-(6,6-dimethyl-2-hepten-4-ynyl)-3-[(3,3'-bithiophen-5-yl)methoxy]benzene-methanamine hydrochloride) and other sterol biosynthesis inhibitors such as DMP-565. Preferred HMG CoA reductase inhibitors include lovastatin, pravastatin and simvastatin. The most preferred HMG CoA reductase inhibitor is simvastatin.

Generally, a total daily dosage of cholesterol biosynthesis inhibitor(s) can range from about 0.1 to about 160 mg per day, and preferably about 0.2 to about 80 mg/day in single or 2–3 divided doses.

In another preferred embodiment, the composition or treatment comprises the compound of Formula (II) in combination with one or more peroxisome proliferator-activated receptor(s) activator(s) and one or more cholesterol biosynthesis inhibitors. In this embodiment, preferably the peroxisome proliferator-activated receptor activator(s) is a fibric acid derivative selected from gemfibrozil, clofibrate and/or fenofibrate. Preferably the cholesterol biosynthesis inhibitor comprises one or more HMG CoA reductase inhibitors, such as, for example, lovastatin, pravastatin and/or simvastatin. More preferably, the composition or treatment comprises the compound of Formula (II) in combination with simvastatin and gemfibrozil or fenofibrate.

In another alternative embodiment, the compositions, therapeutic combinations or methods of the present invention can further comprise one or more bile acid sequestrants (insoluble anion exchange resins), coadministered with or in combination with the PPAR activators(s) and sterol absorption inhibitor(s) discussed above.

Bile acid sequestrants bind bile acids in the intestine, interrupting the enterohepatic circulation of bile acids and causing an increase in the faecal excretion of steroids. Use of bile acid sequestrants is desirable because of their non-systemic mode of action. Bile acid sequestrants can lower intrahepatic cholesterol and promote the synthesis of apo B/E (LDL) receptors that bind LDL from plasma to further reduce cholesterol levels in the blood. Non-limiting examples of suitable bile acid sequestrants include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly (allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Other useful bile acid sequestrants are disclosed in PCT Patent Applications Nos. WO 97/11345 and WO 98/57652, and U.S. Pat. Nos. 3,692,895 and 5,703,188 which are incorporated herein by reference. Suitable inorganic cholesterol sequestrants include bismuth salicylate plus montmorillonite clay, aluminum hydroxide and calcium carbonate antacids.

Generally, a total daily dosage of bile acid sequestrant(s) can range from about 1 to about 50 grams per day, and preferably about 2 to about 16 grams per day in single or 24 divided doses.

In an alternative embodiment, the compositions or treatments of the present invention can further comprise one or more ileal bile acid transport ("IBAT") inhibitors (or apical sodium co-dependent bile acid transport ("ASBT") inhibitors) coadministered with or in combination with the peroxisome proliferator-activated receptor activator(s) and sterol absorption inhibitor(s) discussed above. The IBAT inhibitors can inhibit bile acid transport to reduce LDL cholesterol levels. Non-limiting examples of suitable IBAT inhibitors include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

Generally, a total daily dosage of IBAT inhibitor(s) can range from about 0.01 to about 1000 mg/day, and preferably about 0.1 to about 50 mg/day in single or 24 divided doses.

In another alternative embodiment, the compositions or treatments of the present invention can further comprise nicotinic acid (niacin) and/or derivatives thereof coadministered with or in combination with the peroxisome proliferator-activated receptor activator(s) and sterol absorption inhibitor(s) discussed above.

As used herein, "nicotinic acid derivative" means a compound comprising a pyridine-3-carboxylate structure or a pyrazine-2-carboxylate structure, including acid forms, salts, esters, zwitterions and tautomers, where available. Examples of nicotinic acid derivatives include niceritrol, nicofuranose and acipimox (5-methylpyrazine-2-carboxylic acid 4-oxide). Nicotinic acid and its derivatives inhibit hepatic production of VLDL and its metabolite LDL and increases HDL and apo A-1 levels. An example of a suitable nicotinic acid product is NIASPAN® (niacin extended-release tablets) which are available from Kos.

Generally, a total daily dosage of nicotinic acid or a derivative thereof can range from about 500 to about 10,000 mg/day, preferably about 1000 to about 8000 mg/day, and more preferably about 3000 to about 6000 mg/day in single or divided doses.

In another alternative embodiment, the compositions or treatments of the present invention can further comprise one or more AcylCoA:Cholesterol O-acyltransferase ("ACAT") Inhibitors, which can reduce LDL and VLDL levels, coadministered with or in combination with the peroxisome proliferator-activated receptor activator(s) and sterol absorption inhibitor(s) discussed above. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors include avasimibe ([[2,4,6-tris(1-methylethyl)phenyl]acetyl] sulfamic acid, 2,6-bis(1-methylethyl)phenyl ester, formerly known as CI-1011), HL-004, lecimibide (DuP-128) and CL-277082 (N-(2,4-difluorophenyl)-N-[[4-(2,2-dimethylpropyl)phenyl]methyl]-N-heptylurea). See P. Chang et al., "Current, New and Future Treatments in Dyslipidaemia and Atherosclerosis", *Drugs* 2000 July; 60(1); 55–93, which is incorporated by reference herein.

Generally, a total daily dosage of ACAT inhibitor(s) can range from about 0.1 to about 1000 mg/day in single or 24 divided doses.

In another alternative embodiment, the compositions or treatments of the present invention can further comprise one or more Cholesteryl Ester Transfer Protein ("CETP") Inhibitors coadministered with or in combination with the peroxisome proliferator-activated receptor activator(s) and sterol absorption inhibitor(s) discussed above. CETP is responsible for the exchange or transfer of cholesteryl ester carrying HDL and triglycerides in VLDL.

Non-limiting examples of suitable CETP inhibitors are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be coadministered with or in combination with the peroxisome proliferator-activated receptor(s) activator and sterol absorption inhibitor (s) discussed above.

Generally, a total daily dosage of CETP inhibitor(s) can range from about 0.01 to about 1000 mg/day, and preferably about 0.5 to about 20 mg/kg body weight/day in single or divided doses.

In another alternative embodiment, the compositions or treatments of the present invention can further comprise probucol or derivatives thereof (such as AGI-1067 and other derivatives disclosed in U.S. Pat. Nos. 6,121,319 and 6,147, 250), which can reduce LDL levels, coadministered with or in combination with the peroxisome proliferator-activated receptor activator(s) and sterol absorption inhibitor(s) discussed above.

Generally, a total daily dosage of probucol or derivatives thereof can range from about 10 to about 2000 mg/day, and preferably about 500 to about 1500 mg/day in single or 24 divided doses.

In another alternative embodiment, the compositions or treatments of the present invention can further comprise low-density lipoprotein (LDL) receptor activators, coadministered with or in combination with the peroxisome proliferator-activated receptor activator(s) and sterol absorption inhibitor(s) discussed above. Non-limiting examples of suitable LDL-receptor activators include HOE-402, an imidazolidinyl-pyrimidine derivative that directly stimulates LDL receptor activity. See M. Huettinger et al., "Hypolipidemic activity of HOE402 is Mediated by Stimulation of the LDL Receptor Pathway", Arterioscler. Thromb. 1993; 13:1005–12.

Generally, a total daily dosage of LDL receptor activator (s) can range from about 1 to about 1000 mg/day in single or 24 divided doses.

In another alternative embodiment, the compositions or treatments of the present invention can further comprise fish oil, which contains Omega 3 fatty acids (3-PUFA), which can reduce VLDL and triglyceride levels, coadministered with or in combination with the peroxisome proliferator-activated receptor activator(s) and sterol absorption inhibitor (s) discussed above. Generally, a total daily dosage of fish oil or Omega 3 fatty acids can range from about 1 to about 30 grams per day in single or 2–4 divided doses.

In another alternative embodiment, the compositions or treatments of the present invention can further comprise natural water soluble fibers, such as psyllium, guar, oat and pectin, which can reduce cholesterol levels, coadministered with or in combination with the peroxisome proliferator-activated receptor activator(s) and sterol absorption inhibitor (s) discussed above. Generally, a total daily dosage of natural water soluble fibers can range from about 0.1 to about 10 grams per day in single or 2–4 divided doses.

In another alternative embodiment, the compositions or treatments of the present invention can further comprise plant sterols, plant stanols and/or fatty acid esters of plant stanols, such as sitostanol ester used in BENECOL® margarine, which can reduce cholesterol levels, coadministered with or in combination with the peroxisome proliferator-activated receptor activator(s) and sterol absorption inhibitor(s) discussed above. Generally, a total daily dosage of plant sterols, plant stanols and/or fatty acid esters of plant stanols can range from about 0.5 to about 20 grams per day in single or 2–4 divided doses.

In another alternative embodiment, the compositions or treatments of the present invention can further comprise antioxidants, such as probucol, tocopherol, ascorbic acid, β-carotene and selenium, or vitamins such as vitamin $B_6$ or vitamin $B_{12}$, coadministered with or in combination with the peroxisome proliferator-activated receptor activator(s) and sterol absorption inhibitor(s) discussed above. Generally, a total daily dosage of antioxidants or vitamins can range from about 0.05 to about 10 grams per day in single or 2–4 divided doses.

In another alternative embodiment, the compositions or treatments of the present invention can further comprise monocyte and macrophage inhibitors such as polyunsaturated fatty acids (PUFA), thyroid hormones including throxine analogues such as CGS-26214 (a thyroxine compound with a fluorinated ring), gene therapy and use of recombinant proteins such as recombinant apo E, coadministered with or in combination with the peroxisome proliferator-activated receptor activator(s) and sterol absorption inhibitor(s) discussed above. Generally, a total daily dosage of these agents can range from about 0.01 to about 1000 mg/day in single or 2–4 divided doses.

Also useful with the present invention are compositions or therapeutic combinations which further comprise hormone replacement agents and compositions. Useful hormone agents and compositions for hormone replacement therapy of the present invention include androgens, estrogens, progestins, their pharmaceutically acceptable salts and derivatives thereof. Combinations of these agents and compositions are also useful.

The dosage of androgen and estrogen combinations vary, desirably from about 1 mg to about 4 mg androgen and from about 1 mg to about 3 mg estrogen. Examples include, but are not limited to, androgen and estrogen combinations such as the combination of esterified estrogens (sodium estrone sulfate and sodium equilin sulfate) and methyltestosterone (17-hydroxy-17-methyl-, (17B)- androst-4-en-3-one) available from Solvay Pharmaceuticals, Inc., Marietta, Ga., under the tradename Estratest.

Estrogens and estrogen combinations may vary in dosage from about 0.01 mg up to 8 mg, desirably from about 0.3 mg to about 3.0 mg. Examples of useful estrogens and estrogen combinations include:

(a) the blend of nine (9) synthetic estrogenic substances including sodium estrone sulfate, sodium equilin sulfate, sodium 17 α-dihydroequilin sulfate, sodium 17 α-estradiol sulfate, sodium 17 β-dihydroequilin sulfate, sodium 17 α-dihydroequilenin sulfate, sodium 17 β-dihydroequilenin sulfate, sodium equilenin sulfate and sodium 17 β-estradiol sulfate; available from Duramed Pharmaceuticals, Inc., Cincinnati, Ohio, under the tradename Cenestin;

(b) ethinyl estradiol (19-nor-17 α-pregna-1,3,5(10)-trien-20-yne-3,17-diol; available by Schering Plough Corporation, Kenilworth, N.J., under the tradename Estinyl;

(c) esterified estrogen combinations such as sodium estrone sulfate and sodium equilin sulfate; available from Solvay under the tradename Estratab and from Monarch Pharmaceuticals, Bristol, Tenn., under the tradename Menest;

(d) estropipate (piperazine estra-1,3,5(10)-trien-17-one, 3-(sulfooxy)-estrone sulfate); available from Pharmacia & Upjohn, Peapack, N.J., under the tradename Ogen and from Women First Health Care, Inc., San Diego, Calif., under the tradename Ortho-Est; and (e) conjugated estrogens (17 α-dihydroequilin, 17 α-estradiol, and 17 β-dihydroequilin); available from Wyeth-Ayerst Pharmaceuticals, Philadelphia, Pa., under the tradename Premarin.

Progestins and estrogens may also be administered with a variety of dosages, generally from about 0.05 to about 2.0 mg progestin and about 0.001 mg to about 2 mg estrogen, desirably from about 0.1 mg to about 1 mg progestin and about 0.01 mg to about 0.5 mg estrogen. Examples of progestin and estrogen combinations that may vary in dosage and regimen include:

(a) the combination of estradiol (estra-1,3,5 (10)-triene-3, 17 β-diol hemihydrate) and norethindrone (17 β-acetoxy-19-nor-17 α-pregn-4-en-20-yn-3-one); which is available from Pharmacia & Upjohn, Peapack, N.J., under the tradename Activella;

(b) the combination of levonorgestrel (d(−)-13 β-ethyl-17 α-ethinyl-17 β-hydroxygon-4-en-3-one) and ethinyl estradial; available from Wyeth-Ayerst under the tradename Alesse, from Watson Laboratories, Inc., Corona, Calif., under the tradenames Levora and Trivora, Monarch Pharmaceuticals, under the tradename Nordette, and from Wyeth-Ayerst under the tradename Triphasil;

(c) the combination of ethynodiol diacetate (19-nor-17 a-pregn-4-en-20-yne-3 β, 17-diol diacetate) and ethinyl estradiol; available from G. D. Searle & Co., Chicago, Ill., under the tradename Demulen and from Watson under the tradename Zovia;

(d) the combination of desogestrel (13-ethyl-11-methylene-18,19-dinor-17 α-pregn-4-en-20-yn-17-ol) and ethinyl estradiol; available from Organon under the tradenames Desogen and Mircette, and from Ortho-McNeil Pharmaceutical, Raritan, N.J., under the tradename Ortho-Cept;

(e) the combination of norethindrone and ethinyl estradiol; available from Parke-Davis, Morris Plains, N.J., under the tradenames Estrostep and femhrt, from Watson under the tradenames Microgestin, Necon, and Tri-Norinyl, from Ortho-McNeil under the tradenames Modicon and Ortho-Novum, and from Warner Chilcott Laboratories, Rockaway, N.J., under the tradename Ovcon;

(f) the combination of norgestrel ((±)-13-ethyl-17-hydroxy-18, 19-dinor-17 α-preg-4-en-20-yn-3-one) and ethinyl estradiol; available from Wyeth-Ayerst under the tradenames Ovral and Lo/Ovral, and from Watson under the tradenames Ogestrel and Low-Ogestrel;

(g) the combination of norethindrone, ethinyl estradiol, and mestranol (3-methoxy-19-nor-17 α-pregna-1,3,5(10)-trien-20-yn-17-ol); available from Watson under the tradenames Brevicon and Norinyl;

(h) the combination of 17 β-estradiol (estra-1,3,5(10)-triene-3,17 β-diol) and micronized norgestimate (17 α-17-(Acetyloxyl)-13-ethyl-18,19-dinorpregn-4-en-20-yn-3-one3-oxime); available from Ortho-McNeil under the tradename Ortho-Prefest;

(i) the combination of norgestimate (18,19-dinor-17-pregn-4-en-20-yn-3-one, 17-(acetyloxy)-13-ethyl-,oxime, (17(α)-(+)-) and ethinyl estradiol; available from Ortho-McNeil under the tradenames Ortho Cyclen and Ortho Tri-Cyclen; and (j) the combination of conjugated estrogens (sodium estrone sulfate and sodium equilin sulfate) and medroxyprogesterone acetate (20-dione, 17-(acetyloxy)-6-methyl-, (6(α))- pregn-4-ene-3); available from Wyeth-Ayerst under the tradenames Premphase and Prempro.

In general, a dosage of progestins may vary from about 0.05 mg to about 10 mg or up to about 200 mg if microsized progesterone is administered. Examples of progestins include norethindrone; available from ESI Lederle, Inc., Philadelphia, Pa., under the tradename Aygestin, from Ortho-McNeil under the tradename Micronor, and from Watson under the tradename Nor-QD; norgestrel; available from Wyeth-Ayerst under the tradename Ovrette; micronized progesterone (pregn-4-ene-3,20-dione); available from Solvay under the tradename Prometrium; and medroxyprogesterone acetate; available from Pharmacia & Upjohn under the tradename Provera.

The compositions, therapeutic combinations or methods of the present invention can further comprise one or more obesity control medications. Useful obesity control medications include, but are not limited to, drugs that reduce energy intake or suppress appetite, drugs that increase energy expenditure and nutrient-partitioning agents. Suitable obesity control medications include, but are not limited to, noradrenergic agents (such as diethylpropion, mazindol, phenylpropanolamine, phentermine, phendimetrazine, phendamine tartrate, methamphetamine, phendimetrazine and tartrate); serotonergic agents (such as sibutramine, fenfluramine, dexfenfluramine, fluoxetine, fluvoxamine and paroxetine); thermogenic agents (such as ephedrine, caffeine, theophylline, and selective β3-adrenergic agonists); alpha-blocking agents; kainite or AMPA receptor antagonists; leptin-lipolysis stimulated receptors; phosphodiesterase enzyme inhibitors; compounds having nucleotide sequences of the mahogany gene; fibroblast growth factor-10 polypeptides; monoamine oxidase inhibitors (such as befloxatone, moclobemide, brofaromine, phenoxathine, esuprone, befol, toloxatone, pirlindol, amiflamine, sercloremine, bazinaprine, lazabemide, milacemide and caroxazone); compounds for increasing lipid metabolism (such as evodiamine compounds); and lipase inhibitors (such as orlistat). Generally, a total dosage of the above-described obesity control medications can range from 1 to 3,000 mg/day, desirably from about 1 to 1,000 mg/day and more desirably from about 1 to 200 mg/day in single or 2–4 divided doses.

The compositions, therapeutic combinations or methods of the present invention can further comprise one or more blood modifiers which are chemically different from the substituted azetidinone and substituted β-lactam compounds (such as compounds I–XI above) and the PPAR receptor activators discussed above, for example, they contain one or more different atoms, have a different arrangement of atoms or a different number of one or more atoms than the sterol absorption inhibitor(s) or PPAR receptor activators discussed above. Useful blood modifiers include but are not limited to anti-coagulants (argatroban, bivalirudin, dalteparin sodium, desirudin, dicumarol, lyapolate sodium, nafamostat mesylate, phenprocoumon, tinzaparin sodium, warfarin sodium); antithrombotic (anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab, zolimomab aritox); fibrinogen receptor antagonists (roxifiban acetate, fradafiban, orbofiban, lotrafiban hydrochloride, tirofiban, xemilofiban, monoclonal antibody 7E3, sibrafiban); platelet inhibitors (cilostazol, clopidogrel bisulfate, epoprostenol, epoprostenol sodium, ticlopidine hydrochloride, aspirin, ibuprofen, naproxen, sulindae, idomethacin, mefenamate, droxicam, diclofenac, sulfinpyrazone, piroxicam, dipyridamole); platelet aggregation inhibitors (acadesine, beraprost, beraprost sodium, ciprostene calcium, itazigrel, lifarizine, lotrafiban hydrochloride, orbofiban acetate, oxagrelate, fradafiban, orbofiban, tirofiban, xemilofiban); hemorrheologic agents (pentoxifylline); lipoprotein associated coagulation inhibitors; Factor VIIa inhibitors (4H-31-benzoxazin-4-ones, 4H-3,1-benzoxazin-4-thiones, quinazolin-4-ones, quinazolin-4-thiones, benzothiazin-4-ones, imidazolyl-boronic acid-derived peptide analogues TFPI-derived peptides, naphthalene-2-sulfonic acid {1-[3-(aminoiminomethyl)-benzyl]-2-oxo-pyrrolidin-3-(S)-yl} amide trifluoroacetate, dibenzofuran-2-sulfonic acid {1-[3-(aminomethyl)-benzyl]-5-oxo-pyrrolidin-3-yl}-amide, tolulene-4-sulfonic acid {1-[3-(aminoiminomethyl)-benzyl]-2-oxo-pyrrolidin-3-(S)-yl}-amide trifluoroacetate, 3,4-dihydro-1H-isoquinoline-2-sulfonic acid {1-[3-(aminoiminomethyl)-benzyl]-2-oxo-pyrrolin-3-(S)-yl}-amide trifluoroacetate); Factor Xa inhibitors (disubstituted pyrazolines, disubstituted triazolines, substituted n-[(aminoiminomethyl)phenyl]propylamides, substituted n-[(aminomethyl)phenyl] propylamides, tissue factor pathway inhibitor (TFPI), low molecular weight heparins, heparinoids, benzimidazolines, benzoxazolinones, benzopiperazinones, indanones, dibasic (amidinoaryl) propanoic acid derivatives, amidinophenyl-pyrrolidines, amidinophenyl-pyrrolines, amidinophenyl-isoxazolidines, amidinoindoles, amidinoazoles, bis-arylsulfonylaminobenzamide derivatives, peptidic Factor Xa inhibitors).

The compositions, therapeutic combinations or methods of the present invention can further comprise one or more cardiovascular agents which are chemically different from the substituted azetidinone and substituted β-lactam compounds (such as compounds I–XI above) and the PPAR receptor activators discussed above, for example, they contain one or more different atoms, have a different arrangement of atoms or a different number of one or more atoms than the sterol absorption inhibitor(s) or PPAR receptor activators discussed above. Useful cardiovascular agents include but are not limited to calcium channel blockers (clentiazem maleate, amlodipine besylate, isradipine, nimodipine, felodipine, nilvadipine, nifedipine, teludipine hydrochloride, diltiazem hydrochloride, belfosdil, verapamil hydrochloride, fostedil); adrenergic blockers (fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate, nebivolol); adrenergic stimulants; angiotensin converting enzyme (ACE) inhibitors (benazepril hydrochloride, benazeprilat, captopril, delapril hydrochloride, fosinopril sodium, libenzapril, moexipril hydrochloride, pentopril, perindopril, quinapril hydrochloride, quinaprilat, ramipril, spirapril hydrochloride, spiraprilat, teprotide, enalapril maleate, lisinopril, zofenopril calcium, perindopril erbumine); antihypertensive agents (althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzamine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate, bevantolol hydrochloride); angiotensin II receptor antagonists (candesartan, irbesartan, losartan potassium, candesartan cilexetil, telmisartan); anti-anginal agents (amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochoride, tosifen, verapamil hydrochloride); coronary vasodilators (fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexiline maleate, prenylamine, propatyl nitrate, terodiline hydrochloride, tolamolol, verapamil); diuretics (the combination product of hydrochlorothiazide and spironolactone and the combination product of hydrochlorothiazide and triamterene).

The compositions, therapeutic combinations or methods of the present invention can further comprise one or more antidiabetic medications for reducing blood glucose levels in a human. Useful antidiabetic medications include, but are not limited to, drugs that reduce energy intake or suppress appetite, drugs that increase energy expenditure and nutrient-partitioning agents. Suitable antidiabetic medications include, but are not limited to, sulfonylurea (such as acetohexamide, chlorpropamide, gliamilide, gliclazide, glimepiride, glipizide, glyburide, glibenclamide, tolazamide, and tolbutamide), meglitinide (such as repaglinide and nateglinide), biguamide (such as mefformin and buformin), alpha-glucosidase inhibitor (such as acarbose, miglitol, camiglibose, and voglibose), certain peptides (such as amlintide, pramlintide, exendin, and GLP-1 agonistic peptides), and orally administrable insulin or insulin composition for intestinal delivery thereof. Generally, a total dosage of the above-described antidiabetic medications can range from 0.1 to 1,000 mg/day in single or 24 divided doses.

Mixtures of any of the pharmacological or therapeutic agents described above can be used in the compositions and therapeutic combinations of the present invention.

In another embodiment, the present invention provides a composition or therapeutic combination comprising (a) at least one AcylCoA:Cholesterol O-acyltransferase Inhibitor and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or at least one substituted β-lactam compound.

In another embodiment, the present invention provides a composition or therapeutic combination comprising (a) probucol or a derivative thereof and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound.

In another embodiment, the present invention provides a composition or therapeutic combination comprising (a) at least one low-density lipoprotein receptor activator and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound.

In another embodiment, the present invention provides a composition or therapeutic combination comprising (a) at least one Omega 3 fatty acid and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound.

In another embodiment, the present invention provides a composition or therapeutic combination comprising (a) at least one natural water soluble fiber and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound.

In another embodiment, the present invention provides a composition or therapeutic combination comprising (a) at least one of plant sterols, plant stanols or fatty acid esters of plant stanols and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted β-lactam compound or of the isomers, salts or solvates of the at least one substituted azetidinone compound or the at least one substituted β-lactam compound.

In another embodiment, the present invention provides a composition or therapeutic combination comprising (a) at least one antioxidant or vitamin and (b) at least one substituted azetidinone compound or at least one substituted β-lactam compound, or isomers of the at least one substituted azetidinone compound or the at least one substituted β-lactam compound, or pharmaceutically acceptable salts or solvates of the at least one substituted azetidinone compound or the at least one substituted β-lactam compound or of the isomers of the at least one substituted azetidinone compound or the at least one substituted β-lactam compound, or prodrugs of the at least one substituted azetidinone compound or the at least one substituted lactam compound or of the isomers, salts or solvates of the at least one substituted azetidinone compound or the at least one substituted β-lactam compound.

Mixtures of any of the pharmacological or therapeutic agents described above can be used in the compositions and therapeutic combinations of these other embodiments of the present invention.

The compositions and therapeutic combinations of the present invention can be administered to a mammal in need of such treatment in a therapeutically effective amount to treat one or more conditions, for example vascular conditions such as atherosclerosis, hyperlipidaemia (including but not limited to hypercholesterolemia, hypertriglyceridaemia, sitosterolemia), vascular inflammation, stroke, diabetes, obesity, and/or reduce the level of sterol(s) in the plasma. The compositions and treatments can be administered by any suitable means which produce contact of these compounds with the site of action in the body, for example in the plasma, liver or small intestine of a mammal or human.

The daily dosage for the various compositions and therapeutic combinations described above can be administered to a patient in a single dose or in multiple subdoses, as desired. Subdoses can be administered 2 to 6 times per-day, for example. Sustained release dosages can be used. Where the peroxisome proliferator-activated receptor(s) activator and sterol absorption inhibitor(s) are administered in separate dosages, the number of doses of each component given per day may not necessarily be the same, e.g., one component may have a greater duration of activity and will therefore need to be administered less frequently.

The pharmaceutical treatment compositions and therapeutic combinations of the present invention can further comprise one or more pharmaceutically acceptable carriers, one or more excipients and/or one or more additives. Non-limiting examples of pharmaceutically acceptable carriers include solids and/or liquids such as ethanol, glycerol, water and the like. The amount of carrier in the treatment composition can range from about 5 to about 99 weight percent of the total weight of the treatment composition or therapeutic combination. Non-limiting examples of suitable pharmaceutically acceptable excipients and additives include non-toxic compatible fillers, binders such as starch, disintegrants, buffers, preservatives, anti-oxidants, lubricants, flavorings, thickeners, coloring agents, emulsifiers and the like. The amount of excipient or additive can range from about 0.1 to about 90 weight percent of the total weight of the treatment composition or therapeutic combination. One skilled in the art would understand that the amount of carrier(s), excipients and additives (if present) can vary.

The treatment compositions of the present invention can be administered in any conventional dosage form, preferably an oral dosage form such as a capsule, tablet, powder, cachet, suspension or solution. The formulations and pharmaceutical compositions can be prepared using conventional pharmaceutically acceptable and conventional techniques. Several examples of preparation of dosage formulations are provided below.

The following formulations exemplify some of the dosage forms of this invention. In each formulation, the term "Active Compound I" designates a substituted azetidinone compound, β-lactam compound or any of the compounds of Formulae I–XI described herein above, or isomers of the at least one substituted azetidinone compound or the at least one substituted β-lactam compound or any of the compounds of Formulae I–XI, or pharmaceutically acceptable salts or solvates of the at least one substituted azetidinone compound or the at least one substituted β-lactam compound or any of the compounds of Formulae I–XI or of the isomers of the at least one substituted azetidinone compound or the at least one substituted β-lactam compound or any of the compounds of Formulae I–XI, or prodrugs of the at least one substituted azetidinone compound or the at least one substituted β-lactam compound or any of the compounds of Formulae I–XI or of the isomers, salts or solvates of the at least one substituted azetidinone compound or the at least one substituted β-lactam compound or any of the compounds of Formulae I–XI, and the term "Active Compound II" designates a PPAR activator described herein above.

EXAMPLE

| | Tablets | |
|---|---|---|
| No. | Ingredient | mg/tablet |
| 1 | Active Compound I | 10 |
| 2 | Lactose monohydrate NF | 55 |
| 3 | Microcrystalline cellulose NF | 20 |
| 4 | Povidone (K29–32) USP | 4 |
| 5 | Croscarmellose sodium NF | 8 |
| 6 | Sodium lauryl sulfate | 2 |
| 7 | Magnesium stearate NF | 1 |
| | Total | 100 |

In the present invention, the above-described tablet can be coadministered with a tablet, capsule, etc. comprising a dosage of Active Compound II, for example a TRICOR® capsule as described above.

Method of Manufacture

Mix Item No. 4 with purified water in suitable mixer to form binder solution. Spray the binder solution and then water over Items 1, 2, 6 and a portion of Item 5 in a fluidized bed processor to granulate the ingredients. Continue fluidization to dry the damp granules. Screen the dried granules and blend with Item No. 3 and the remainder of Item 5. Add Item No. 7 and mix. Compress the mixture to appropriate size and weight on a suitable tablet machine.

For coadministration in separate tablets or capsules, representative formulations comprising a cholesterol absorption inhibitor such as are discussed above are well known in the art and representative formulations comprising a peroxisome proliferator-activated receptor activator such as are discussed above are well known in the art. It is contemplated that where the two active ingredients are administered as a single composition, the dosage forms disclosed above for substituted azetidinone or β-lactam compounds may readily be modified using the knowledge of one skilled in the art.

Since the present invention relates to treating conditions as discussed above, such as reducing the plasma sterol (especially cholesterol) concentrations or levels by treatment with a combination of active ingredients wherein the active ingredients may be administered separately, the invention also relates to combining separate pharmaceutical compositions in kit form. That is, a kit is contemplated wherein two separate units are combined: a pharmaceutical composition comprising at least one peroxisome proliferator-activated receptor activator and a separate pharmaceutical composition comprising at least one sterol absorption inhibitor as described above. The kit will preferably include directions for the administration of the separate components. The kit form is particularly advantageous when the separate components must be administered in different dosage forms (e.g., oral and parenteral) or are administered at different dosage intervals.

The treatment compositions and therapeutic combinations of the present invention can inhibit the intestinal absorption of cholesterol in mammals, as shown in the Example below, and can be useful in the treatment and/or prevention of conditions, for example vascular conditions, such as atherosclerosis, hypercholesterolemia and sitosterolemia, stroke, obesity and lowering of plasma levels of cholesterol in mammals, in particular in mammals.

In another embodiment of the present invention, the compositions and therapeutic combinations of the present invention can inhibit sterol absorption or reduce plasma concentration of at least one sterol selected from the group consisting of phytosterols (such as sitosterol, campesterol, stigmasterol and avenosterol), 5α-stanols (such as cholestanol, 5α-campestanol, 5α-sitostanol), cholesterol and mixtures thereof. The plasma concentration can be reduced by administering to a mammal in need of such treatment an effective amount of at least one treatment composition or therapeutic combination comprising at least one PPAR activator and at least one sterol absorption inhibitor described above. The reduction in plasma concentration of sterols can range from about 1 to about 70 percent, and preferably about 10 to about 50 percent. Methods of measuring serum total blood cholesterol and total LDL cholesterol are well known to those skilled in the art and for example include those disclosed in PCT WO 99/38498 at page 11, incorporated by reference herein. Methods of determining levels of other sterols in serum are disclosed in H. Gylling et al., "Serum Sterols During Stanol Ester Feeding in a Mildly Hypercholesterolemic Population", J. Lipid Res. 40: 593–600 (1999), incorporated by reference herein.

Illustrating the invention are the following examples which, however, are not to be considered as limiting the invention to their details. Unless otherwise indicated, all parts and percentages in the following examples, as well as throughout the specification, are by weight.

EXAMPLES

Preparation of Compound of Formula (II)

Step 1): To a solution of (S)-4-phenyl-2-oxazolidinone (41 g, 0.25 mol) in $CH_2Cl_2$ (200 ml), was added 4-dimethylaminopyridine (2.5 g, 0.02 mol) and triethylamine (84.7 ml, 0.61 mol) and the reaction mixture was cooled to 0° C. Methyl-4-(chloroformyl)butyrate (50 g, 0.3 mol) was added as a solution in $CH_2Cl_2$ (375 ml) dropwise over 1 h, and the reaction was allowed to warm to 22° C. After 17 h, water and $H_2SO_4$ (2N, 100 ml), was added the layers were separated, and the organic layer was washed sequentially with NaOH (10%), NaCl (sat'd) and water. The organic layer was dried over $MgSO_4$ and concentrated to obtain a semicrystalline product.

Step 2): To a solution of $TiCl_4$ (18.2 ml, 0.165 mol) in $CH_2Cl_2$ (600 ml) at 0° C., was added titanium isopropoxide (16.5 ml, 0.055 mol). After 15 min, the product of Step 1 (49.0 g, 0.17 mol) was added as a solution in $CH_2Cl_2$ (100 ml). After 5 min., diisopropylethylamine (DIPEA) (65.2 ml, 0.37 mol) was added and the reaction mixture was stirred at 0° C. for 1 h, the reaction mixture was cooled to −20° C., and 4-benzyloxybenzylidine(4-fluoro)aniline (114.3 g, 0.37 mol) was added as a solid. The reaction mixture was stirred vigorously for 4 h at −20° C., then acetic acid was added as a solution in $CH_2Cl_2$ dropwise over 15 min, the reaction mixture was allowed to warm to 0° C., and $H_2SO_4$ (2N) was added. The reaction mixture was stirred an additional 1 h, the layers were separated, washed with water, separated and the organic layer was dried. The crude product was crystallized from ethanol/water to obtain the pure intermediate.

Step 3): To a solution of the product of Step 2 (8.9 g, 14.9 mmol) in toluene (100 ml) at 50° C., was added N,O-bis(trimethylsilyl)acetamide (BSA) (7.50 ml, 30.3 mmol). After 0.5 h, solid TBAF (0.39 g, 1.5 mmol) was added and the reaction mixture stirred at 50° C. for an additional 3 h. The reaction mixture was cooled to 22° C., $CH_3OH$ (10 ml), was added. The reaction mixture was washed with HCl (1 N), $NaHCO_3$ (1 N) and NaCl (sat'd.), and the organic layer was dried over $MgSO_4$.

Step 4): To a solution of the product of Step 3 (0.94 g, 2.2 mmol) in $CH_3OH$ (3 ml), was added water (1 ml) and $LiOH.H_2O$ (102 mg, 2.4 mmole). The reaction mixture was stirred at 22° C. for 1 h and then additional $LiOH.H_2O$ (54 mg, 1.3 mmole) was added. After a total of 2 h, HCl (1 N) and EtOAc was added, the layers were separated, the organic layer was dried and concentrated in vacuo. To a solution of the resultant product (0.91 g, 2.2 mmol) in $CH_2Cl_2$ at 22° C., was added ClCOCOCl (0.29 ml, 3.3 mmol) and the mixture stirred for 16 h. The solvent was removed in vacuo.

Step 5): To an efficiently stirred suspension of 4-fluorophenylzinc chloride (4.4 mmol) prepared from 4-fluorophenylmagnesium bromide (1M in THF, 4.4 ml, 4.4 mmol) and $ZnCl_2$ (0.6 g, 4.4 mmol) at 4° C., was added tetrakis(triphenyl-phosphine)palladium (0.25 g, 0.21 mmol) followed by the product of Step 4 (0.94 g, 2.2 mmol) as a solution in THF (2 ml). The reaction was stirred for 1 h at 0° C. and then for 0.5 h at 22° C. HCl (1 N, 5 ml) was added and the mixture was extracted with EtOAc. The organic layer was concentrated to an oil and purified by silica gel chromatography to obtain 1-(4-fluorophenyl)-4-(S)-(4-hydroxyphenyl)-3(R)-(3-oxo-3-phenylpropyl)-2-azetidinone: HRMS calc'd for $C_{24}H_{19}F_2NO_3$=408.1429, found 408.1411.

Step 6): To the product of Step 5 (0.95 g, 1.91 mmol) in THF (3 ml), was added (R)-tetrahydro-1-methyl-3,3-diphenyl-1H,3H-pyrrolo-[1,2-c][1,3,2] oxazaborole (120 mg, 0.43 mmol) and the mixture was cooled to −20° C. After 5 min, borohydride-dimethylsulfide complex (2M in THF, 0.85 ml, 1.7 mmol) was added dropwise over 0.5 h. After a total of 1.5 h, $CH_3OH$ was added followed by HCl (1 N) and the reaction mixture was extracted with EtOAc to obtain 1-(4-fluorophenyl)-3(R)-[3(S)-(4-fluorophenyl)-3-hydroxypropyl)]-4(S)-[4-(phenylmethoxy)phenyl]-2-azetidinone (compound 6A-1) as an oil. $^1H$ in $CDCl_3$ d H3=4.68. J=2.3 Hz. Cl (M$^+$H) 500.

Use of (S)-tetra-hydro-1-methyl-3,3-diphenyl-1H,3H-pyrrolo-[1,2-c][1,3,2] oxazaborole gives the corresponding 3(R)-hydroxypropyl azetidinone (compound 6B-1). $^1H$ in $CDCl_3$ d H3=4.69. J=2.3 Hz. Cl (M$^+$H) 500.

To a solution of compound 6A-1 (0.4 g, 0.8 mmol) in ethanol (2 ml), was added 10% Pd/C (0.03 g) and the reaction mixture was stirred under a pressure (60 psi) of $H_2$ gas for 16 h. The reaction mixture was filtered and the solvent was concentrated to obtain compound 6A. Mp 164–166° C.; Cl (M$^+$H) 410. $[\alpha]_D^{25}$=−28.1° (c 3, $CH_3OH$) Elemental analysis calc'd for $C_{24}H_{21}F_2NO_3$: C 70.41; H 5.17; N 3.42; found C 70.25; H 5.19; N 3.54.

Similarly treat compound 6B-1 to obtain compound 6B.

Mp 129.5–132.5° C.; Cl (M$^+$H)410. Elemental analysis calc'd for $C_{24}H_{21}F_2NO_3$: C 70.41; H 5.17; N 3.42; found C 70.30; H 5.14; N 3.52.

Step 6' (Alternative): To a solution of the product of Step 5 (0.14 g, 0.3 mmol) in ethanol (2 ml), was added 10% Pd/C (0.03 g) and the reaction was stirred under a pressure (60 psi) of H2 gas for 16 h. The reaction mixture was filtered and the solvent was concentrated to afford a 1:1 mixture of compounds 6A and 6B.

In Vivo Evaluation

In a randomized, evaluator-blind, placebo-controlled, parallel-group study 32 healthy hypercholesterolemic humans (screening LDL-C≧130 mg/dL) stabilized and maintained on a NCEP Step I Diet were randomized to one of the following four treatments:

Treatment A—placebo given orally as 1 dose per day,

Treatment B—10 mg of Compound II given orally as 1 dose per day,

Treatment C—200 mg of LIPANTHYL® micronized Fenofibrate (available from Labortoire Fournier of France) given orally as 1 dose per day, or Treatment D—200 mg of LIPANTHYL® micronized Fenofibrate plus 10 mg of Compound II given orally as 1 dose per day every morning for 14 days. Serum lipids were assessed predose (after a minimum of a 10-hour fast) on Day 1 (Baseline), Day 7 and Day 14.

Results: The mean (S.E.) Day 14 percent (%) change from Baseline in serum lipids (n=8) are shown in Table 1 below:

TABLE 1

| Treatment | LDL-C | Total-C | HDL-C | TG |
| --- | --- | --- | --- | --- |
| A | −10.1 (4.9) | −8.38 (4.0) | −14.1 (2.2) | 19.1 (13.9) |
| B | −22.3 (5.7) | −19.6 (4.0) | −13.3 (4.4) | −4.57 (12.8) |
| C | −13.5 (3.1) | −13.0 (2.4) | −6.1 (3.6) | 0.28 (11.4) |
| D | −36.3 (3.5) | −27.8 (1.7) | −1.97 (4.7) | −32.4 (4.5) |

The coadministration of 10 mg of Compound II and 200 mg of Fenofibrate (Treatment D) was well tolerated and caused a significant (p≦0.03) reduction in LDL-C compared to either drug alone or placebo. In this inpatient study where the subjects' physical activity was restricted, in general HDL-C concentrations tended to decrease and triglycerides tended to increase. The group receiving Treatment C had the least decrease in HDL-C and the greatest decrease in triglyceride levels.

It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

I claim:

1. A pharmaceutical composition consisting of:

| Ingredient | Weight percent of ingredient |
| --- | --- |
| Compound of Formula (II) | 10 |
| Lactose monohydrate | 55 |
| Microcrystalline cellulose | 20 |
| Povidone | 4 |
| Croscarmellose sodium | 8 |
| Sodium lauryl sulfate | 2 |
| Magnesium stearate | 1 |
| Total | 100 | wherein the compound represented by Formula (II) below is:

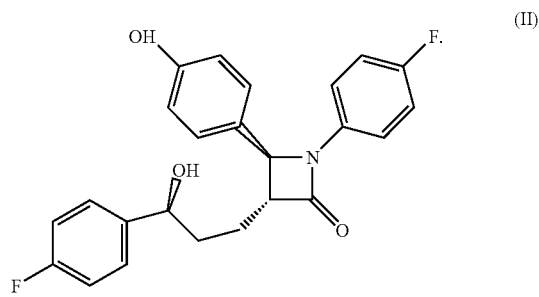

(II)

2. A pharmaceutical composition consisting essentially of:

| Ingredient | milligrams of ingredient |
| --- | --- |
| Compound of Formula (II) | 10 |
| Lactose monohydrate | 55 |
| Microcrystalline cellulose | 20 |
| Povidone | 4 |
| Croscarmellose sodium | 8 |
| Sodium lauryl sulfate | 2 |
| Magnesium stearate | 1 |
| Total | 100 | wherein the compound represented by Formula (II) below is:

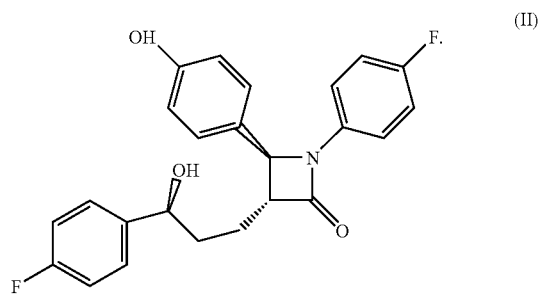

(II)

* * * * *